(12) United States Patent
Singhal et al.

(10) Patent No.: US 11,710,153 B2
(45) Date of Patent: Jul. 25, 2023

(54) AUTONOMY FIRST ROUTE OPTIMIZATION FOR AUTONOMOUS VEHICLES

(71) Applicant: NIO Technology (Anhui) Co., Ltd., Anhui (CN)

(72) Inventors: Abhishek Singhal, Santa Clara, CA (US); Gautam Muralidhar, San Jose, CA (US); Christopher F. Pouliot, San Mateo, CA (US); Edward H. Baik, Mountain View, CA (US); Jonathan A. Cox, San Jose, CA (US)

(73) Assignee: NIO Technology (Anhui) Co., Ltd., Hefei (CN)

( * ) Notice: Subject to any disclaimer, the term of this patent is extended or adjusted under 35 U.S.C. 154(b) by 267 days.

(21) Appl. No.: 17/202,823

(22) Filed: Mar. 16, 2021

(65) Prior Publication Data

US 2021/0201357 A1 Jul. 1, 2021

Related U.S. Application Data

(63) Continuation of application No. 15/395,952, filed on Dec. 30, 2016, now Pat. No. 10,970,746.

(Continued)

(51) Int. Cl.
*G06Q 30/02* (2023.01)
*G06Q 30/0251* (2023.01)
(Continued)

(52) U.S. Cl.
CPC .......... *G06Q 30/0266* (2013.01); *A61B 5/01* (2013.01); *A61B 5/024* (2013.01); *A61B 5/08* (2013.01);
(Continued)

(58) Field of Classification Search
CPC .. G06Q 30/0266; G06Q 30/0269; A61B 5/01; A61B 5/024; A61B 5/08;
(Continued)

(56) References Cited

U.S. PATENT DOCUMENTS 4,361,202 A 11/1982 Minovitch
4,476,954 A 10/1984 Johnson et al.
(Continued)

FOREIGN PATENT DOCUMENTS

CN 1417755 5/2003
CN 1847817 10/2006
(Continued)

OTHER PUBLICATIONS

Examiner's Answer for U.S. Appl. No. 15/727,838, dated May 4, 2021 17 pages.

(Continued)

*Primary Examiner* — Behrang Badii
(74) *Attorney, Agent, or Firm* — Sheridan Ross, PC

(57) ABSTRACT

Embodiments herein can determine an optimal route for an autonomous electric vehicle. The system may score viable routes between the start and end locations of a trip using a numeric or other scale that denotes how viable the route is for autonomy. The score is adjusted using a variety of factors where a learning process leverages both offline and online data. The scored routes are not based simply on the shortest distance between the start and end points but determine the best route based on the driving context for the vehicle and the user.

20 Claims, 12 Drawing Sheets

Related U.S. Application Data

(60) Provisional application No. 62/424,976, filed on Nov. 21, 2016.

(51) Int. Cl.

| | | |
|---|---|---|
| *G06F 16/29* | (2019.01) | |
| *G01S 13/86* | (2006.01) | |
| *G01S 15/02* | (2006.01) | |
| *G08G 1/16* | (2006.01) | |
| *G06F 16/95* | (2019.01) | |
| *B62D 15/02* | (2006.01) | |
| *G01C 21/34* | (2006.01) | |
| *G01S 13/87* | (2006.01) | |
| *B60S 1/56* | (2006.01) | |
| *G01C 21/36* | (2006.01) | |
| *B60R 11/04* | (2006.01) | |
| *B60S 1/62* | (2006.01) | |
| *G01S 7/40* | (2006.01) | |
| *G01S 7/497* | (2006.01) | |
| *G01S 17/89* | (2020.01) | |
| *G02B 27/00* | (2006.01) | |
| *B60W 30/09* | (2012.01) | |
| *B60W 50/00* | (2006.01) | |
| *G05D 1/00* | (2006.01) | |
| *G05D 1/02* | (2020.01) | |
| *A61B 5/01* | (2006.01) | |
| *A61B 5/024* | (2006.01) | |
| *A61B 5/08* | (2006.01) | |
| *A61B 5/16* | (2006.01) | |
| *A61B 5/18* | (2006.01) | |
| *B60W 40/09* | (2012.01) | |
| *B60W 50/08* | (2020.01) | |
| *B60W 10/18* | (2012.01) | |
| *B60W 10/20* | (2006.01) | |
| *B60W 10/04* | (2006.01) | |
| *B60W 40/04* | (2006.01) | |
| *B60W 40/08* | (2012.01) | |
| *B60W 40/105* | (2012.01) | |
| *B62D 15/00* | (2006.01) | |
| *G01S 13/931* | (2020.01) | |

(52) U.S. Cl.
CPC ............... *A61B 5/165* (2013.01); *A61B 5/18* (2013.01); *B60R 11/04* (2013.01); *B60S 1/56* (2013.01); *B60S 1/62* (2013.01); *B60W 10/04* (2013.01); *B60W 10/18* (2013.01); *B60W 10/20* (2013.01); *B60W 30/09* (2013.01); *B60W 40/04* (2013.01); *B60W 40/08* (2013.01); *B60W 40/09* (2013.01); *B60W 40/105* (2013.01); *B60W 50/0097* (2013.01); *B60W 50/0098* (2013.01); *B60W 50/08* (2013.01); *B60W 50/082* (2013.01); *B62D 15/00* (2013.01); *B62D 15/0265* (2013.01); *G01C 21/3407* (2013.01); *G01C 21/3461* (2013.01); *G01C 21/3469* (2013.01); *G01C 21/3484* (2013.01); *G01C 21/3492* (2013.01); *G01C 21/3682* (2013.01); *G01C 21/3691* (2013.01); *G01C 21/3697* (2013.01); *G01S 7/4021* (2013.01); *G01S 7/497* (2013.01); *G01S 13/862* (2013.01); *G01S 13/865* (2013.01); *G01S 13/867* (2013.01); *G01S 13/87* (2013.01); *G01S 15/02* (2013.01); *G01S 17/89* (2013.01); *G02B 27/0006* (2013.01); *G05D 1/0061* (2013.01); *G05D 1/0088* (2013.01); *G05D 1/0212* (2013.01); *G05D 1/0214* (2013.01); *G05D 1/0221* (2013.01); *G05D 1/0276* (2013.01); *G06F 16/29* (2019.01); *G06F 16/95* (2019.01); *G06Q 30/0269* (2013.01); *G08G 1/161* (2013.01); *G08G 1/163* (2013.01); *G08G 1/164* (2013.01); *G08G 1/165* (2013.01); *G08G 1/166* (2013.01); *B60W 2040/0809* (2013.01); *B60W 2050/0004* (2013.01); *B60W 2050/0014* (2013.01); *B60W 2300/34* (2013.01); *B60W 2510/08* (2013.01); *B60W 2510/18* (2013.01); *B60W 2520/04* (2013.01); *B60W 2520/105* (2013.01); *B60W 2540/043* (2020.02); *B60W 2540/18* (2013.01); *B60W 2540/22* (2013.01); *B60W 2540/30* (2013.01); *B60W 2554/00* (2020.02); *B60W 2554/80* (2020.02); *B60W 2710/18* (2013.01); *B60W 2710/20* (2013.01); *B60W 2756/10* (2020.02); *B60W 2900/00* (2013.01); *G01S 7/4043* (2021.05); *G01S 2007/4977* (2013.01); *G01S 2013/932* (2020.01); *G01S 2013/9316* (2020.01); *G01S 2013/9318* (2020.01); *G01S 2013/9319* (2020.01); *G01S 2013/9322* (2020.01); *G01S 2013/9325* (2013.01); *G01S 2013/93185* (2020.01); *G01S 2013/93271* (2020.01); *G01S 2013/93272* (2020.01); *G01S 2013/93273* (2020.01); *G01S 2013/93274* (2020.01); *G01S 2013/93275* (2020.01); *G05D 2201/0212* (2013.01)

(58) Field of Classification Search
CPC . A61B 5/165; A61B 5/18; B60R 11/04; B60S 1/56; B60S 1/62; B60W 10/04; B60W 10/18; B60W 10/20; B60W 30/09; B60W 40/04; B60W 40/08; B60W 40/09; B60W 40/105; B60W 50/0097; B60W 50/0098; B60W 50/08; B60W 50/082; B60W 2040/0809; B60W 2050/0004; B60W 2050/0014; B60W 2300/34; B60W 2510/08; B60W 2510/18; B60W 2520/04; B60W 2520/105; B60W 2540/043; B60W 2540/18; B60W 2540/22; B60W 2540/30; B60W 2554/00; B60W 2554/80; B60W 2710/18; B60W 2710/20; B60W 2756/10; B60W 2900/00; B60W 2050/143; B60W 2556/45; B60W 2556/55; B60W 2556/65; B60W 10/00; B60W 10/06; B60W 10/08; B60W 10/10; B60W 30/08; B60W 30/095; B60W 30/0953; B60W 30/0956; B62D 15/00; B62D 15/0265; G01C 21/3407; G01C 21/3461; G01C 21/3469; G01C 21/3484; G01C 21/3492; G01C 21/3682; G01C 21/3691; G01C 21/3697; G01S 7/4021; G01S 7/497; G01S 13/865; G01S 13/867; G01S 13/87; G01S 15/02; G01S 17/89; G01S 7/4043; G01S 2007/4977; G01S 2013/9316; G01S 2013/9318; G01S 2013/93185; G01S 2013/9319; G01S 2013/932; G01S 2013/9322; G01S 2013/9325; G01S 2013/93271; G01S 2013/93272; G01S 2013/93273; G01S 2013/93274; G01S 2013/93275; G02B 27/0006; G05D 1/0061; G05D 1/0088; G05D 1/0212; G05D 1/0214; G05D 1/0221; G05D 1/0276; G05D 2201/0212; G06F 16/29;

G06F 16/95; G08G 1/161; G08G 1/163;
G08G 1/164; G08G 1/165; G08G 1/166
See application file for complete search history.

(56) References Cited

U.S. PATENT DOCUMENTS

| | | | |
|---|---|---|---|
| 4,754,255 A | 6/1988 | Sanders et al. |
| 4,875,391 A | 10/1989 | Leising et al. |
| 5,035,302 A | 7/1991 | Thangavelu |
| 5,136,498 A | 8/1992 | McLaughlin et al. |
| 5,204,817 A | 4/1993 | Yoshida |
| 5,363,306 A | 11/1994 | Kuwahara et al. |
| 5,508,689 A | 4/1996 | Rado et al. |
| 5,521,815 A | 5/1996 | Rose |
| 5,529,138 A | 6/1996 | Shaw et al. |
| 5,531,122 A | 7/1996 | Chatham et al. |
| 5,572,450 A | 11/1996 | Worthy |
| 5,610,821 A | 3/1997 | Gazis et al. |
| 5,648,769 A | 7/1997 | Sato et al. |
| 5,710,702 A | 1/1998 | Hayashi et al. |
| 5,794,164 A | 8/1998 | Beckert et al. |
| 5,797,134 A | 8/1998 | McMillan et al. |
| 5,812,067 A | 9/1998 | Bergholz et al. |
| 5,825,283 A | 10/1998 | Camhi |
| 5,838,251 A | 11/1998 | Brinkmeyer et al. |
| 5,847,661 A | 12/1998 | Ricci |
| 5,890,080 A | 3/1999 | Coverdill et al. |
| 5,928,294 A | 7/1999 | Zelinkovsky |
| 5,949,345 A | 9/1999 | Beckert et al. |
| 5,983,161 A | 11/1999 | Lemelson et al. |
| 5,986,575 A | 11/1999 | Jones et al. |
| 6,038,426 A | 3/2000 | Williams, Jr. |
| 6,081,756 A | 6/2000 | Mio et al. |
| D429,684 S | 8/2000 | Johnson |
| 6,128,003 A | 10/2000 | Smith et al. |
| 6,137,425 A | 10/2000 | Oster et al. |
| 6,141,620 A | 10/2000 | Zyburt et al. |
| 6,148,261 A | 11/2000 | Obradovich et al. |
| 6,152,514 A | 11/2000 | McLellen |
| 6,157,321 A | 12/2000 | Ricci |
| 6,198,996 B1 | 3/2001 | Berstis |
| 6,199,001 B1 | 3/2001 | Ohta et al. |
| 6,202,008 B1 | 3/2001 | Beckert et al. |
| 6,252,544 B1 | 6/2001 | Hoffberg |
| 6,253,161 B1 | 6/2001 | Arias-Estrada |
| 6,267,428 B1 | 7/2001 | Baldas et al. |
| 6,302,438 B1 | 10/2001 | Stopper, Jr. et al. |
| 6,310,542 B1 | 10/2001 | Gehlot |
| 6,317,058 B1 | 11/2001 | Lemelson et al. |
| 6,339,826 B2 | 1/2002 | Hayes, Jr. et al. |
| 6,356,838 B1 | 3/2002 | Paul |
| 6,388,579 B1 | 5/2002 | Adcox et al. |
| 6,393,137 B1 | 5/2002 | Chen et al. |
| 6,480,224 B1 | 11/2002 | Brown |
| 6,480,762 B1 | 11/2002 | Uchikubo et al. |
| 6,502,022 B1 | 12/2002 | Chastain et al. |
| 6,519,519 B1 | 2/2003 | Stopczynski |
| 6,557,752 B1 | 5/2003 | Yacoob |
| 6,563,910 B2 | 5/2003 | Menard et al. |
| 6,587,739 B1 | 7/2003 | Abrams et al. |
| 6,598,227 B1 | 7/2003 | Berry et al. |
| 6,607,212 B1 | 8/2003 | Reimer et al. |
| 6,617,981 B2 | 9/2003 | Basinger |
| 6,633,800 B1 | 10/2003 | Ward |
| 6,662,077 B2 | 12/2003 | Haag |
| 6,675,081 B2 | 1/2004 | Shuman et al. |
| 6,678,747 B2 | 1/2004 | Goossen et al. |
| 6,681,176 B2 | 1/2004 | Funk et al. |
| 6,690,260 B1 | 2/2004 | Ashihara |
| 6,690,940 B1 | 2/2004 | Brown et al. |
| 6,724,920 B1 | 4/2004 | Berenz et al. |
| 6,754,580 B1 | 6/2004 | Ask et al. |
| 6,757,593 B2 | 6/2004 | Mori et al. |
| 6,762,684 B1 | 7/2004 | Camhi |
| 6,765,495 B1 | 7/2004 | Dunning et al. |
| 6,778,888 B2 | 8/2004 | Cataldo et al. |
| 6,782,240 B1 | 8/2004 | Tabe |
| 6,785,531 B2 | 8/2004 | Lepley et al. |
| 6,816,783 B2 | 11/2004 | Hashima et al. |
| 6,820,259 B1 | 11/2004 | Kawamata et al. |
| 6,944,533 B2 | 9/2005 | Obradovich et al. |
| 6,950,022 B2 | 9/2005 | Breed |
| 6,958,707 B1 | 10/2005 | Siegel |
| 6,992,580 B2 | 1/2006 | Kotzin et al. |
| 7,019,641 B1 | 3/2006 | Lakshmanan et al. |
| 7,020,544 B2 | 3/2006 | Shinada et al. |
| 7,021,691 B1 | 4/2006 | Schmidt et al. |
| 7,042,345 B2 | 5/2006 | Ellis |
| 7,047,129 B2 | 5/2006 | Uotani |
| 7,058,898 B2 | 6/2006 | McWalter et al. |
| 7,096,431 B2 | 8/2006 | Tambata et al. |
| 7,142,696 B1 | 11/2006 | Engelsberg et al. |
| 7,164,117 B2 | 1/2007 | Breed et al. |
| 7,187,947 B1 | 3/2007 | White |
| 7,203,598 B1 | 4/2007 | Whitsell |
| 7,233,861 B2 | 6/2007 | Van Buer et al. |
| 7,239,960 B2 | 7/2007 | Yokota et al. |
| 7,277,454 B2 | 10/2007 | Mocek et al. |
| 7,284,769 B2 | 10/2007 | Breed |
| 7,289,645 B2 | 10/2007 | Yamamoto et al. |
| 7,295,921 B2 | 11/2007 | Spencer et al. |
| 7,313,547 B2 | 12/2007 | Mocek et al. |
| 7,333,012 B1 | 2/2008 | Nguyen |
| 7,343,148 B1 | 3/2008 | O'Neil |
| 7,386,376 B2 | 6/2008 | Basir et al. |
| 7,386,799 B1 | 6/2008 | Clanton et al. |
| 7,432,829 B2 | 10/2008 | Poltorak |
| 7,474,264 B2 | 1/2009 | Bolduc et al. |
| 7,493,140 B2 | 2/2009 | Michmerhuizen et al. |
| 7,526,539 B1 | 4/2009 | Hsu |
| 7,548,815 B2 | 6/2009 | Watkins et al. |
| 7,566,083 B2 | 7/2009 | Vitito |
| 7,606,660 B2 | 10/2009 | Diaz et al. |
| 7,606,867 B1 | 10/2009 | Singhal et al. |
| 7,643,913 B2 | 1/2010 | Taki et al. |
| 7,650,234 B2 | 1/2010 | Obradovich et al. |
| 7,671,764 B2 | 3/2010 | Uyeki et al. |
| 7,680,596 B2 | 3/2010 | Uyeki et al. |
| 7,683,771 B1 | 3/2010 | Loeb |
| 7,711,468 B1 | 5/2010 | Levy |
| 7,734,315 B2 | 6/2010 | Rathus et al. |
| 7,748,021 B2 | 6/2010 | Obradovich et al. |
| RE41,449 E | 7/2010 | Krahnstoever et al. |
| 7,791,499 B2 | 9/2010 | Mohan et al. |
| 7,796,190 B2 | 9/2010 | Basso et al. |
| 7,802,832 B2 | 9/2010 | Carnevali |
| 7,821,421 B2 | 10/2010 | Tamir et al. |
| 7,832,762 B2 | 11/2010 | Breed |
| 7,864,073 B2 | 1/2011 | Lee et al. |
| 7,872,591 B2 | 1/2011 | Kane et al. |
| 7,873,471 B2 | 1/2011 | Gieseke |
| 7,881,703 B2 | 2/2011 | Roundtree et al. |
| 7,891,004 B1 | 2/2011 | Gelvin et al. |
| 7,891,719 B2 | 2/2011 | Carnevali |
| 7,894,951 B2 | 2/2011 | Norris et al. |
| 7,899,610 B2 | 3/2011 | McClellan |
| 7,966,678 B2 | 6/2011 | Ten Eyck et al. |
| 7,969,290 B2 | 6/2011 | Waeller et al. |
| 7,969,324 B2 | 6/2011 | Chevion et al. |
| 8,060,631 B2 | 11/2011 | Collart et al. |
| 8,064,925 B1 | 11/2011 | Sun et al. |
| 8,066,313 B2 | 11/2011 | Carnevali |
| 8,098,170 B1 | 1/2012 | Szczerba et al. |
| 8,113,564 B2 | 2/2012 | Carnevali |
| 8,131,419 B2 | 3/2012 | Ampunan et al. |
| 8,157,310 B2 | 4/2012 | Carnevali |
| 8,162,368 B2 | 4/2012 | Carnevali |
| 8,175,802 B2 | 5/2012 | Forstall et al. |
| 8,233,919 B2 | 7/2012 | Haag et al. |
| 8,245,609 B1 | 8/2012 | Greenwald et al. |
| 8,306,514 B1 | 11/2012 | Nunally |
| 8,334,847 B2 | 12/2012 | Tomkins |
| 8,346,233 B2 | 1/2013 | Aaron et al. |
| 8,346,432 B2 | 1/2013 | Van Wiemeersch et al. |
| 8,350,721 B2 | 1/2013 | Carr |

(56) References Cited

U.S. PATENT DOCUMENTS

| | | |
|---|---|---|
| 8,352,282 B2 | 1/2013 | Jensen et al. |
| 8,369,263 B2 | 2/2013 | Dowling et al. |
| 8,391,554 B2 | 3/2013 | Lee et al. |
| 8,417,449 B1 | 4/2013 | Denise |
| 8,428,843 B2 | 4/2013 | Lee et al. |
| 8,432,260 B2 | 4/2013 | Talty et al. |
| 8,442,389 B2 | 5/2013 | Kashima et al. |
| 8,442,758 B1 | 5/2013 | Rovik et al. |
| 8,467,965 B2 | 6/2013 | Chang |
| 8,497,842 B2 | 7/2013 | Tomkins et al. |
| 8,498,809 B2 | 7/2013 | Bill |
| 8,509,982 B2 | 8/2013 | Montemerlo et al. |
| 8,521,410 B2 | 8/2013 | Mizuno et al. |
| 8,527,143 B2 | 9/2013 | Tan |
| 8,527,146 B1 | 9/2013 | Jackson et al. |
| 8,532,574 B2 | 9/2013 | Kirsch |
| 8,543,330 B2 | 9/2013 | Taylor et al. |
| 8,547,340 B2 | 10/2013 | Sizelove et al. |
| 8,548,669 B2 | 10/2013 | Naylor |
| 8,559,183 B1 | 10/2013 | Davis |
| 8,577,600 B1 | 11/2013 | Pierfelice |
| 8,578,279 B2 | 11/2013 | Chen et al. |
| 8,583,292 B2 | 11/2013 | Preston et al. |
| 8,589,073 B2 | 11/2013 | Guha et al. |
| 8,600,611 B2 | 12/2013 | Seize |
| 8,613,385 B1 | 12/2013 | Hulet et al. |
| 8,621,645 B1 | 12/2013 | Spackman |
| 8,624,727 B2 | 1/2014 | Saigh et al. |
| 8,634,980 B1 | 1/2014 | Urmson et al. |
| 8,634,984 B2 | 1/2014 | Sumizawa |
| 8,644,165 B2 | 2/2014 | Saarimaki et al. |
| 8,660,735 B2 | 2/2014 | Tengler et al. |
| 8,671,068 B2 | 3/2014 | Harber et al. |
| 8,688,372 B2 | 4/2014 | Bhogal et al. |
| 8,698,639 B2 | 4/2014 | Fung et al. |
| 8,705,527 B1 | 4/2014 | Addepalli et al. |
| 8,706,143 B1 | 4/2014 | Elias |
| 8,718,797 B1 | 5/2014 | Addepalli et al. |
| 8,718,910 B2 | 5/2014 | Gueziec |
| 8,725,311 B1 | 5/2014 | Breed |
| 8,730,033 B2 | 5/2014 | Yarnold et al. |
| 8,737,986 B2 | 5/2014 | Rhoads et al. |
| 8,761,673 B2 | 6/2014 | Sakata |
| 8,774,842 B2 | 7/2014 | Jones et al. |
| 8,779,947 B2 | 7/2014 | Tengler et al. |
| 8,782,262 B2 | 7/2014 | Collart et al. |
| 8,793,065 B2 | 7/2014 | Seltzer et al. |
| 8,798,918 B2 | 8/2014 | Onishi et al. |
| 8,805,110 B2 | 8/2014 | Rhoads et al. |
| 8,812,171 B2 | 8/2014 | Fillev et al. |
| 8,817,761 B2 | 8/2014 | Gruberman et al. |
| 8,825,031 B2 | 9/2014 | Aaron et al. |
| 8,825,277 B2 | 9/2014 | McClellan et al. |
| 8,825,382 B2 | 9/2014 | Liu |
| 8,826,261 B1 | 9/2014 | Anand Ag et al. |
| 8,838,088 B1 | 9/2014 | Henn et al. |
| 8,862,317 B2 | 10/2014 | Shin et al. |
| 8,972,090 B2 | 3/2015 | Weslati et al. |
| 8,977,408 B1 | 3/2015 | Cazanas et al. |
| 9,043,016 B2 | 5/2015 | Filippov et al. |
| 9,163,952 B2 | 10/2015 | Viola et al. |
| 9,180,783 B1 | 11/2015 | Penilla et al. |
| 9,188,985 B1 | 11/2015 | Hobbs et al. |
| 9,229,905 B1 | 1/2016 | Penilla et al. |
| 9,285,240 B2 | 3/2016 | Yenamandra et al. |
| 9,299,251 B2 | 3/2016 | Scofield et al. |
| 9,360,342 B2 | 6/2016 | Ignatin |
| 9,371,007 B1 | 6/2016 | Penilla et al. |
| 9,488,493 B2 | 11/2016 | MacNeille et al. |
| 9,581,460 B1 | 2/2017 | McNew et al. |
| 9,663,118 B1 | 5/2017 | Palmer et al. |
| 9,714,837 B2 | 7/2017 | North et al. |
| 9,969,404 B2 | 5/2018 | McNew |
| 10,077,056 B1 | 9/2018 | Fields et al. |
| 10,216,190 B2 | 2/2019 | Bostick et al. |
| 10,217,160 B2 | 2/2019 | Penilla et al. |
| 10,234,302 B2 | 3/2019 | Singhal et al. |
| 10,272,793 B2 | 4/2019 | Perry et al. |
| 10,281,296 B2 | 5/2019 | MacNeille et al. |
| 10,286,915 B2 | 5/2019 | Xiao et al. |
| 10,339,621 B2 | 7/2019 | Hirose et al. |
| 10,360,518 B2 | 7/2019 | Hirose et al. |
| 10,410,250 B2 | 9/2019 | Singhal et al. |
| 10,471,829 B2 | 11/2019 | Yellambalase et al. |
| 10,606,274 B2 | 3/2020 | Yalla et al. |
| 10,635,109 B2 | 4/2020 | Guo et al. |
| 10,837,790 B2 | 11/2020 | Singhal |
| 10,935,978 B2 | 3/2021 | Yalla et al. |
| 10,970,746 B2 | 4/2021 | Singhal et al. |
| 2001/0010516 A1 | 8/2001 | Roh et al. |
| 2001/0015888 A1 | 8/2001 | Shaler et al. |
| 2002/0009978 A1 | 1/2002 | Dukach et al. |
| 2002/0023010 A1 | 2/2002 | Rittmaster et al. |
| 2002/0026278 A1 | 2/2002 | Feldman et al. |
| 2002/0045484 A1 | 4/2002 | Eck et al. |
| 2002/0065046 A1 | 5/2002 | Mankins et al. |
| 2002/0077985 A1 | 6/2002 | Kobata et al. |
| 2002/0095249 A1 | 7/2002 | Lang |
| 2002/0097145 A1 | 7/2002 | Tumey et al. |
| 2002/0103622 A1 | 8/2002 | Burge |
| 2002/0105968 A1 | 8/2002 | Pruzan et al. |
| 2002/0126876 A1 | 9/2002 | Paul et al. |
| 2002/0128774 A1 | 9/2002 | Takezaki et al. |
| 2002/0143461 A1 | 10/2002 | Burns et al. |
| 2002/0143643 A1 | 10/2002 | Catan |
| 2002/0152010 A1 | 10/2002 | Colmenarez et al. |
| 2002/0154217 A1 | 10/2002 | Ikeda |
| 2002/0169531 A1 | 11/2002 | Kawazoe et al. |
| 2002/0169551 A1 | 11/2002 | Inoue et al. |
| 2002/0174021 A1 | 11/2002 | Chu et al. |
| 2003/0004624 A1 | 1/2003 | Wilson et al. |
| 2003/0007227 A1 | 1/2003 | Ogino |
| 2003/0055557 A1 | 3/2003 | Dutta et al. |
| 2003/0060937 A1 | 3/2003 | Shinada et al. |
| 2003/0060977 A1 | 3/2003 | Jijina et al. |
| 2003/0065432 A1 | 4/2003 | Shuman et al. |
| 2003/0101451 A1 | 5/2003 | Bentolila et al. |
| 2003/0109972 A1 | 6/2003 | Tak |
| 2003/0125846 A1 | 7/2003 | Yu et al. |
| 2003/0132666 A1 | 7/2003 | Bond et al. |
| 2003/0149530 A1 | 8/2003 | Stopczynski |
| 2003/0158638 A1 | 8/2003 | Yakes et al. |
| 2003/0182435 A1 | 9/2003 | Redlich et al. |
| 2003/0202683 A1 | 10/2003 | Ma et al. |
| 2003/0204290 A1 | 10/2003 | Sadler et al. |
| 2003/0209893 A1 | 11/2003 | Breed et al. |
| 2003/0230443 A1 | 12/2003 | Cramer et al. |
| 2004/0017292 A1 | 1/2004 | Reese et al. |
| 2004/0024502 A1 | 2/2004 | Squires et al. |
| 2004/0036622 A1 | 2/2004 | Dukach et al. |
| 2004/0039500 A1 | 2/2004 | Amendola et al. |
| 2004/0039504 A1 | 2/2004 | Coffee et al. |
| 2004/0068364 A1 | 4/2004 | Zhao et al. |
| 2004/0070920 A1 | 4/2004 | Flueli |
| 2004/0093155 A1 | 5/2004 | Simonds et al. |
| 2004/0117494 A1 | 6/2004 | Mitchell et al. |
| 2004/0128062 A1 | 7/2004 | Ogino et al. |
| 2004/0153356 A1 | 8/2004 | Lockwood et al. |
| 2004/0162019 A1 | 8/2004 | Horita et al. |
| 2004/0180653 A1 | 9/2004 | Royalty |
| 2004/0182574 A1 | 9/2004 | Adnan et al. |
| 2004/0193347 A1 | 9/2004 | Harumoto et al. |
| 2004/0203974 A1 | 10/2004 | Seibel |
| 2004/0204837 A1 | 10/2004 | Singleton |
| 2004/0209594 A1 | 10/2004 | Naboulsi |
| 2004/0217850 A1 | 11/2004 | Perttunen et al. |
| 2004/0225557 A1 | 11/2004 | Phelan et al. |
| 2004/0249568 A1 | 12/2004 | Endo et al. |
| 2004/0255123 A1 | 12/2004 | Noyama et al. |
| 2004/0257208 A1 | 12/2004 | Huang et al. |
| 2004/0260470 A1 | 12/2004 | Rast |
| 2005/0012599 A1 | 1/2005 | DeMatteo |
| 2005/0031100 A1 | 2/2005 | Iggulden et al. |
| 2005/0038598 A1 | 2/2005 | Oesterling et al. |

(56) References Cited

U.S. PATENT DOCUMENTS

| | | |
|---|---|---|
| 2005/0042999 A1 | 2/2005 | Rappaport |
| 2005/0065678 A1 | 3/2005 | Smith et al. |
| 2005/0065711 A1 | 3/2005 | Dahlgren et al. |
| 2005/0086051 A1 | 4/2005 | Brulle-Drews |
| 2005/0092542 A1 | 5/2005 | Turner |
| 2005/0093717 A1 | 5/2005 | Lilja |
| 2005/0097541 A1 | 5/2005 | Holland |
| 2005/0114864 A1 | 5/2005 | Surace |
| 2005/0122235 A1 | 6/2005 | Teffer et al. |
| 2005/0124211 A1 | 6/2005 | Diessner et al. |
| 2005/0130744 A1 | 6/2005 | Eck et al. |
| 2005/0144156 A1 | 6/2005 | Barber |
| 2005/0149752 A1 | 7/2005 | Johnson et al. |
| 2005/0153760 A1 | 7/2005 | Varley |
| 2005/0159853 A1 | 7/2005 | Takahashi et al. |
| 2005/0159892 A1 | 7/2005 | Chung |
| 2005/0192727 A1 | 9/2005 | Shostak et al. |
| 2005/0197748 A1 | 9/2005 | Holst et al. |
| 2005/0197767 A1 | 9/2005 | Nortrup |
| 2005/0234614 A1 | 10/2005 | Sakurai et al. |
| 2005/0234679 A1 | 10/2005 | Karlsson |
| 2005/0251324 A1 | 11/2005 | Wiener et al. |
| 2005/0261815 A1 | 11/2005 | Cowelchuk et al. |
| 2005/0278093 A1 | 12/2005 | Kameyama |
| 2005/0283284 A1 | 12/2005 | Grenier et al. |
| 2006/0015819 A1 | 1/2006 | Hawkins et al. |
| 2006/0036358 A1 | 2/2006 | Hale et al. |
| 2006/0044119 A1 | 3/2006 | Egelhaaf |
| 2006/0047386 A1 | 3/2006 | Kanevsky et al. |
| 2006/0058948 A1 | 3/2006 | Blass et al. |
| 2006/0059229 A1 | 3/2006 | Bain et al. |
| 2006/0125631 A1 | 6/2006 | Sharony |
| 2006/0130033 A1 | 6/2006 | Stoffels et al. |
| 2006/0142933 A1 | 6/2006 | Feng |
| 2006/0173841 A1 | 8/2006 | Bill |
| 2006/0175403 A1 | 8/2006 | McConnell et al. |
| 2006/0184319 A1 | 8/2006 | Seick et al. |
| 2006/0212909 A1 | 9/2006 | Girard et al. |
| 2006/0217864 A1 | 9/2006 | Johnson et al. |
| 2006/0241836 A1 | 10/2006 | Kachouh et al. |
| 2006/0243056 A1 | 11/2006 | Sundermeyer et al. |
| 2006/0250272 A1 | 11/2006 | Puamau |
| 2006/0253307 A1 | 11/2006 | Warren et al. |
| 2006/0259210 A1 | 11/2006 | Tanaka et al. |
| 2006/0274829 A1 | 12/2006 | Siemens et al. |
| 2006/0282204 A1 | 12/2006 | Breed |
| 2006/0287807 A1 | 12/2006 | Tetter |
| 2006/0287865 A1 | 12/2006 | Cross et al. |
| 2006/0288382 A1 | 12/2006 | Vitito |
| 2006/0290516 A1 | 12/2006 | Muehlsteff et al. |
| 2006/0293856 A1 | 12/2006 | Foessel et al. |
| 2007/0001831 A1 | 1/2007 | Raz et al. |
| 2007/0002032 A1 | 1/2007 | Powers et al. |
| 2007/0010942 A1 | 1/2007 | Bill |
| 2007/0015485 A1 | 1/2007 | DeBiasio et al. |
| 2007/0028370 A1 | 2/2007 | Seng |
| 2007/0032225 A1 | 2/2007 | Konicek et al. |
| 2007/0057781 A1 | 3/2007 | Breed |
| 2007/0061957 A1 | 3/2007 | Huang et al. |
| 2007/0067614 A1 | 3/2007 | Berry et al. |
| 2007/0069880 A1 | 3/2007 | Best et al. |
| 2007/0083298 A1 | 4/2007 | Pierce et al. |
| 2007/0088488 A1 | 4/2007 | Reeves et al. |
| 2007/0103328 A1 | 5/2007 | Lakshmanan et al. |
| 2007/0115101 A1 | 5/2007 | Creekbaum et al. |
| 2007/0118301 A1 | 5/2007 | Andarawis et al. |
| 2007/0120697 A1 | 5/2007 | Ayoub et al. |
| 2007/0135995 A1 | 6/2007 | Kikuchi et al. |
| 2007/0156317 A1 | 7/2007 | Breed |
| 2007/0182625 A1 | 8/2007 | Kerai et al. |
| 2007/0182816 A1 | 8/2007 | Fox |
| 2007/0185969 A1 | 8/2007 | Davis |
| 2007/0192486 A1 | 8/2007 | Wilson et al. |
| 2007/0194902 A1 | 8/2007 | Blanco et al. |
| 2007/0194944 A1 | 8/2007 | Galera et al. |
| 2007/0195997 A1 | 8/2007 | Paul et al. |
| 2007/0200663 A1 | 8/2007 | White et al. |
| 2007/0208860 A1 | 9/2007 | Zellner et al. |
| 2007/0213090 A1 | 9/2007 | Holmberg |
| 2007/0228826 A1 | 10/2007 | Jordan et al. |
| 2007/0233341 A1 | 10/2007 | Logsdon |
| 2007/0250228 A1 | 10/2007 | Reddy et al. |
| 2007/0257815 A1 | 11/2007 | Gunderson et al. |
| 2007/0276596 A1 | 11/2007 | Solomon et al. |
| 2007/0280505 A1 | 12/2007 | Breed |
| 2008/0005974 A1 | 1/2008 | Delgado Vazquez et al. |
| 2008/0023253 A1 | 1/2008 | Prost-Fin et al. |
| 2008/0027337 A1 | 1/2008 | Dugan et al. |
| 2008/0033635 A1 | 2/2008 | Obradovich et al. |
| 2008/0042824 A1 | 2/2008 | Kates |
| 2008/0051957 A1 | 2/2008 | Breed et al. |
| 2008/0052627 A1 | 2/2008 | Oguchi |
| 2008/0071465 A1 | 3/2008 | Chapman et al. |
| 2008/0082237 A1 | 4/2008 | Breed |
| 2008/0086455 A1 | 4/2008 | Meisels et al. |
| 2008/0090522 A1 | 4/2008 | Oyama |
| 2008/0104227 A1 | 5/2008 | Birnie et al. |
| 2008/0119994 A1 | 5/2008 | Kameyama |
| 2008/0129475 A1 | 6/2008 | Breed et al. |
| 2008/0143085 A1 | 6/2008 | Breed et al. |
| 2008/0147280 A1 | 6/2008 | Breed |
| 2008/0148374 A1 | 6/2008 | Spaur et al. |
| 2008/0154712 A1 | 6/2008 | Wellman |
| 2008/0154957 A1 | 6/2008 | Taylor et al. |
| 2008/0161986 A1 | 7/2008 | Breed |
| 2008/0164985 A1 | 7/2008 | Iketani et al. |
| 2008/0169940 A1 | 7/2008 | Lee et al. |
| 2008/0174451 A1 | 7/2008 | Harrington et al. |
| 2008/0212215 A1 | 9/2008 | Schofield et al. |
| 2008/0216067 A1 | 9/2008 | Villing |
| 2008/0228358 A1 | 9/2008 | Wang et al. |
| 2008/0234919 A1 | 9/2008 | Ritter et al. |
| 2008/0252487 A1 | 10/2008 | McClellan et al. |
| 2008/0253613 A1 | 10/2008 | Jones et al. |
| 2008/0255721 A1 | 10/2008 | Yamada |
| 2008/0255722 A1 | 10/2008 | McClellan et al. |
| 2008/0269958 A1 | 10/2008 | Filev et al. |
| 2008/0281508 A1 | 11/2008 | Fu |
| 2008/0300778 A1 | 12/2008 | Kuznetsov |
| 2008/0305780 A1 | 12/2008 | Williams et al. |
| 2008/0319602 A1 | 12/2008 | McClellan et al. |
| 2009/0006525 A1 | 1/2009 | Moore |
| 2009/0024251 A1 | 1/2009 | Myeong et al. |
| 2009/0024419 A1 | 1/2009 | McClellan et al. |
| 2009/0037719 A1 | 2/2009 | Sakthikumar et al. |
| 2009/0040026 A1 | 2/2009 | Tanaka |
| 2009/0055178 A1 | 2/2009 | Coon |
| 2009/0082951 A1 | 3/2009 | Graessley |
| 2009/0099720 A1 | 4/2009 | Elgali |
| 2009/0112393 A1 | 4/2009 | Maten et al. |
| 2009/0112452 A1 | 4/2009 | Buck et al. |
| 2009/0119657 A1 | 5/2009 | Link, II |
| 2009/0125174 A1 | 5/2009 | Delean |
| 2009/0132294 A1 | 5/2009 | Haines |
| 2009/0138336 A1 | 5/2009 | Ashley et al. |
| 2009/0144622 A1 | 6/2009 | Evans et al. |
| 2009/0157312 A1 | 6/2009 | Black et al. |
| 2009/0158200 A1 | 6/2009 | Palahnuk et al. |
| 2009/0180668 A1 | 7/2009 | Jones et al. |
| 2009/0189373 A1 | 7/2009 | Schramm et al. |
| 2009/0189979 A1 | 7/2009 | Smyth |
| 2009/0195370 A1 | 8/2009 | Huffman et al. |
| 2009/0210257 A1 | 8/2009 | Chalfant et al. |
| 2009/0216935 A1 | 8/2009 | Flick |
| 2009/0222200 A1 | 9/2009 | Link et al. |
| 2009/0224931 A1 | 9/2009 | Dietz et al. |
| 2009/0224942 A1 | 9/2009 | Goudy et al. |
| 2009/0234578 A1 | 9/2009 | Newby et al. |
| 2009/0241883 A1 | 10/2009 | Nagoshi et al. |
| 2009/0254446 A1 | 10/2009 | Chernyak |
| 2009/0264849 A1 | 10/2009 | La Croix |
| 2009/0275321 A1 | 11/2009 | Crowe |
| 2009/0278750 A1 | 11/2009 | Man et al. |
| 2009/0278915 A1 | 11/2009 | Kramer et al. |

(56) References Cited

U.S. PATENT DOCUMENTS

| | | |
|---|---|---|
| 2009/0279839 A1 | 11/2009 | Nakamura et al. |
| 2009/0284359 A1 | 11/2009 | Huang et al. |
| 2009/0287405 A1 | 11/2009 | Liu et al. |
| 2009/0299572 A1 | 12/2009 | Fujikawa et al. |
| 2009/0312998 A1 | 12/2009 | Berckmans et al. |
| 2009/0319181 A1 | 12/2009 | Khosravy et al. |
| 2010/0004856 A1 | 1/2010 | Kobori et al. |
| 2010/0008053 A1 | 1/2010 | Osternack et al. |
| 2010/0023204 A1 | 1/2010 | Basir et al. |
| 2010/0035620 A1 | 2/2010 | Naden et al. |
| 2010/0036560 A1 | 2/2010 | Wright et al. |
| 2010/0036606 A1 | 2/2010 | Jones |
| 2010/0042498 A1 | 2/2010 | Schalk |
| 2010/0049397 A1 | 2/2010 | Liu et al. |
| 2010/0052945 A1 | 3/2010 | Breed |
| 2010/0057337 A1 | 3/2010 | Fuchs |
| 2010/0066498 A1 | 3/2010 | Fenton |
| 2010/0069115 A1 | 3/2010 | Liu |
| 2010/0070338 A1 | 3/2010 | Siotia et al. |
| 2010/0077094 A1 | 3/2010 | Howarter et al. |
| 2010/0087987 A1 | 4/2010 | Huang et al. |
| 2010/0090817 A1 | 4/2010 | Yamaguchi et al. |
| 2010/0097178 A1 | 4/2010 | Pisz et al. |
| 2010/0097239 A1 | 4/2010 | Campbell et al. |
| 2010/0097458 A1 | 4/2010 | Zhang et al. |
| 2010/0106344 A1 | 4/2010 | Edwards et al. |
| 2010/0106418 A1 | 4/2010 | Kindo et al. |
| 2010/0118025 A1 | 5/2010 | Smith et al. |
| 2010/0121570 A1 | 5/2010 | Tokue et al. |
| 2010/0121645 A1 | 5/2010 | Seitz et al. |
| 2010/0125387 A1 | 5/2010 | Sehyun et al. |
| 2010/0125405 A1 | 5/2010 | Chae et al. |
| 2010/0125811 A1 | 5/2010 | Moore et al. |
| 2010/0127847 A1 | 5/2010 | Evans et al. |
| 2010/0131300 A1 | 5/2010 | Collopy et al. |
| 2010/0134302 A1 | 6/2010 | Ahn et al. |
| 2010/0134958 A1 | 6/2010 | Disaverio et al. |
| 2010/0136944 A1 | 6/2010 | Taylor et al. |
| 2010/0137037 A1 | 6/2010 | Basir |
| 2010/0144284 A1 | 6/2010 | Chutorash et al. |
| 2010/0145700 A1 | 6/2010 | Kennewick et al. |
| 2010/0145987 A1 | 6/2010 | Harper et al. |
| 2010/0152976 A1 | 6/2010 | White et al. |
| 2010/0169432 A1 | 7/2010 | Santori et al. |
| 2010/0174474 A1 | 7/2010 | Nagase |
| 2010/0179712 A1 | 7/2010 | Pepitone et al. |
| 2010/0185341 A1 | 7/2010 | Wilson et al. |
| 2010/0188831 A1 | 7/2010 | Ortet |
| 2010/0197359 A1 | 8/2010 | Harris |
| 2010/0202346 A1 | 8/2010 | Sitzes et al. |
| 2010/0211259 A1 | 8/2010 | McClellan |
| 2010/0211282 A1 | 8/2010 | Nakata et al. |
| 2010/0211300 A1 | 8/2010 | Jaffe et al. |
| 2010/0211304 A1 | 8/2010 | Hwang et al. |
| 2010/0211441 A1 | 8/2010 | Sprigg et al. |
| 2010/0217458 A1 | 8/2010 | Schweiger et al. |
| 2010/0222939 A1 | 9/2010 | Namburu et al. |
| 2010/0228404 A1 | 9/2010 | Link et al. |
| 2010/0234071 A1 | 9/2010 | Shabtay et al. |
| 2010/0235042 A1 | 9/2010 | Ying |
| 2010/0235744 A1 | 9/2010 | Schultz |
| 2010/0235891 A1 | 9/2010 | Oglesbee et al. |
| 2010/0250071 A1 | 9/2010 | Pala et al. |
| 2010/0253493 A1 | 10/2010 | Szczerba et al. |
| 2010/0256836 A1 | 10/2010 | Mudalige |
| 2010/0265104 A1 | 10/2010 | Zlojutro |
| 2010/0268426 A1 | 10/2010 | Pathak et al. |
| 2010/0274410 A1 | 10/2010 | Tsien et al. |
| 2010/0280751 A1 | 11/2010 | Breed |
| 2010/0287303 A1 | 11/2010 | Smith et al. |
| 2010/0289632 A1 | 11/2010 | Seder et al. |
| 2010/0289643 A1 | 11/2010 | Trundle et al. |
| 2010/0291427 A1 | 11/2010 | Zhou |
| 2010/0295676 A1 | 11/2010 | Khachaturov et al. |
| 2010/0304640 A1 | 12/2010 | Sofman et al. |
| 2010/0305807 A1 | 12/2010 | Basir et al. |
| 2010/0306080 A1 | 12/2010 | Trandal et al. |
| 2010/0306309 A1 | 12/2010 | Santori et al. |
| 2010/0306435 A1 | 12/2010 | Nigoghoslan et al. |
| 2010/0315218 A1 | 12/2010 | Cades et al. |
| 2010/0321151 A1 | 12/2010 | Matsuura et al. |
| 2010/0325626 A1 | 12/2010 | Greschler et al. |
| 2010/0332130 A1 | 12/2010 | Shimizu et al. |
| 2011/0000961 A1 | 1/2011 | McNeal |
| 2011/0015853 A1 | 1/2011 | DeKock et al. |
| 2011/0018736 A1 | 1/2011 | Carr |
| 2011/0021213 A1 | 1/2011 | Carr |
| 2011/0021234 A1 | 1/2011 | Tibbits et al. |
| 2011/0028138 A1 | 2/2011 | Davies-Moore et al. |
| 2011/0032110 A1 | 2/2011 | Taguchi |
| 2011/0035098 A1 | 2/2011 | Goto et al. |
| 2011/0035141 A1 | 2/2011 | Barker et al. |
| 2011/0040438 A1 | 2/2011 | Kluge et al. |
| 2011/0050589 A1 | 3/2011 | Yan et al. |
| 2011/0053506 A1 | 3/2011 | Lemke et al. |
| 2011/0077808 A1 | 3/2011 | Hyde et al. |
| 2011/0078024 A1 | 3/2011 | Messier et al. |
| 2011/0080282 A1 | 4/2011 | Kleve et al. |
| 2011/0082615 A1 | 4/2011 | Small et al. |
| 2011/0084824 A1 | 4/2011 | Tewari et al. |
| 2011/0090078 A1 | 4/2011 | Kim et al. |
| 2011/0092159 A1 | 4/2011 | Park et al. |
| 2011/0093154 A1 | 4/2011 | Moinzadeh et al. |
| 2011/0093158 A1 | 4/2011 | Theisen et al. |
| 2011/0093438 A1 | 4/2011 | Poulsen |
| 2011/0093846 A1 | 4/2011 | Moinzadeh et al. |
| 2011/0105097 A1 | 5/2011 | Tadayon et al. |
| 2011/0106375 A1 | 5/2011 | Sundaram et al. |
| 2011/0112717 A1 | 5/2011 | Resner |
| 2011/0112969 A1 | 5/2011 | Zaid et al. |
| 2011/0117933 A1 | 5/2011 | Andersson |
| 2011/0119344 A1 | 5/2011 | Eustis |
| 2011/0130915 A1 | 6/2011 | Wright et al. |
| 2011/0134749 A1 | 6/2011 | Speks et al. |
| 2011/0137520 A1 | 6/2011 | Rector et al. |
| 2011/0145331 A1 | 6/2011 | Christie et al. |
| 2011/0172873 A1 | 7/2011 | Szwabowski et al. |
| 2011/0175754 A1 | 7/2011 | Karpinsky |
| 2011/0183658 A1 | 7/2011 | Zellner |
| 2011/0187520 A1 | 8/2011 | Filev et al. |
| 2011/0190972 A1 | 8/2011 | Timmons et al. |
| 2011/0193707 A1 | 8/2011 | Ngo |
| 2011/0193726 A1 | 8/2011 | Szwabowski et al. |
| 2011/0195699 A1 | 8/2011 | Tadayon et al. |
| 2011/0197187 A1 | 8/2011 | Roh |
| 2011/0205047 A1 | 8/2011 | Patel et al. |
| 2011/0209079 A1 | 8/2011 | Tarte et al. |
| 2011/0210867 A1 | 9/2011 | Benedikt |
| 2011/0212717 A1 | 9/2011 | Rhoads et al. |
| 2011/0213656 A1 | 9/2011 | Turner |
| 2011/0221656 A1 | 9/2011 | Haddick et al. |
| 2011/0224865 A1 | 9/2011 | Gordon et al. |
| 2011/0224898 A1 | 9/2011 | Scofield et al. |
| 2011/0225527 A1 | 9/2011 | Law et al. |
| 2011/0227757 A1 | 9/2011 | Chen et al. |
| 2011/0231091 A1 | 9/2011 | Gourlay et al. |
| 2011/0234369 A1 | 9/2011 | Cai et al. |
| 2011/0245999 A1 | 10/2011 | Kordonowy |
| 2011/0246210 A1 | 10/2011 | Matsur |
| 2011/0247013 A1 | 10/2011 | Feller et al. |
| 2011/0251734 A1 | 10/2011 | Schepp et al. |
| 2011/0257973 A1 | 10/2011 | Chutorash et al. |
| 2011/0267204 A1 | 11/2011 | Chuang et al. |
| 2011/0267205 A1 | 11/2011 | McClellan et al. |
| 2011/0286676 A1 | 11/2011 | El Dokor |
| 2011/0288765 A1 | 11/2011 | Conway |
| 2011/0291886 A1 | 12/2011 | Krieter |
| 2011/0291926 A1 | 12/2011 | Gokturk et al. |
| 2011/0298808 A1 | 12/2011 | Rovik |
| 2011/0301844 A1 | 12/2011 | Aono |
| 2011/0307354 A1 | 12/2011 | Erman et al. |
| 2011/0307570 A1 | 12/2011 | Speks |
| 2011/0309926 A1 | 12/2011 | Eikelenberg et al. |
| 2011/0309953 A1 | 12/2011 | Petite et al. |

(56) References Cited

U.S. PATENT DOCUMENTS

| | | |
|---|---|---|
| 2011/0313653 A1 | 12/2011 | Lindner |
| 2011/0320089 A1 | 12/2011 | Lewis |
| 2012/0006610 A1 | 1/2012 | Wallace et al. |
| 2012/0010807 A1 | 1/2012 | Zhou |
| 2012/0016581 A1 | 1/2012 | Mochizuki et al. |
| 2012/0029852 A1 | 2/2012 | Golf et al. |
| 2012/0030002 A1 | 2/2012 | Bous et al. |
| 2012/0030512 A1 | 2/2012 | Wadhwa et al. |
| 2012/0038489 A1 | 2/2012 | Goldshmidt |
| 2012/0046822 A1 | 2/2012 | Anderson |
| 2012/0047530 A1 | 2/2012 | Shkedi |
| 2012/0053793 A1 | 3/2012 | Sala et al. |
| 2012/0053888 A1 | 3/2012 | Stahlin et al. |
| 2012/0059789 A1 | 3/2012 | Sakai et al. |
| 2012/0065815 A1 | 3/2012 | Hess |
| 2012/0065834 A1 | 3/2012 | Senart |
| 2012/0068956 A1 | 3/2012 | Jira et al. |
| 2012/0071097 A1 | 3/2012 | Matsushita et al. |
| 2012/0072244 A1 | 3/2012 | Collins et al. |
| 2012/0074770 A1 | 3/2012 | Lee |
| 2012/0083947 A1 | 4/2012 | Anderson et al. |
| 2012/0083960 A1 | 4/2012 | Zhu et al. |
| 2012/0083971 A1 | 4/2012 | Preston |
| 2012/0084773 A1 | 4/2012 | Lee et al. |
| 2012/0089299 A1 | 4/2012 | Breed |
| 2012/0092251 A1 | 4/2012 | Hashimoto et al. |
| 2012/0101876 A1 | 4/2012 | Truvey et al. |
| 2012/0101914 A1 | 4/2012 | Kumar et al. |
| 2012/0105613 A1 | 5/2012 | Weng et al. |
| 2012/0106114 A1 | 5/2012 | Caron et al. |
| 2012/0109446 A1 | 5/2012 | Yousefi et al. |
| 2012/0109451 A1 | 5/2012 | Tan |
| 2012/0110356 A1 | 5/2012 | Yousefi et al. |
| 2012/0113822 A1 | 5/2012 | Letner |
| 2012/0115446 A1 | 5/2012 | Guatama et al. |
| 2012/0116609 A1 | 5/2012 | Jung et al. |
| 2012/0116678 A1 | 5/2012 | Witmer |
| 2012/0116696 A1 | 5/2012 | Wank |
| 2012/0146766 A1 | 6/2012 | Geisler et al. |
| 2012/0146809 A1 | 6/2012 | Oh et al. |
| 2012/0149341 A1 | 6/2012 | Tadayon et al. |
| 2012/0150651 A1 | 6/2012 | Hoffberg et al. |
| 2012/0155636 A1 | 6/2012 | Muthaiah |
| 2012/0158436 A1 | 6/2012 | Bauer et al. |
| 2012/0173135 A1 | 7/2012 | Gutman |
| 2012/0173900 A1 | 7/2012 | Diab et al. |
| 2012/0173905 A1 | 7/2012 | Diab et al. |
| 2012/0179325 A1 | 7/2012 | Faenger |
| 2012/0179547 A1 | 7/2012 | Besore et al. |
| 2012/0188876 A1 | 7/2012 | Chow et al. |
| 2012/0197523 A1 | 8/2012 | Kirsch |
| 2012/0197669 A1 | 8/2012 | Kote et al. |
| 2012/0204166 A1 | 8/2012 | Ichihara |
| 2012/0210160 A1 | 8/2012 | Fuhrman |
| 2012/0215375 A1 | 8/2012 | Chang |
| 2012/0217928 A1 | 8/2012 | Kulidjian |
| 2012/0218125 A1 | 8/2012 | Demirdjian et al. |
| 2012/0226413 A1 | 9/2012 | Chen et al. |
| 2012/0238286 A1 | 9/2012 | Mallavarapu et al. |
| 2012/0239242 A1 | 9/2012 | Uehara |
| 2012/0242510 A1 | 9/2012 | Choi et al. |
| 2012/0254763 A1 | 10/2012 | Protopapas et al. |
| 2012/0254804 A1 | 10/2012 | Shema et al. |
| 2012/0259951 A1 | 10/2012 | Schalk et al. |
| 2012/0265359 A1 | 10/2012 | Das |
| 2012/0269432 A1 | 10/2012 | Wang et al. |
| 2012/0274459 A1 | 11/2012 | Jaisimha et al. |
| 2012/0274481 A1 | 11/2012 | Ginsberg et al. |
| 2012/0284292 A1 | 11/2012 | Rechsteiner et al. |
| 2012/0289217 A1 | 11/2012 | Reimer et al. |
| 2012/0289253 A1 | 11/2012 | Haag et al. |
| 2012/0296567 A1 | 11/2012 | Breed |
| 2012/0313771 A1 | 12/2012 | Wottlifff, III |
| 2012/0316720 A1 | 12/2012 | Hyde et al. |
| 2012/0317561 A1 | 12/2012 | Aslam et al. |
| 2012/0323413 A1 | 12/2012 | Kedar-Dongarkar et al. |
| 2012/0327231 A1 | 12/2012 | Cochran et al. |
| 2013/0005263 A1 | 1/2013 | Sakata |
| 2013/0005414 A1 | 1/2013 | Bindra et al. |
| 2013/0013157 A1 | 1/2013 | Kim et al. |
| 2013/0015814 A1 | 1/2013 | Kelty et al. |
| 2013/0019252 A1 | 1/2013 | Haase et al. |
| 2013/0024060 A1 | 1/2013 | Sukkarie et al. |
| 2013/0030645 A1 | 1/2013 | Divine et al. |
| 2013/0030811 A1 | 1/2013 | Olleon et al. |
| 2013/0031540 A1 | 1/2013 | Throop et al. |
| 2013/0031541 A1 | 1/2013 | Wilks et al. |
| 2013/0035063 A1 | 2/2013 | Fisk et al. |
| 2013/0046624 A1 | 2/2013 | Caiman |
| 2013/0050069 A1 | 2/2013 | Ota |
| 2013/0055096 A1 | 2/2013 | Kim et al. |
| 2013/0059607 A1 | 3/2013 | Herz et al. |
| 2013/0063336 A1 | 3/2013 | Sugimoto et al. |
| 2013/0066512 A1 | 3/2013 | Willard et al. |
| 2013/0067599 A1 | 3/2013 | Raje et al. |
| 2013/0075530 A1 | 3/2013 | Shander et al. |
| 2013/0079964 A1 | 3/2013 | Sukkarie et al. |
| 2013/0083805 A1 | 4/2013 | Lu et al. |
| 2013/0085787 A1 | 4/2013 | Gore et al. |
| 2013/0086164 A1 | 4/2013 | Wheeler et al. |
| 2013/0099915 A1 | 4/2013 | Prasad et al. |
| 2013/0103196 A1 | 4/2013 | Monceaux et al. |
| 2013/0105264 A1 | 5/2013 | Ruth et al. |
| 2013/0116882 A1 | 5/2013 | Link et al. |
| 2013/0116915 A1 | 5/2013 | Ferreira et al. |
| 2013/0134730 A1 | 5/2013 | Ricci |
| 2013/0135118 A1 | 5/2013 | Ricci |
| 2013/0138591 A1 | 5/2013 | Ricci |
| 2013/0138714 A1 | 5/2013 | Ricci |
| 2013/0139140 A1 | 5/2013 | Rao et al. |
| 2013/0141247 A1 | 6/2013 | Ricci |
| 2013/0141252 A1 | 6/2013 | Ricci |
| 2013/0143495 A1 | 6/2013 | Ricci |
| 2013/0143546 A1 | 6/2013 | Ricci |
| 2013/0143601 A1 | 6/2013 | Ricci |
| 2013/0144459 A1 | 6/2013 | Ricci |
| 2013/0144460 A1 | 6/2013 | Ricci |
| 2013/0144461 A1 | 6/2013 | Ricci |
| 2013/0144462 A1 | 6/2013 | Ricci |
| 2013/0144463 A1 | 6/2013 | Ricci et al. |
| 2013/0144469 A1 | 6/2013 | Ricci |
| 2013/0144470 A1 | 6/2013 | Ricci |
| 2013/0144474 A1 | 6/2013 | Ricci |
| 2013/0144486 A1 | 6/2013 | Ricci |
| 2013/0144520 A1 | 6/2013 | Ricci |
| 2013/0144657 A1 | 6/2013 | Ricci |
| 2013/0145065 A1 | 6/2013 | Ricci |
| 2013/0145279 A1 | 6/2013 | Ricci |
| 2013/0145297 A1 | 6/2013 | Ricci et al. |
| 2013/0145360 A1 | 6/2013 | Ricci |
| 2013/0145401 A1 | 6/2013 | Ricci |
| 2013/0145482 A1 | 6/2013 | Ricci et al. |
| 2013/0147638 A1 | 6/2013 | Ricci |
| 2013/0151031 A1 | 6/2013 | Ricci |
| 2013/0151065 A1 | 6/2013 | Ricci |
| 2013/0151088 A1 | 6/2013 | Ricci |
| 2013/0151288 A1 | 6/2013 | Bowne et al. |
| 2013/0152003 A1 | 6/2013 | Ricci et al. |
| 2013/0154298 A1 | 6/2013 | Ricci |
| 2013/0157640 A1 | 6/2013 | Aycock |
| 2013/0157647 A1 | 6/2013 | Koiodziej |
| 2013/0158778 A1 | 6/2013 | Tengler et al. |
| 2013/0158821 A1 | 6/2013 | Ricci |
| 2013/0166096 A1 | 6/2013 | Jotanovic |
| 2013/0166097 A1 | 6/2013 | Ricci |
| 2013/0166098 A1 | 6/2013 | Lavie et al. |
| 2013/0166109 A1 | 6/2013 | Ginsberg |
| 2013/0166152 A1 | 6/2013 | Butterworth |
| 2013/0166208 A1 | 6/2013 | Forstall et al. |
| 2013/0167159 A1 | 6/2013 | Ricci et al. |
| 2013/0173531 A1 | 7/2013 | Rinearson et al. |
| 2013/0179057 A1 | 7/2013 | Fisher et al. |
| 2013/0179689 A1 | 7/2013 | Matsumoto et al. |
| 2013/0190978 A1 | 7/2013 | Kato et al. |

(56) References Cited

U.S. PATENT DOCUMENTS

| | | |
|---|---|---|
| 2013/0194108 A1 | 8/2013 | Lapiotis et al. |
| 2013/0197796 A1 | 8/2013 | Obradovich et al. |
| 2013/0197797 A1 | 8/2013 | Boddy et al. |
| 2013/0198031 A1 | 8/2013 | Mitchell et al. |
| 2013/0198737 A1 | 8/2013 | Ricci |
| 2013/0198802 A1 | 8/2013 | Ricci |
| 2013/0200991 A1 | 8/2013 | Ricci et al. |
| 2013/0203400 A1 | 8/2013 | Ricci |
| 2013/0204455 A1 | 8/2013 | Chia et al. |
| 2013/0204457 A1 | 8/2013 | King |
| 2013/0204466 A1 | 8/2013 | Ricci |
| 2013/0204484 A1 | 8/2013 | Ricci |
| 2013/0204493 A1 | 8/2013 | Ricci et al. |
| 2013/0204943 A1 | 8/2013 | Ricci |
| 2013/0205026 A1 | 8/2013 | Ricci |
| 2013/0205412 A1 | 8/2013 | Ricci |
| 2013/0207794 A1 | 8/2013 | Patel et al. |
| 2013/0212065 A1 | 8/2013 | Rahnama |
| 2013/0212659 A1 | 8/2013 | Maher et al. |
| 2013/0215116 A1 | 8/2013 | Siddique et al. |
| 2013/0218412 A1 | 8/2013 | Ricci |
| 2013/0218445 A1 | 8/2013 | Basir |
| 2013/0219039 A1 | 8/2013 | Ricci |
| 2013/0226365 A1 | 8/2013 | Brozovich |
| 2013/0226371 A1 | 8/2013 | Rovik et al. |
| 2013/0226392 A1 | 8/2013 | Schneider et al. |
| 2013/0226449 A1 | 8/2013 | Rovik et al. |
| 2013/0226622 A1 | 8/2013 | Adamson et al. |
| 2013/0227648 A1 | 8/2013 | Ricci |
| 2013/0231784 A1 | 9/2013 | Rovik et al. |
| 2013/0231800 A1 | 9/2013 | Ricci |
| 2013/0232142 A1 | 9/2013 | Nielsen et al. |
| 2013/0238165 A1 | 9/2013 | Garrett et al. |
| 2013/0241720 A1 | 9/2013 | Ricci et al. |
| 2013/0245882 A1 | 9/2013 | Ricci |
| 2013/0250933 A1 | 9/2013 | Yousefi et al. |
| 2013/0261871 A1 | 10/2013 | Hobbs et al. |
| 2013/0261966 A1 | 10/2013 | Wang et al. |
| 2013/0265178 A1 | 10/2013 | Tengler et al. |
| 2013/0274997 A1 | 10/2013 | Chien |
| 2013/0279111 A1 | 10/2013 | Lee |
| 2013/0279491 A1 | 10/2013 | Rubin et al. |
| 2013/0282238 A1 | 10/2013 | Ricci et al. |
| 2013/0282357 A1 | 10/2013 | Rubin et al. |
| 2013/0282946 A1 | 10/2013 | Ricci |
| 2013/0288606 A1 | 10/2013 | Kirsch |
| 2013/0293364 A1 | 11/2013 | Ricci et al. |
| 2013/0293452 A1 | 11/2013 | Ricci et al. |
| 2013/0293480 A1 | 11/2013 | Kritt et al. |
| 2013/0295901 A1 | 11/2013 | Abramson et al. |
| 2013/0295908 A1 | 11/2013 | Zeinstra et al. |
| 2013/0295913 A1 | 11/2013 | Matthews et al. |
| 2013/0297195 A1 | 11/2013 | Das et al. |
| 2013/0300554 A1 | 11/2013 | Braden |
| 2013/0301584 A1 | 11/2013 | Addepalli et al. |
| 2013/0304371 A1 | 11/2013 | Kitatani et al. |
| 2013/0308265 A1 | 11/2013 | Arnouse |
| 2013/0309977 A1 | 11/2013 | Heines et al. |
| 2013/0311038 A1 | 11/2013 | Kim et al. |
| 2013/0325453 A1 | 12/2013 | Levien et al. |
| 2013/0325568 A1 | 12/2013 | Mangalvedkar et al. |
| 2013/0329372 A1 | 12/2013 | Wilkins |
| 2013/0332023 A1 | 12/2013 | Bertosa et al. |
| 2013/0338914 A1 | 12/2013 | Weiss |
| 2013/0339027 A1 | 12/2013 | Dokor et al. |
| 2013/0345929 A1 | 12/2013 | Bowden et al. |
| 2014/0021915 A1 | 1/2014 | Staley et al. |
| 2014/0028542 A1 | 1/2014 | Lovitt et al. |
| 2014/0032014 A1 | 1/2014 | DeBiasio et al. |
| 2014/0054957 A1 | 2/2014 | Bellis |
| 2014/0058672 A1 | 2/2014 | Wansley et al. |
| 2014/0066014 A1 | 3/2014 | Nicholson et al. |
| 2014/0067201 A1 | 3/2014 | Visintainer et al. |
| 2014/0067564 A1 | 3/2014 | Yuan |
| 2014/0070917 A1 | 3/2014 | Protopapas |
| 2014/0081544 A1 | 3/2014 | Fry |
| 2014/0088798 A1 | 3/2014 | Himmelstein |
| 2014/0096068 A1 | 4/2014 | Dewan et al. |
| 2014/0097955 A1 | 4/2014 | Lovitt et al. |
| 2014/0109075 A1 | 4/2014 | Hoffman et al. |
| 2014/0109080 A1 | 4/2014 | Ricci |
| 2014/0120829 A1 | 5/2014 | Bhamidipatl et al. |
| 2014/0121862 A1 | 5/2014 | Zarrella et al. |
| 2014/0125485 A1 | 5/2014 | Juhasz |
| 2014/0125802 A1 | 5/2014 | Beckert et al. |
| 2014/0143839 A1 | 5/2014 | Ricci |
| 2014/0156133 A1 | 6/2014 | Cullinane et al. |
| 2014/0164611 A1 | 6/2014 | Motettiere et al. |
| 2014/0168062 A1 | 6/2014 | Katz et al. |
| 2014/0168436 A1 | 6/2014 | Pedicino |
| 2014/0169621 A1 | 6/2014 | Burr |
| 2014/0171752 A1 | 6/2014 | Park et al. |
| 2014/0172290 A1 | 6/2014 | Prokhorov et al. |
| 2014/0172727 A1 | 6/2014 | Abhyanker et al. |
| 2014/0188533 A1 | 7/2014 | Davidson |
| 2014/0195272 A1 | 7/2014 | Sadiq et al. |
| 2014/0198216 A1 | 7/2014 | Zhal et al. |
| 2014/0200737 A1 | 7/2014 | Lortz et al. |
| 2014/0207328 A1 | 7/2014 | Wolf et al. |
| 2014/0220966 A1 | 8/2014 | Muetzel et al. |
| 2014/0222298 A1 | 8/2014 | Gurin |
| 2014/0223384 A1 | 8/2014 | Graumann |
| 2014/0240089 A1 | 8/2014 | Chang |
| 2014/0244078 A1 | 8/2014 | Downey et al. |
| 2014/0244096 A1 | 8/2014 | An et al. |
| 2014/0244111 A1 | 8/2014 | Gross et al. |
| 2014/0244156 A1 | 8/2014 | Magnusson et al. |
| 2014/0245277 A1 | 8/2014 | Petro et al. |
| 2014/0245278 A1 | 8/2014 | Zellen |
| 2014/0245284 A1 | 8/2014 | Alrabady et al. |
| 2014/0252091 A1 | 9/2014 | Morse et al. |
| 2014/0257627 A1 | 9/2014 | Hagan, Jr. |
| 2014/0267035 A1 | 9/2014 | Schalk et al. |
| 2014/0277936 A1 | 9/2014 | El Dokor et al. |
| 2014/0278070 A1 | 9/2014 | McGavran et al. |
| 2014/0278071 A1 | 9/2014 | San Filippo et al. |
| 2014/0278086 A1 | 9/2014 | San Filippo et al. |
| 2014/0281971 A1 | 9/2014 | Isbell, III et al. |
| 2014/0282161 A1 | 9/2014 | Cash |
| 2014/0282278 A1 | 9/2014 | Anderson et al. |
| 2014/0282470 A1 | 9/2014 | Buga et al. |
| 2014/0282931 A1 | 9/2014 | Protopapas |
| 2014/0292545 A1 | 10/2014 | Nemoto |
| 2014/0292665 A1 | 10/2014 | Lathrop et al. |
| 2014/0303899 A1 | 10/2014 | Fung |
| 2014/0306799 A1 | 10/2014 | Ricci |
| 2014/0306814 A1 | 10/2014 | Ricci |
| 2014/0306817 A1 | 10/2014 | Ricci |
| 2014/0306826 A1 | 10/2014 | Ricci |
| 2014/0306833 A1 | 10/2014 | Ricci |
| 2014/0306834 A1 | 10/2014 | Ricci |
| 2014/0306835 A1 | 10/2014 | Ricci |
| 2014/0307655 A1 | 10/2014 | Ricci |
| 2014/0307724 A1 | 10/2014 | Ricci |
| 2014/0308902 A1 | 10/2014 | Ricci |
| 2014/0309789 A1 | 10/2014 | Ricci |
| 2014/0309790 A1 | 10/2014 | Ricci |
| 2014/0309804 A1 | 10/2014 | Ricci |
| 2014/0309805 A1 | 10/2014 | Ricci |
| 2014/0309806 A1 | 10/2014 | Ricci |
| 2014/0309813 A1 | 10/2014 | Ricci |
| 2014/0309814 A1 | 10/2014 | Ricci et al. |
| 2014/0309815 A1 | 10/2014 | Ricci et al. |
| 2014/0309838 A1 | 10/2014 | Ricci |
| 2014/0309839 A1 | 10/2014 | Ricci et al. |
| 2014/0309847 A1 | 10/2014 | Ricci |
| 2014/0309849 A1 | 10/2014 | Ricci |
| 2014/0309852 A1 | 10/2014 | Ricci |
| 2014/0309853 A1 | 10/2014 | Ricci |
| 2014/0309862 A1 | 10/2014 | Ricci |
| 2014/0309863 A1 | 10/2014 | Ricci |
| 2014/0309864 A1 | 10/2014 | Ricci |
| 2014/0309865 A1 | 10/2014 | Ricci |
| 2014/0309866 A1 | 10/2014 | Ricci |

(56) References Cited

U.S. PATENT DOCUMENTS

| | | |
|---|---|---|
| 2014/0309867 A1 | 10/2014 | Ricci |
| 2014/0309868 A1 | 10/2014 | Ricci |
| 2014/0309869 A1 | 10/2014 | Ricci |
| 2014/0309870 A1 | 10/2014 | Ricci et al. |
| 2014/0309871 A1 | 10/2014 | Ricci |
| 2014/0309872 A1 | 10/2014 | Ricci |
| 2014/0309873 A1 | 10/2014 | Ricci |
| 2014/0309874 A1 | 10/2014 | Ricci |
| 2014/0309875 A1 | 10/2014 | Ricci |
| 2014/0309876 A1 | 10/2014 | Ricci |
| 2014/0309877 A1 | 10/2014 | Ricci |
| 2014/0309878 A1 | 10/2014 | Ricci |
| 2014/0309879 A1 | 10/2014 | Ricci |
| 2014/0309880 A1 | 10/2014 | Ricci |
| 2014/0309885 A1 | 10/2014 | Ricci |
| 2014/0309886 A1 | 10/2014 | Ricci |
| 2014/0309891 A1 | 10/2014 | Ricci |
| 2014/0309892 A1 | 10/2014 | Ricci |
| 2014/0309893 A1 | 10/2014 | Ricci |
| 2014/0309913 A1 | 10/2014 | Ricci et al. |
| 2014/0309919 A1 | 10/2014 | Ricci |
| 2014/0309920 A1 | 10/2014 | Ricci |
| 2014/0309921 A1 | 10/2014 | Ricci et al. |
| 2014/0309922 A1 | 10/2014 | Ricci |
| 2014/0309923 A1 | 10/2014 | Ricci |
| 2014/0309927 A1 | 10/2014 | Ricci |
| 2014/0309929 A1 | 10/2014 | Ricci |
| 2014/0309930 A1 | 10/2014 | Ricci |
| 2014/0309934 A1 | 10/2014 | Ricci |
| 2014/0309935 A1 | 10/2014 | Ricci |
| 2014/0309982 A1 | 10/2014 | Ricci |
| 2014/0310031 A1 | 10/2014 | Ricci |
| 2014/0310075 A1 | 10/2014 | Ricci |
| 2014/0310103 A1 | 10/2014 | Ricci |
| 2014/0310186 A1 | 10/2014 | Ricci |
| 2014/0310277 A1 | 10/2014 | Ricci |
| 2014/0310379 A1 | 10/2014 | Ricci et al. |
| 2014/0310594 A1 | 10/2014 | Ricci et al. |
| 2014/0310610 A1 | 10/2014 | Ricci |
| 2014/0310702 A1 | 10/2014 | Ricci et al. |
| 2014/0310739 A1 | 10/2014 | Ricci et al. |
| 2014/0310788 A1 | 10/2014 | Ricci |
| 2014/0322676 A1 | 10/2014 | Raman |
| 2014/0347207 A1 | 11/2014 | Zeng et al. |
| 2014/0347265 A1 | 11/2014 | Allen et al. |
| 2015/0007155 A1 | 1/2015 | Hoffman et al. |
| 2015/0012186 A1 | 1/2015 | Horseman |
| 2015/0032366 A1 | 1/2015 | Man et al. |
| 2015/0032670 A1 | 1/2015 | Brazell |
| 2015/0057839 A1 | 2/2015 | Chang et al. |
| 2015/0061895 A1 | 3/2015 | Ricci |
| 2015/0066284 A1 | 3/2015 | Yopp |
| 2015/0081133 A1 | 3/2015 | Schulz |
| 2015/0081167 A1 | 3/2015 | Pisz et al. |
| 2015/0088423 A1 | 3/2015 | Tuukkanen |
| 2015/0088515 A1 | 3/2015 | Beaumont et al. |
| 2015/0116200 A1 | 4/2015 | Kurosawa et al. |
| 2015/0158499 A1 | 6/2015 | Koravadi |
| 2015/0178034 A1 | 6/2015 | Penilla et al. |
| 2015/0233720 A1 | 8/2015 | Harada |
| 2015/0235480 A1 | 8/2015 | Cudak et al. |
| 2015/0241233 A1 | 8/2015 | Loftus et al. |
| 2015/0294329 A1 | 10/2015 | Salto et al. |
| 2015/0298565 A1 | 10/2015 | Iwamura et al. |
| 2015/0343918 A1 | 12/2015 | Watanabe et al. |
| 2015/0345971 A1 | 12/2015 | Meuleau et al. |
| 2016/0003637 A1 | 1/2016 | Andersen |
| 2016/0008985 A1 | 1/2016 | Kim et al. |
| 2016/0009291 A1 | 1/2016 | Pallett et al. |
| 2016/0009295 A1 | 1/2016 | Chun et al. |
| 2016/0009391 A1 | 1/2016 | Friesel |
| 2016/0026182 A1 | 1/2016 | Boroditsky et al. |
| 2016/0031441 A1 | 2/2016 | Foley |
| 2016/0046288 A1 | 2/2016 | Pawlicki et al. |
| 2016/0059856 A1 | 3/2016 | Van Dan Elzen et al. |
| 2016/0061612 A1 | 3/2016 | You et al. |
| 2016/0070527 A1 | 3/2016 | Ricci |
| 2016/0086391 A1 | 3/2016 | Ricci |
| 2016/0129908 A1 | 5/2016 | Harda |
| 2016/0161272 A1 | 6/2016 | Shigezumi et al. |
| 2016/0202074 A1 | 7/2016 | Woodard et al. |
| 2016/0221573 A1 | 8/2016 | Prokhorov |
| 2016/0269456 A1 | 9/2016 | Ricci |
| 2016/0269469 A1 | 9/2016 | Ricci |
| 2016/0273927 A1 | 9/2016 | Kitajima et al. |
| 2016/0276854 A1 | 9/2016 | Lian |
| 2016/0334236 A1 | 11/2016 | Mason et al. |
| 2016/0355192 A1 | 12/2016 | James et al. |
| 2016/0368396 A1 | 12/2016 | Konet et al. |
| 2016/0368491 A1 | 12/2016 | Hauler et al. |
| 2016/0375788 A1 | 12/2016 | Liu |
| 2017/0008523 A1 | 1/2017 | Christensen et al. |
| 2017/0015288 A1 | 1/2017 | Coelingh et al. |
| 2017/0021837 A1 | 1/2017 | Ebina |
| 2017/0030728 A1 | 2/2017 | Baglino et al. |
| 2017/0036673 A1 | 2/2017 | Lee |
| 2017/0053538 A1 | 2/2017 | Samarasekera et al. |
| 2017/0057507 A1 | 3/2017 | Gordon et al. |
| 2017/0057542 A1 | 3/2017 | Kim et al. |
| 2017/0076455 A1 | 3/2017 | Newman et al. |
| 2017/0087999 A1 | 3/2017 | Miller et al. |
| 2017/0088000 A1 | 3/2017 | Payne et al. |
| 2017/0088117 A1 | 3/2017 | Ogawa |
| 2017/0143246 A1 | 5/2017 | Flickinger |
| 2017/0212515 A1 | 7/2017 | Bertollini et al. |
| 2017/0242442 A1 | 8/2017 | Minster |
| 2017/0267256 A1 | 9/2017 | Minster et al. |
| 2017/0291615 A1 | 10/2017 | Kusano et al. |
| 2017/0294000 A1 | 10/2017 | Shen et al. |
| 2017/0307392 A1 | 10/2017 | Kitajima et al. |
| 2017/0328716 A1 | 11/2017 | Ma |
| 2017/0349045 A1 | 12/2017 | McNew |
| 2017/0349185 A1 | 12/2017 | McNew |
| 2017/0355377 A1 | 12/2017 | Vijaya Kumar et al. |
| 2018/0052463 A1 | 2/2018 | Mays |
| 2018/0066957 A1 | 3/2018 | Stroila et al. |
| 2018/0082213 A1 | 3/2018 | McCord |
| 2018/0109482 A1 | 4/2018 | DeLuca et al. |
| 2018/0113450 A1 | 4/2018 | Sherony |
| 2018/0118219 A1 | 5/2018 | Hiei et al. |
| 2018/0120123 A1 | 5/2018 | Seok et al. |
| 2018/0127001 A1 | 5/2018 | Ricci |
| 2018/0143029 A1 | 5/2018 | Nikulin et al. |
| 2018/0151064 A1 | 5/2018 | Xu et al. |
| 2018/0170382 A1 | 6/2018 | Soliman et al. |
| 2018/0202825 A1 | 7/2018 | You et al. |
| 2018/0208209 A1 | 7/2018 | Al-Dahle et al. |
| 2018/0276351 A1* | 9/2018 | Patton ............... G06F 21/6218 |
| 2018/0293466 A1 | 10/2018 | Viswanathan |
| 2018/0373268 A1 | 12/2018 | Antunes Marques Esteves |
| 2019/0004526 A1 | 1/2019 | Soliman |
| 2019/0012909 A1* | 1/2019 | Mintz ................. G08G 1/0112 |
| 2019/0017828 A1 | 1/2019 | Harish et al. |
| 2019/0031037 A1 | 1/2019 | Fendt |
| 2019/0080142 A1 | 3/2019 | Abeywardena et al. |
| 2019/0107406 A1 | 4/2019 | Cox et al. |
| 2019/0141480 A1 | 5/2019 | Tung et al. |
| 2019/0186939 A1 | 6/2019 | Cox et al. |
| 2019/0226851 A1 | 7/2019 | Nicosevici et al. |
| 2019/0286793 A1* | 9/2019 | Patton .................... H04L 51/52 |
| 2020/0225661 A1 | 7/2020 | Guo et al. |
| 2020/0234582 A1* | 7/2020 | Mintz ............. G08G 1/096811 |

FOREIGN PATENT DOCUMENTS

| | | |
|---|---|---|
| CN | 101303878 | 11/2008 |
| CN | 102467827 | 5/2012 |
| EP | 1223567 | 7/2002 |
| EP | 1484729 | 12/2004 |
| EP | 2192015 | 6/2010 |
| JP | 2004-284450 | 10/2004 |
| KR | 2006-0128484 | 12/2006 |
| WO | WO 2007/126204 | 11/2007 |
| WO | WO 2012/102879 | 8/2012 |

(56) References Cited

FOREIGN PATENT DOCUMENTS

| | | |
|---|---|---|
| WO | WO 2013/074866 | 5/2013 |
| WO | WO 2013/074867 | 5/2013 |
| WO | WO 2013/074868 | 5/2013 |
| WO | WO 2013/074897 | 5/2013 |
| WO | WO 2013/074899 | 5/2013 |
| WO | WO 2013/074901 | 5/2013 |
| WO | WO 2013/074919 | 5/2013 |
| WO | WO 2013/074981 | 5/2013 |
| WO | WO 2013/074983 | 5/2013 |
| WO | WO 2013/075005 | 5/2013 |
| WO | WO 2013/181310 | 12/2013 |
| WO | WO 2014/014862 | 1/2014 |
| WO | WO 2014/139821 | 9/2014 |
| WO | WO 2014/143563 | 9/2014 |
| WO | WO 2014/158667 | 10/2014 |
| WO | WO 2014/158672 | 10/2014 |
| WO | WO 2014/158766 | 10/2014 |
| WO | WO 2014/172312 | 10/2014 |
| WO | WO 2014/172313 | 10/2014 |
| WO | WO 2014/172316 | 10/2014 |
| WO | WO 2014/172320 | 10/2014 |
| WO | WO 2014/172322 | 10/2014 |
| WO | WO 2014/172323 | 10/2014 |
| WO | WO 2014/172327 | 10/2014 |
| WO | WO 2016/035268 | 3/2016 |
| WO | WO 2016/062730 | 4/2016 |
| WO | WO 2016/145073 | 9/2016 |
| WO | WO 2016/145100 | 9/2016 |
| WO | WO 2017/167790 | 10/2017 |

OTHER PUBLICATIONS

Decision on Appeal for U.S. Appl. No. 15/727,838, dated May 5, 2022 15 pages.
Official Action for U.S. Appl. No. 16/826,873, dated Apr. 28, 2022, 16 pages.
U.S. Appl. No. 61/567,962, filed Dec. 7, 2011, Baarman et al.
"Carpool, HOV, Transit lanes," WazeWiki, 2016, retrieved from https://wiki.waze.com/wiki/Carpool,_HOV,_Transit_lanes, retrieved on Feb. 27, 2018, 3 pages.
"Managing Demand Through Travel Information Services," U.S. Department of Transportation brochure, FHWA, retrieved from http://www.ops.fhwa.dot.gov/pubiications/manag_demand_tis/travelinfo.htm, retrieved on Feb. 28, 2018, 30 pages.
"Nexus 10 Guidebook for Android," Google Inc., ©2012, Edition 1.2, 166 pages.
"ORB (Oriented FAST and Rotated BRIEF)", Open CV 3.0.0-dev documentation, retrieved from https://docs.opencv.org/3.0-beta/doc/py_tutorials/py_feature2d/py_orb/py_orb.html, 2014, 3 pages.
"Self-Driving: Self-Driving Autonomous Cars," available at http://www.automotivetechnologies.com/autonomous-self-driving-cars, accessed Dec. 2016, 9 pages.
"Softmaxfunction," Wikipedia, retrieved from https://en.wikipedia.org/wiki/Softmax_function, retrieved on Feb. 28, 2018, 4 pages.
Amor-Segan et al., "Towards the Self Healing Vehicle," Automotive Electronics, Jun. 2007, 2007 3rd Institution of Engineering and Technology Conference, 7 pages.
Badino et al., "Real-Time Topometric Localization," IEEE International Conference, Robotics and Automation, 2012, 8 pages.
Bennett, "Meet Samsung's Version of Apple AirPlay," CNET.com, Oct. 10, 2012, 11 pages.
Brubaker et al., "Lost! Leveraging the Crowd for Probabilistic Visual Self-Localization," Proceedings of the IEEE Conference on Computer Vision and Pattern Recognition, 2013, 8 pages.
Cairnie et al., "Using Finger-Pointing to Operate Secondary Controls in Automobiles," Proceedings of the IEEE Intelligent Vehicles Symposium 2000, Oct. 3-5, 2000, 6 pages.
Cathy et al., "A prescription fortransit arrival/departure prediction using automatic vehicle location data," Transportation Research Part C, 2003, vol. 11, pp. 241-264.

Clark, "How Self-Driving Cars Work: The Nuts and Bolts Behind Google's Autonomous Car Program," Feb. 21, 2015, available at http://www.makeuseof.com/tag/how-self-driving-cars-work-the-nuts-and-bolts-behind-googles-autonomous-car-program/, 9 pages.
Davies, "This NIO EP9 performance EV wants to be the Tesla of Supercars," SlashGear, 2016, retrieved from https//www.slashgear.com/nextev-nio-ep9-car-tesla-of-performance-evs-21464829, 9 pages.
Deaton et al., "How Driverless Cars Will Work," Jul. 1, 2008, HowStuffWorks.com. <http://auto.howstuftworks.com/under-the-hood/trends-innovations/driverless-car.htm> Sep. 18, 2017, 10 pages.
Dellaert et al., "Monte Carlo Localization for Mobile Robots," IEEE, Robotics and Automation, 1999 Proceedings, vol. 2, pp. 1322-1328.
Dumbaugh, "Safe Streets, Livable Streets: A Positive Approach to urban Roadside Design," Ph.D. dissertation for School of Civil & Environ. Engr., Georgia Inst. of Technology, Dec. 2005, 235 pages.
Engel et al., "LSD-SLAM: Large-Scale Direct Monocular SLAM," Springer, Cham., European Conference, 2014, Computer Vision, pp. 834-849, 16 pages.
Fei et al., "A QoS-aware Dynamic Bandwidth Allocation Algorithm for Relay Stations in IEEE 802.16j-based Vehicular Networks," Proceedings of the 2010 IEEE Global Telecommunications Conference, Dec. 10, 2010, 6 pages.
Floros et al., "OpenStreetSLAM: Global Vehicle Localization Using OpenStreetMaps," RWTH Aachen University, Computer Vision Group, 2013, 20 pages.
Galvez-Lopez et al., "Bags of Binary Words for Fast Place Recognition in Image Sequences," IEEE Transactions on Robotics, 2012, vol. 28(5), pp. 1188-1197, abstract only, 1 page.
Ge et al., "Optimal Relay Selection in IEEE 802.16 Multihop Relay Vehicular Networks," IEEE Transactions on Vehicular Technology, 2010, vol. 59(5), pp. 2198-2206.
Grana, et al., "A Fast Approach for Integrating ORB Descriptors in the Bag of Words Model," Proceedings of SPIE—The International Society for Optical Engineering, Feb. 2013, vol. 8667, pp. 86670-866709, DOI: 10.1117/12.2008460, 9 pages.
Grauman et al., "Excerpt chapter from Synthesis lecture draft: Visual Recognition," 2012, retrieved from http://www.cs.utexas.edu/~grauman/courses/fall2009/papers/bag_of_visual_words.pdr, 8 pages.
Guizzo, "How Google's Self-Driving Car Works," Oct. 18, 2011, available at https://spectrum.ieee.org/automaton/robotics/artificial-intelligence/how-google-self-driving-car-works, 5 pages.
Haklay et al., "OpenStreetMap: User-Generated Street Maps," IEEE Pervasive Computing, 2008, pp. 12-18.
Hays et al., "IM2GPS: estimating geographic information from a single image," IEEE Conference, Computer Vision and Pattern Recognition, 2008, pp. 1-8.
Heer et al.. "ALPHA: An Adaptive and Lightweight Protocol for Hop-by-hop Authentication," Proceedings of CoNEXT 2008, Dec. 2008, pp. 1-12.
Jahnich et al., "Towards a Middleware Approach for a Self-Configurable Automotive Embedded System," International Federation for Information Processing, 2008, pp. 55-65.
Kautonen, "NextEV unveils the NIO EP9 electric supercar in London," Autoblog, 2016, retrieved from http://www.autoblog.com/2016/11/21/nextev-unveiles-the-nio-ep9-electric-supercar-in-london/, 3 pages.
Kneip et al., "Robust Real-Time Visual Odometry with a Single Camera and an IMU," Proceedings of the British Machine Vision Conference, 2011, 11 pages.
Konolige et al., "Large-Scale Visual Odometry for Rough Terrain," Robotics Research, 2010, pp. 201-212, 12 pages.
Levinson et al., "Map-Based Precision Vehicle Localization in Urban Environments," Robotics: Science and Systems, 2007, vol. 4, 8 pages.
Ma et al., "Find your Way by Observing the Sun and Other Semantic Cues," Computer Vision and Pattern Recognition, 2016, 12 pages.
Muja et al., "Fast Approximate Nearest Neighbors with Automatic Algorithm Configuration," VISAPP International Conference on Computer Vision Theory and Applications, 2009, vol. 1, pp. 331-340, 10 pages.

(56) References Cited

OTHER PUBLICATIONS

Mur-Artal et al., "ORB-SLAM: a Versatile and Accurate Monocular SLAM System," IEEE Translations, Robotics, 2015, vol. 31(5), pp. 1147-1163.
Nister et al., "Visual odometry," IEEE Computer Vision and Pattern Recognition, 2004, vol. 1, 35 pages.
Persson "Adaptive Middleware for Self-Configurable Embedded Real-Time Systems," KTH Industrial Engineering and Management, 2009, 92 pages.
Raychaudhuri et al., "Emerging Wreless Technologies and the Future Mobile Internet," p. 48, Cambridge Press, 2011, 3 pages.
Rublee et al., ORB: an efficient alternative to SIFT or SURF, In Computer Vision (ICCV), 2011 IEEE international conference on (pp. 2564-2571) retrieved from http://citeseerxist.psu.edu/viewdoc/download?doi=10.1.1.370.4395&rep=repl&type=pdfs, 8 pages.
Ruchti et al., "Localization on openstreetmap data using a 3D Laser Scanner," IEEE International Conference, Robotics and Automation, 2015, 6 pages.
Scaramuzza et al., "Visual Odometry[tutorial]," IEEE Robotics & Automation Magazine, 2011, vol. 18(4), pp. 80-92.
Stachniss, "Robot Mapping: Short Introduction to Particle Filters and Monte Carlo Localization," Albert-Ludwigs-Universitat Freiburg, 2012, retrieved from http://ais.informatik.uni-freiburg.de/teaching/ws12/mapping/pdf/slam09-particle-filter-4.pdf, 9 pages.
Stephens, Leah, "How Driverless Cars Work," Interesting Engineering, Apr. 28, 2016, available at https://interestingengineering.com/driverless-cars-work/, 7 pages.
Stoller, "Leader Election in Distributed Systems with Crash Failures," Indiana University, 1997, pp. 1-15.
Strunk et al., "The Elements of Style," 3d ed, Macmillan Publishing Co., 1979, 3 pages.
Suwatthikul, "Fault detection and diagnosis for in-vehicle networks," Intech, 2010, pp. 283-286 [retrieved from: www.intechopen.com/books/fault-detection-and-diagnosis-for-in-vehicle-networks].
Thurn/Burgard/Fox, "Probabilistic Robotics," The MIT Press, 2010, retrieved from http://robotics.usc.edu/~gaurav/CS547/lecture6-2010-particle-filters.pdf, 51 pages.
Urmson et al., "Autonomous Driving in Urban Environments: Boss and the Urban Challenge," Journal of Field Robotics, 2008, vol. 25(8), pp. 425-466.
Walter et al., "The smart car seat: personalized monitoring of vital signs in automotive applications." Personal and Ubiquitous Computing, Oct. 2011, vol. 15, No. 7, pp. 707-715.
White, "NextEV's NIO IP9 is an incredible four-wheel-drive electric hypercar," WIRED, 2016, retrieved from http://www.wired.co.uk/article/nextev-hypercar-nio-ep9, 6 pages.
Wolf et al., "Design, Implementation, and Evaluation of a Vehicular Hardware Security Module," ICISC'11 Proceedings of the 14th Int'l Conf. Information Security & Cryptology, Springer-Verlag Berlin, Heidelberg, 2011, pp. 302-318.
Wu et al., "Where am I: Place instance and category recognition using spatial PACT," IEEE Conference, Computer Vision and Pattern Recognition, 2008, 8 pages.
Zhang et al., "LOAM: Lidar Odometry and Mapping in Real-time," Robotics Science and Systems, 2014, vol. 2, 9 pages.
Zhang et al., "Real-time Depth Enhanced Monocular Odometry," IEEE/RSJ International Conference, Intelligent Robots and Systems, 2014, pp. 4973-4980.
Zhang et al., "Visual-lidar Odometry and Mapping: Low-drift, Robust, and Fast," IEEE International Conference, Robotics and Automation, 2015, pp. 2174-2181.
International Search Report and Written Opinion for U.S. International (PCT) Patent Application No. PCT/US17/62757, dated Apr. 4, 2018, 12 pages.
International Preliminary Report on Patentability for U.S. International (PCT) Patent Application No. PCT/US17/62757, dated May 21, 2019, 10 pages.
International Search Report and Written Opinion for U.S. international (PCT) Patent Application No. PCT/US18/66885, dated Mar. 5, 2019, 11 pages.
International Preliminary Reporton Patentability for U.S. International (PCT) Patent Application No. PCT/US18/66885, dated Jul. 2, 2019, 10 pages.
International Search Report and Written Opinion for U.S. International (PCT) Patent Application No. PCT/US18/53027, dated Nov. 30, 2018, 12 pages.
International Preliminary Report on Patentability for U.S. International (PCT) Patent Application No. PCT/US18/53027, dated Apr. 30, 2020, 11 pages.
Official Action for U.S. Appl. No. 15/395,924, dated Jan. 25, 2018, 10 pages.
Final Action for U.S. Appl. No. 15/395,924, dated Jul. 30, 2018, 14 pages.
Official Action for U.S. Appl. No. 15/395,924, dated Nov. 19, 2018, 13 pages.
Notice of Allowance for U.S. Appl. No. 15/395,924, dated Apr. 2, 2019, 11 pages.
Official Action for U.S. Appl. No. 15/395,952, dated Aug. 3, 2018, 11 pages.
Final Action for U.S. Appl. No. 15/395,952, dated Jul. 11, 2019, 14 pages.
Official Action for U.S. Appl. No. 15/395,952, dated Jan. 13, 2020, 18 pages.
Official Action for U.S. Appl. No. 15/395,952, dated Jul. 31, 2020, 19 pages.
Notice of Allowance for U.S. Appl. No. 15/395,952, dated Nov. 13, 2020, 16 pages.
Official Action for U.S. Appl. No. 15/407,066, dated Nov. 8, 2018, 9 pages.
Official Action for U.S. Appl. No. 15/407,066, dated Mar. 12, 2019, 11 pages.
Notice of Allowance for U.S. Appl. No. 15/407,066, dated Jul. 3, 2019, 5 pages.
Supplemental Notice of Allowance for U.S. Appl. No. 15/407,066, dated Sep. 10, 2019, 2 pages.
Official Action for U.S. Appl. No. 15/408,143, dated Jun. 15, 2018, 9 pages.
Notice of Allowance for U.S. Appl. No. 15/408,143, dated Nov. 20, 2018, 8 pages.
Notice of Allowance for U.S. Appl. No. 15/634,197, dated Oct. 25, 2018, 8 pages.
Official Action for U.S. Appl. No. 15/665,644, dated Nov. 19, 2018, 32 pages.
Final Action for U.S. Appl. No. 15/665,644, dated Apr. 4, 2019, 19 pages.
Official Action for U.S. Appl. No. 15/665,644, dated Jul. 25, 2019, 16 pages.
Final Action for U.S. Appl. No. 15/665,644, dated Dec. 31, 2019, 18 pages.
Notice of Allowance for U.S. Appl. No. 15/665,644, dated May 15, 2020, 5 pages.
Official Action for U.S. Appl. No. 15/848,851, dated Dec. 12, 2019, 17 pages.
Final Action for U.S. Appl. No. 15/848,851, dated Jun. 10, 2020, 19 pages.
Official Action for U.S. Appl. No. 15/848,851, dated Jul. 23, 2020, 21 pages.
Official Action for U.S. Appl. No. 15/727,838, dated Aug. 15, 2019, 17 pages.
Final Action for U.S. Appl. No. 15/727,838, dated Jan. 13, 2020, 19 pages.
Official Action for U.S. Appl. No. 15/727,838, dated May 8, 2020, 18 pages.
Final Action for U.S. Appl. No. 15/727,838, dated Sep. 29, 2020 23 pages.
Official Action for U.S. Appl. No. 15/786,373, dated Jul. 11, 2019, 14 pages.
Notice of Allowance for U.S. Appl. No. 15/786,373, dated Dec. 27, 2019, 5 pages.
Official Action for U.S. Appl. No. 15/798,016, dated Jul. 15, 2019, 7 pages.
Notice of Allowance for U.S. Appl. No. 15/798,016, dated Nov. 13, 2019, 5 pages.

(56) References Cited

OTHER PUBLICATIONS

Gustafsson et al., "Particle Filters for Positioning, Navigation and Tracking", IEEE Transactions on Signal Processing, Feb. 2, 2002, vol. 50(2), pp. 425-437.
Kwolek, "Finding Location Using Particle Filter and Histogram Matching", International Conference on Artificial Intelligence and Software Computing, 7th International Conference Jun. 2004, pp. 786-791.
Noh et al., "Particle Filter for Correction of GPS location data of mobile robot", Journal of the Korea Institute of Electronic Communication Sciences, Jan. 2012, pp. 381-389, English abstract only.
Notice of Allowance for U.S. Appl. No. 16/246,810, dated Oct. 20, 2020, 18 pages.
Official Action for U.S. Appl. No. 16/826,873, dated Sep. 23, 2022, 12 pages.
U.S. Appl. No. 15/395,924, filed Dec. 30, 2016 now U.S. Pat. No. 10,410,250.
U.S. Appl. No. 15/395,952, filed Dec. 30, 2016 now U.S. Pat. No. 10,970,746.
U.S. Appl. No. 15/407,066, filed Jan. 16, 2017 now U.S. Pat. No. 10,471,829.
U.S. Appl. No. 15/408,143, filed Jan. 17, 2017 now U.S. Pat. No. 10,286,915.
U.S. Appl. No. 15/634,197, filed Jun. 27, 2017 now U.S. Pat. No. 10,234,302.
U.S. Appl. No. 15/665,644, filed Aug. 1, 2016 now U.S. Pat. No. 10,837,790.
U.S. Appl. No. 15/848,851, filed Dec. 20, 2017.
U.S. Appl. No. 15/727,838, filed Oct. 9, 2017.
U.S. Appl. No. 15/786,373, filed Oct. 17, 2017 now U.S. Pat. No. 10,635,109.
U.S. Appl. No. 16/826,873, filed Mar. 23, 2020.
U.S. Appl. No. 15/798,016, filed Oct. 30, 2017 now U.S. Pat. No. 10,606,274.
U.S. Appl. No. 16/246,810, filed Jan. 14, 2019 now U.S. Pat. No. 10/935,978.

\* cited by examiner

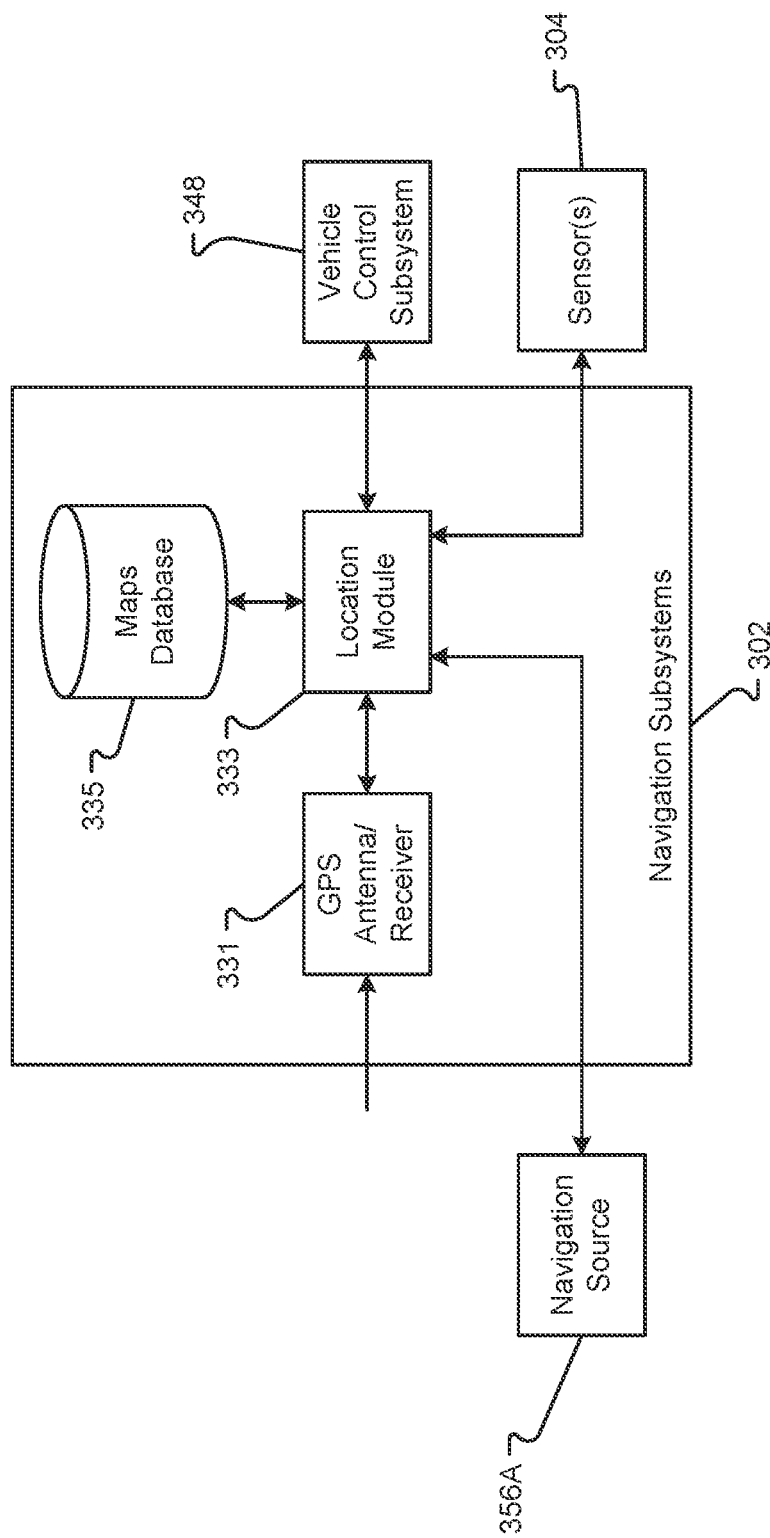

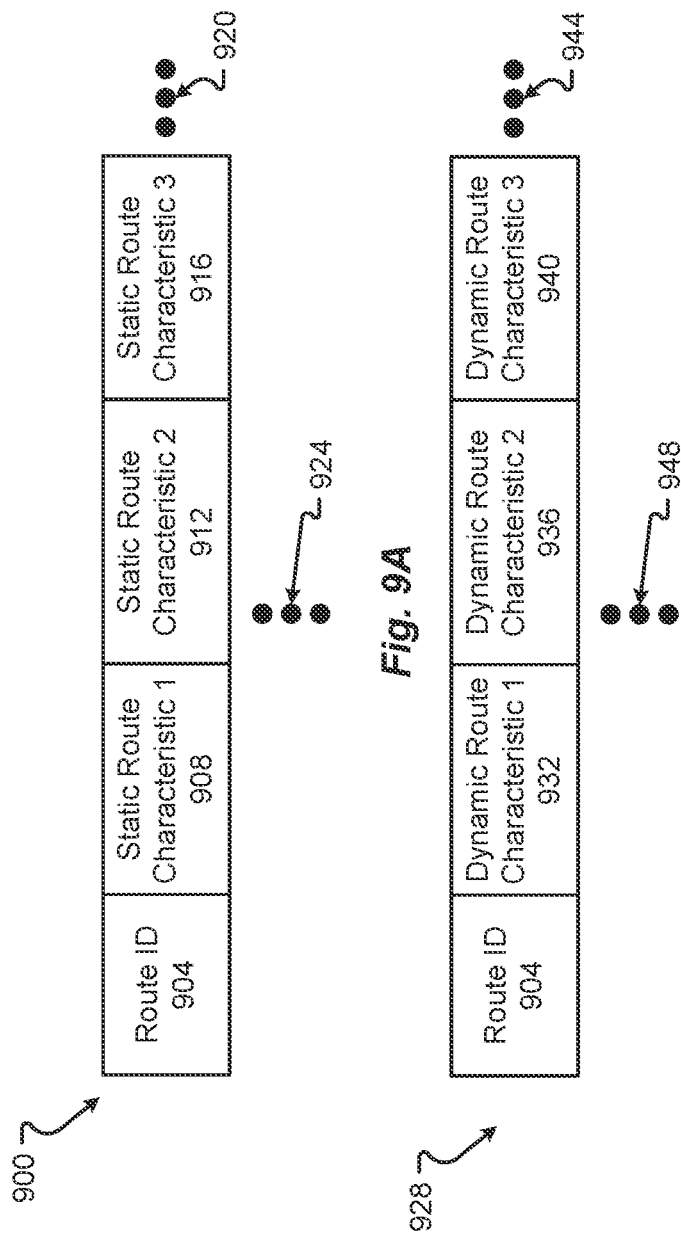

AUTONOMY FIRST ROUTE OPTIMIZATION FOR AUTONOMOUS VEHICLES

CROSS REFERENCE TO RELATED APPLICATIONS

The present application is a continuation of and claims priority to U.S. patent application Ser. No. 15/395,952, filed Dec. 30, 2016, of the same title, which claims the benefits of and priority, under 35 U.S.C. § 119(e), to U.S. Provisional Application Ser. No. 62/424,976, filed on Nov. 21, 2016, entitled "Next Generation Vehicle," the entire disclosures of which are hereby incorporated by reference, in their entirety, for all that they teach and for all purposes.

FIELD

The present disclosure is generally directed to vehicle systems, in particular, toward autonomous or self-driving vehicles.

BACKGROUND

In recent years, transportation methods have changed substantially. The desire to drive has waned and the number of accidents attributed to driver distraction has increased. Generally, people are turning to driverless features in vehicles more often. While some vehicles are able to drive autonomously, it is still difficult to determine when autonomous driving can be used or where it is best used.

BRIEF DESCRIPTION OF THE DRAWINGS

FIG. 3C is a block diagram of an embodiment of a navigation system of the vehicle in accordance with embodiments of the present disclosure;

FIG. 9A is a data diagram of route characteristics according to embodiments of the present disclosure;

FIG. 9B is a data diagram of route characteristics according to embodiments of the present disclosure;

DETAILED DESCRIPTION

Figure 1:
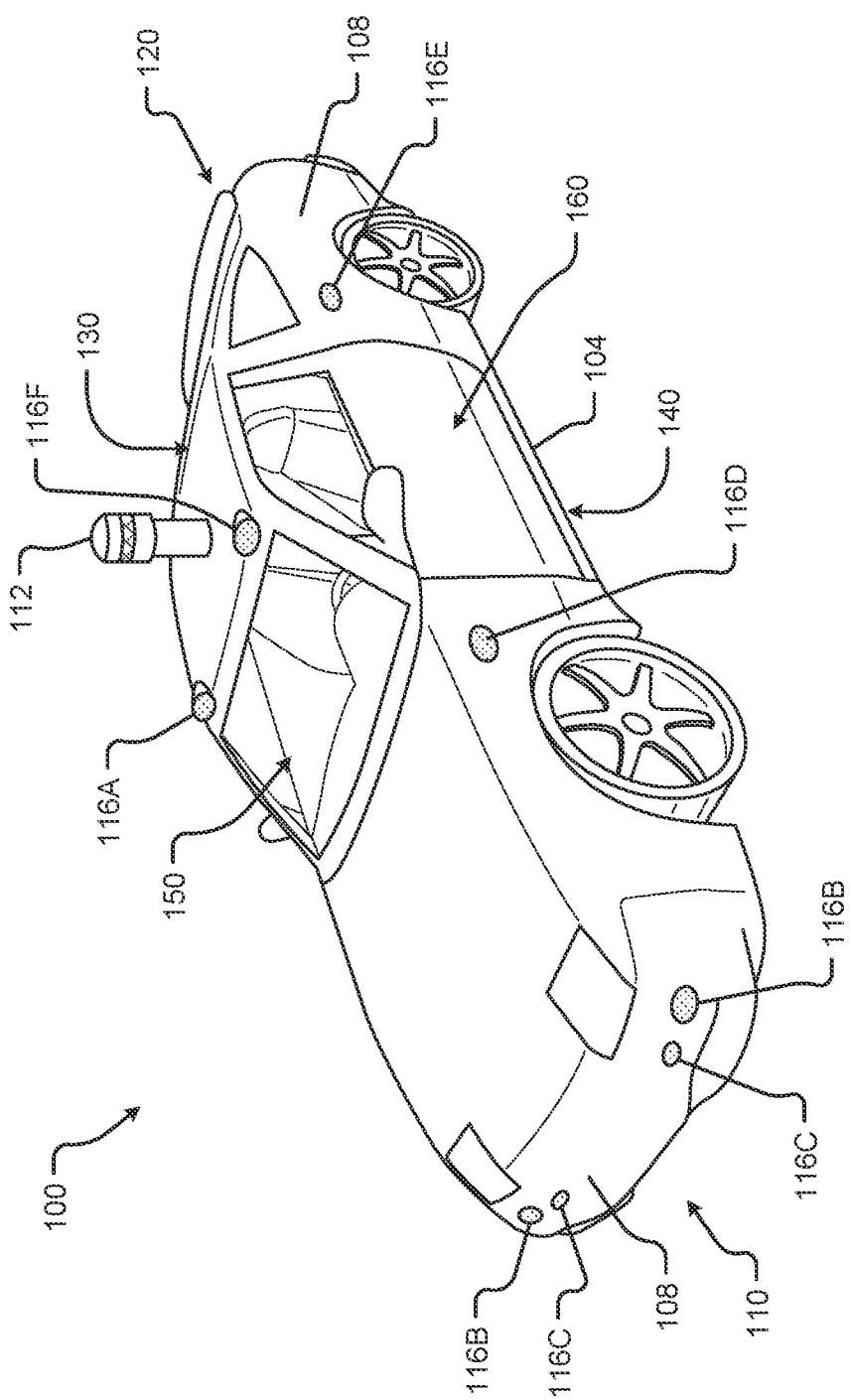
FIG. 1 shows a vehicle in accordance with embodiments of the present disclosure.

Embodiments of the present disclosure will be described in connection with a vehicle, and in some embodiments, an electric vehicle, rechargeable electric vehicle, and/or hybrid-electric vehicle and associated systems. Some embodiments relate to an autonomous vehicle or self-driving vehicle.

Systems and methods herein can determine an optimal route for an autonomous electric vehicle. The system may score viable routes between the start and end locations of a trip using a numeric or other scale that denotes how viable the route is for autonomy. The score is adjusted using a variety of factors where a learning process leverages both offline and online data. Offline learning may be based on factors such as: the average number of lanes in each route segment along every viable route, the average number of traffic lights, the number of school zones, stop signs, and yield signs, the number of lane merges, the average speed limits, historical traffic or road occupant density for different categories of road occupants such as motorcycles, cars, trucks, cyclists, and pedestrians, etc. Any traffic or occupant density model can be constantly or consistently updated as more data is gathered and more occupants are observed.

An online process can augment the learned score with additional real time data including but not limited to: the current state of electric charge, a battery discharge profile for each route, the occupant's implicit preference for each route computed as a function of several factors, for example, the average number of traffic lights along the route, the average number of lanes, the average speed limit, the scenery appeal, etc., a current state of traffic and road condition(s) determined from crowd-sourced information originating from a network of vehicles, occupant's current activity in the vehicle (e.g., meeting vs. just commuting), etc. Other information can also effect the route selection including, but not limited to: location of charging options available to the user, a user's driving habits, a user's calendar information, etc.

Advantages of the algorithm is in improving end-user experience and in improving the efficiency of an autonomous vehicle. In some situations, the vehicle can match a known calendar event, and can choose a longer route to have phone conversation while traveling. In other situations, the shortest route based on time or distance using the autonomous driving capability (which may be different than the shortest route for manual driving) can be chosen. In other words, the route is based on the driving context rather than just on geographical information (i.e., map data). While there may be a computational cost incurred in making decisions with the data available, the decisions will save time and/or improve the user's experience.

Embodiments of the present disclosure will be described in connection with a vehicle, and in some embodiments, an electric vehicle, rechargeable electric vehicle, and/or hybrid-electric vehicle and associated systems.

FIG. 1 shows a perspective view of a vehicle 100 in accordance with embodiments of the present disclosure. The electric vehicle 100 comprises a vehicle front 110, vehicle aft or rear 120, vehicle roof 130, at least one vehicle side 160, a vehicle undercarriage 140, and a vehicle interior 150. In any event, the vehicle 100 may include a frame 104 and one or more body panels 108 mounted or affixed thereto. The vehicle 100 may include one or more interior components (e.g., components inside an interior space 150, or user space, of a vehicle 100, etc.), exterior components (e.g., components outside of the interior space 150, or user space, of a vehicle 100, etc.), drive systems, controls systems, structural components, etc.

Although shown in the form of a car, it should be appreciated that the vehicle 100 described herein may include any conveyance or model of a conveyance, where the conveyance was designed for the purpose of moving one or more tangible objects, such as people, animals, cargo, and the like. The term "vehicle" does not require that a conveyance moves or is capable of movement. Typical vehicles may include but are in no way limited to cars, trucks, motorcycles, busses, automobiles, trains, railed conveyances, boats, ships, marine conveyances, submarine conveyances, airplanes, space craft, flying machines, human-powered conveyances, and the like.

In some embodiments, the vehicle 100 may include a number of sensors, devices, and/or systems that are capable of assisting in driving operations. Examples of the various sensors and systems may include, but are in no way limited to, one or more of cameras (e.g., independent, stereo, combined image, etc.), infrared (IR) sensors, radio frequency (RF) sensors, ultrasonic sensors (e.g., transducers, transceivers, etc.), RADAR sensors (e.g., object-detection sensors and/or systems), LIDAR systems, odometry sensors and/or devices (e.g., encoders, etc.), orientation sensors (e.g., accelerometers, gyroscopes, magnetometer, etc.), navigation sensors and systems (e.g., GPS, etc.), and other ranging, imaging, and/or object-detecting sensors. The sensors may be disposed in an interior space 150 of the vehicle 100 and/or on an outside of the vehicle 100. In some embodiments, the sensors and systems may be disposed in one or more portions of a vehicle 100 (e.g., the frame 104, a body panel, a compartment, etc.).

The vehicle sensors and systems may be selected and/or configured to suit a level of operation associated with the vehicle 100. Among other things, the number of sensors used in a system may be altered to increase or decrease information available to a vehicle control system (e.g., affecting control capabilities of the vehicle 100). Additionally or alternatively, the sensors and systems may be part of one or more advanced driver assistance systems (ADAS) associated with a vehicle 100. In any event, the sensors and systems may be used to provide driving assistance at any level of operation (e.g., from fully-manual to fully-autonomous operations, etc.) as described herein.

The various levels of vehicle control and/or operation can be described as corresponding to a level of autonomy associated with a vehicle 100 for vehicle driving operations. For instance, at Level 0, or fully-manual driving operations, a driver (e.g., a human driver) may be responsible for all the driving control operations (e.g., steering, accelerating, braking, etc.) associated with the vehicle. Level 0 may be referred to as a "No Automation" level. At Level 1, the vehicle may be responsible for a limited number of the driving operations associated with the vehicle, while the driver is still responsible for most driving control operations. An example of a Level 1 vehicle may include a vehicle in which the throttle control and/or braking operations may be controlled by the vehicle (e.g., cruise control operations, etc.). Level 1 may be referred to as a "Driver Assistance" level. At Level 2, the vehicle may collect information (e.g., via one or more driving assistance systems, sensors, etc.) about an environment of the vehicle (e.g., surrounding area, roadway, traffic, ambient conditions, etc.) and use the collected information to control driving operations (e.g., steering, accelerating, braking, etc.) associated with the vehicle. In a Level 2 autonomous vehicle, the driver may be required to perform other aspects of driving operations not controlled by the vehicle. Level 2 may be referred to as a "Partial Automation" level. It should be appreciated that Levels 0-2 all involve the driver monitoring the driving operations of the vehicle.

At Level 3, the driver may be separated from controlling all the driving operations of the vehicle except when the vehicle makes a request for the operator to act or intervene in controlling one or more driving operations. In other words, the driver may be separated from controlling the vehicle unless the driver is required to take over for the vehicle. Level 3 may be referred to as a "Conditional Automation" level. At Level 4, the driver may be separated from controlling all the driving operations of the vehicle and the vehicle may control driving operations even when a user fails to respond to a request to intervene. Level 4 may be referred to as a "High Automation" level. At Level 5, the vehicle can control all the driving operations associated with the vehicle in all driving modes. The vehicle in Level 5 may continually monitor traffic, vehicular, roadway, and/or environmental conditions while driving the vehicle. In Level 5, there is no human driver interaction required in any driving mode. Accordingly, Level 5 may be referred to as a "Full Automation" level. It should be appreciated that in Levels 3-5 the vehicle, and/or one or more automated driving systems associated with the vehicle, monitors the driving operations of the vehicle and the driving environment.

As shown in FIG. 1, the vehicle 100 may, for example, include at least one of a ranging and imaging system 112 (e.g., LIDAR, etc.), an imaging sensor 116A, 116F (e.g., camera, IR, etc.), a radio object-detection and ranging system sensors 116B (e.g., RADAR, RF, etc.), ultrasonic sensors 116C, and/or other object-detection sensors 116D, 116E. In some embodiments, the LIDAR system 112 and/or sensors may be mounted on a roof 130 of the vehicle 100. In one embodiment, the RADAR sensors 116B may be disposed at least at a front 110, aft 120, or side 160 of the vehicle 100. Among other things, the RADAR sensors may be used to monitor and/or detect a position of other vehicles, pedestrians, and/or other objects near, or proximal to, the vehicle 100. While shown associated with one or more areas of a vehicle 100, it should be appreciated that any of the sensors and systems 116A-K, 112 illustrated in FIGS. 1 and 2 may be disposed in, on, and/or about the vehicle 100 in any position, area, and/or zone of the vehicle 100.

Figure 2:
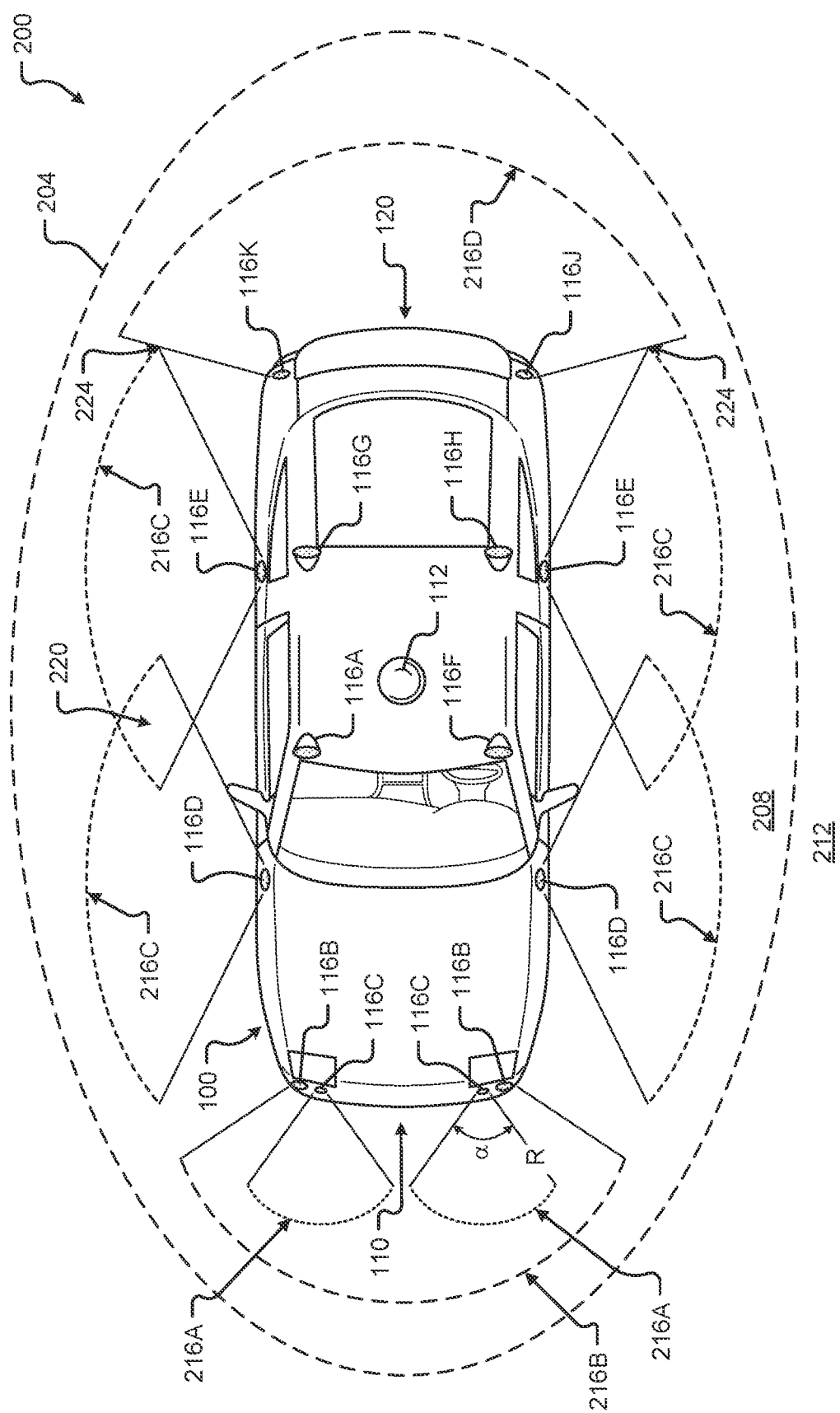
FIG. 2 shows a plan view of the vehicle in accordance with at least some embodiments of the present disclosure.

Referring now to FIG. 2, a plan view of a vehicle 100 will be described in accordance with embodiments of the present disclosure. In particular, FIG. 2 shows a vehicle sensing environment 200 at least partially defined by the sensors and systems 116A-K, 112 disposed in, on, and/or about the vehicle 100. Each sensor 116A-K may include an operational detection range R and operational detection angle. The operational detection range R may define the effective detection limit, or distance, of the sensor 116A-K. In some cases, this effective detection limit may be defined as a distance from a portion of the sensor 116A-K (e.g., a lens, sensing surface, etc.) to a point in space offset from the sensor 116A-K. The effective detection limit may define a distance, beyond which, the sensing capabilities of the sensor 116A-K deteriorate, fail to work, or are unreliable. In some embodiments, the effective detection limit may define a distance, within which, the sensing capabilities of the sensors 116A-K are able to provide accurate and/or reliable detection information. The operational detection angle may define at least one angle of a span, or between horizontal and/or vertical limits, of a sensor 116A-K. As can be appreciated, the operational detection limit and the operational detection angle of a sensor 116A-K together may define the effective detection zone 216A-D (e.g., the effective detection area, and/or volume, etc.) of a sensor 116A-K.

In some embodiments, the vehicle 100 may include a ranging and imaging system 112 such as LIDAR, or the like. The ranging and imaging system 112 may be configured to detect visual information in an environment surrounding the vehicle 100. The visual information detected in the environment surrounding the ranging and imaging system 112 may be processed (e.g., via one or more sensor and/or system processors, etc.) to generate a complete 360-degree view of an environment 200 around the vehicle. The ranging and imaging system 112 may be configured to generate changing 360-degree views of the environment 200 in real-time, for instance, as the vehicle 100 drives. In some cases, the ranging and imaging system 112 may have an effective detection limit 204 that is some distance from the center of the vehicle 100 outward over 360 degrees. The effective detection limit 204 of the ranging and imaging system 112 defines a view zone 208 (e.g., an area and/or volume, etc.) surrounding the vehicle 100. Any object falling outside of the view zone 208 is in the undetected zone 212 and would not be detected by the ranging and imaging system 112 of the vehicle 100.

Sensor data and information may be collected by one or more sensors or systems 116A-K, 112 of the vehicle 100 monitoring the vehicle sensing environment 200. This information may be processed (e.g., via a processor, computer-vision system, etc.) to determine targets (e.g., objects, signs, people, markings, roadways, conditions, etc.) inside one or more detection zones 208, 216A-D associated with the vehicle sensing environment 200. In some cases, information from multiple sensors 116A-K may be processed to form composite sensor detection information. For example, a first sensor 116A and a second sensor 116F may correspond to a first camera 116A and a second camera 116F aimed in a forward traveling direction of the vehicle 100. In this example, images collected by the cameras 116A, 116F may be combined to form stereo image information. This composite information may increase the capabilities of a single sensor in the one or more sensors 116A-K by, for example, adding the ability to determine depth associated with targets in the one or more detection zones 208, 216A-D. Similar image data may be collected by rear view cameras (e.g., sensors 116G, 116H) aimed in a rearward traveling direction vehicle 100.

In some embodiments, multiple sensors 116A-K may be effectively joined to increase a sensing zone and provide increased sensing coverage. For instance, multiple RADAR sensors 116B disposed on the front 110 of the vehicle may be joined to provide a zone 216B of coverage that spans across an entirety of the front 110 of the vehicle. In some cases, the multiple RADAR sensors 116B may cover a detection zone 216B that includes one or more other sensor detection zones 216A. These overlapping detection zones may provide redundant sensing, enhanced sensing, and/or provide greater detail in sensing within a particular portion (e.g., zone 216A) of a larger zone (e.g., zone 216B). Additionally or alternatively, the sensors 116A-K of the vehicle 100 may be arranged to create a complete coverage, via one or more sensing zones 208, 216A-D around the vehicle 100. In some areas, the sensing zones 216C of two or more sensors 116D, 116E may intersect at an overlap zone 220. In some areas, the angle and/or detection limit of two or more sensing zones 216C, 216D (e.g., of two or more sensors 116E, 116J, 116K) may meet at a virtual intersection point 224.

The vehicle 100 may include a number of sensors 116E, 116G, 116H, 116J, 116K disposed proximal to the rear 120 of the vehicle 100. These sensors can include, but are in no way limited to, an imaging sensor, camera, IR, a radio object-detection and ranging sensors, RADAR, RF, ultrasonic sensors, and/or other object-detection sensors. Among other things, these sensors 116E, 116G, 116H, 116J, 116K may detect targets near or approaching the rear of the vehicle 100. For example, another vehicle approaching the rear 120 of the vehicle 100 may be detected by one or more of the ranging and imaging system (e.g., LIDAR) 112, rear-view cameras 116G, 116H, and/or rear facing RADAR sensors 116J, 116K. As described above, the images from the rear-view cameras 116G, 116H may be processed to generate a stereo view (e.g., providing depth associated with an object or environment, etc.) for targets visible to both cameras 116G, 116H. As another example, the vehicle 100 may be driving and one or more of the ranging and imaging system 112, front-facing cameras 116A, 116F, front-facing RADAR sensors 116B, and/or ultrasonic sensors 116C may detect targets in front of the vehicle 100. This approach may provide critical sensor information to a vehicle control system in at least one of the autonomous driving levels described above. For instance, when the vehicle 100 is driving autonomously (e.g., Level 3, Level 4, or Level 5) and detects other vehicles stopped in a travel path, the sensor detection information may be sent to the vehicle control system of the vehicle 100 to control a driving operation (e.g., braking, decelerating, etc.) associated with the vehicle 100 (in this example, slowing the vehicle 100 as to avoid colliding with the stopped other vehicles). As yet another example, the vehicle 100 may be operating and one or more of the ranging and imaging system 112, and/or the side-facing sensors 116D, 116E (e.g., RADAR, ultrasonic, camera, combinations thereof, and/or other type of sensor), may detect targets at a side of the vehicle 100. It should be appreciated that the sensors 116A-K may detect a target that is both at a side 160 and a front 110 of the vehicle 100 (e.g., disposed at a diagonal angle to a centerline of the vehicle 100 running from the front 110 of the vehicle 100 to the rear 120 of the vehicle). Additionally or alternatively, the sensors 116A-K may detect a target that is both, or simultaneously, at a side 160 and a rear 120 of the vehicle 100 (e.g., disposed at a diagonal angle to the centerline of the vehicle 100).

Figure 3A:
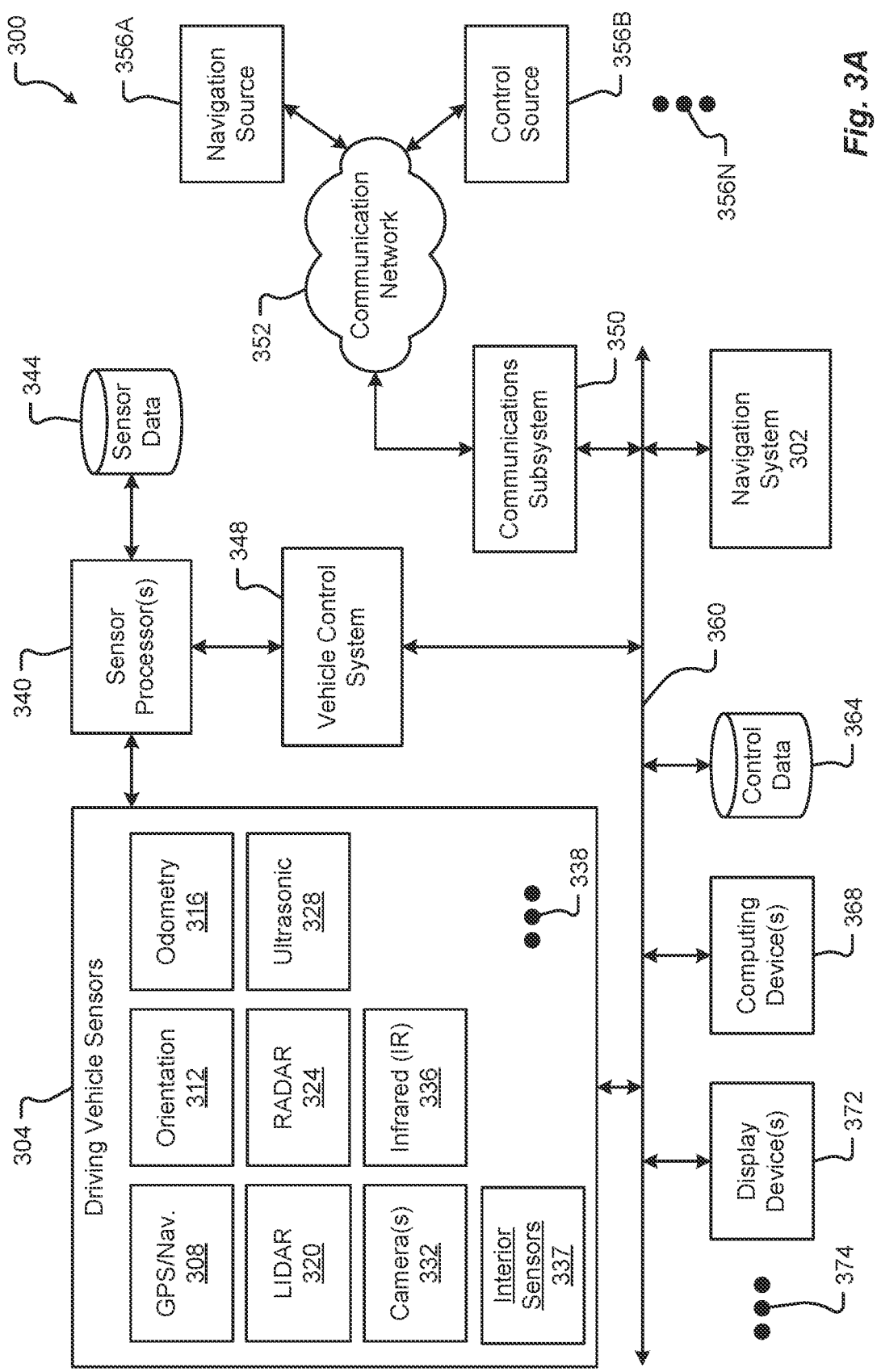
FIG. 3A is a block diagram of an embodiment of a communication environment of the vehicle in accordance with embodiments of the present disclosure.

FIG. 3 is a is a block diagram of an embodiment of a communication environment 300 of the vehicle 100 in accordance with embodiments of the present disclosure. The communication system 300 may include one or more vehicle driving vehicle sensors and systems 304, sensor processors 340, sensor data memory 344, vehicle control system 348, communications subsystem 350, control data 364, computing devices 368, display devices 372, and other components 374 that may be associated with a vehicle 100. These associated components may be electrically and/or communicatively coupled to one another via at least one bus 360. In some embodiments, the one or more associated components may send and/or receive signals across a communication network 352 to at least one of a navigation source 356A, a control source 356B, or some other entity 356N.

In accordance with at least some embodiments of the present disclosure, the communication network 352 may comprise any type of known communication medium or collection of communication media and may use any type of protocols, such as SIP, TCP/IP, SNA, IPX, AppleTalk, and the like, to transport messages between endpoints. The communication network 352 may include wired and/or wireless communication technologies. The Internet is an example of the communication network 352 that constitutes an Internet Protocol (IP) network consisting of many computers, computing networks, and other communication devices located all over the world, which are connected through many telephone systems and other means. Other examples of the communication network 104 include, without limitation, a standard Plain Old Telephone System (POTS), an Integrated Services Digital Network (ISDN), the Public Switched Telephone Network (PSTN), a Local Area Network (LAN), such as an Ethernet network, a Token-Ring network and/or the like, a Wide Area Network (WAN), a virtual network, including without limitation a virtual private network ("VPN"); the Internet, an intranet, an extranet, a cellular network, an infra-red network; a wireless network (e.g., a network operating under any of the IEEE 802.9 suite of protocols, the Bluetooth® protocol known in the art, and/or any other wireless protocol), and any other type of packet-switched or circuit-switched network known in the art and/or any combination of these and/or other networks. In addition, it can be appreciated that the communication network 352 need not be limited to any one network type, and instead may be comprised of a number of different networks and/or network types. The communication network 352 may comprise a number of different communication media such as coaxial cable, copper cable/wire, fiber-optic cable, antennas for transmitting/receiving wireless messages, and combinations thereof.

The driving vehicle sensors and systems 304 may include at least one navigation 308 (e.g., global positioning system (GPS), etc.), orientation 312, odometry 316, LIDAR 320, RADAR 324, ultrasonic 328, camera 332, infrared (IR) 336, and/or other sensor or system 338. These driving vehicle sensors and systems 304 may be similar, if not identical, to the sensors and systems 116A-K, 112 described in conjunction with FIGS. 1 and 2.

The navigation sensor 308 may include one or more sensors having receivers and antennas that are configured to utilize a satellite-based navigation system including a network of navigation satellites capable of providing geolocation and time information to at least one component of the vehicle 100. Examples of the navigation sensor 308 as described herein may include, but are not limited to, at least one of Garmin® GLO™ family of GPS and GLONASS combination sensors, Garmin® GPS 15x™ family of sensors, Garmin® GPS 16x™ family of sensors with high-sensitivity receiver and antenna, Garmin® GPS 18x OEM family of high-sensitivity GPS sensors, Dewetron DEWE-VGPS series of GPS sensors, GlobalSat 1-Hz series of GPS sensors, other industry-equivalent navigation sensors and/or systems, and may perform navigational and/or geolocation functions using any known or future-developed standard and/or architecture.

The orientation sensor 312 may include one or more sensors configured to determine an orientation of the vehicle 100 relative to at least one reference point. In some embodiments, the orientation sensor 312 may include at least one pressure transducer, stress/strain gauge, accelerometer, gyroscope, and/or geomagnetic sensor. Examples of the navigation sensor 308 as described herein may include, but are not limited to, at least one of Bosch Sensortec BMX 160 series low-power absolute orientation sensors, Bosch Sensortec BMX055 9-axis sensors, Bosch Sensortec BMI055 6-axis inertial sensors, Bosch Sensortec BMI160 6-axis inertial sensors, Bosch Sensortec BMF055 9-axis inertial sensors (accelerometer, gyroscope, and magnetometer) with integrated Cortex M0+ microcontroller, Bosch Sensortec BMP280 absolute barometric pressure sensors, Infineon TLV493D-A1B6 3D magnetic sensors, Infineon TLI493D-W1B6 3D magnetic sensors, Infineon TL family of 3D magnetic sensors, Murata Electronics SCC2000 series combined gyro sensor and accelerometer, Murata Electronics SCC1300 series combined gyro sensor and accelerometer, other industry-equivalent orientation sensors and/or systems, and may perform orientation detection and/or determination functions using any known or future-developed standard and/or architecture.

The odometry sensor and/or system 316 may include one or more components that is configured to determine a change in position of the vehicle 100 over time. In some embodiments, the odometry system 316 may utilize data from one or more other sensors and/or systems 304 in determining a position (e.g., distance, location, etc.) of the vehicle 100 relative to a previously measured position for the vehicle 100. Additionally or alternatively, the odometry sensors 316 may include one or more encoders, Hall speed sensors, and/or other measurement sensors/devices configured to measure a wheel speed, rotation, and/or number of revolutions made over time. Examples of the odometry sensor/system 316 as described herein may include, but are not limited to, at least one of Infineon TLE4924/26/27/28C high-performance speed sensors, Infineon TL4941plusC(B) single chip differential Hall wheel-speed sensors, Infineon TL5041plusC Giant Mangnetoresistance (GMR) effect sensors, Infineon TL family of magnetic sensors, EPC Model 25SP Accu-CoderPro™ incremental shaft encoders, EPC Model 30M compact incremental encoders with advanced magnetic sensing and signal processing technology, EPC Model 925 absolute shaft encoders, EPC Model 958 absolute shaft encoders, EPC Model MA36S/MA63S/SA36S absolute shaft encoders, Dynapar™ F18 commutating optical encoder, Dynapar™ HS35R family of phased array encoder sensors, other industry-equivalent odometry sensors and/or systems, and may perform change in position detection and/or determination functions using any known or future-developed standard and/or architecture.

The LIDAR sensor/system 320 may include one or more components configured to measure distances to targets using laser illumination. In some embodiments, the LIDAR sensor/system 320 may provide 3D imaging data of an environment around the vehicle 100. The imaging data may be processed to generate a full 360-degree view of the environment around the vehicle 100. The LIDAR sensor/system 320 may include a laser light generator configured to generate a plurality of target illumination laser beams (e.g., laser light channels). In some embodiments, this plurality of laser beams may be aimed at, or directed to, a rotating reflective surface (e.g., a mirror) and guided outwardly from the LIDAR sensor/system 320 into a measurement environment. The rotating reflective surface may be configured to continually rotate 360 degrees about an axis, such that the plurality of laser beams is directed in a full 360-degree range around the vehicle 100. A photodiode receiver of the LIDAR sensor/system 320 may detect when light from the plurality of laser beams emitted into the measurement environment returns (e.g., reflected echo) to the LIDAR sensor/system 320. The LIDAR sensor/system 320 may calculate, based on a time associated with the emission of light to the detected return of light, a distance from the vehicle 100 to the illuminated target. In some embodiments, the LIDAR sensor/system 320 may generate over 2.0 million points per second and have an effective operational range of at least 100 meters. Examples of the LIDAR sensor/system 320 as described herein may include, but are not limited to, at least one of Velodyne® LiDAR™ HDL-64E 64-channel LIDAR sensors, Velodyne® LiDAR™ HDL-32E 32-channel LIDAR sensors, Velodyne® LiDAR™ PUCK™ VLP-16 16-channel LIDAR sensors, Leica Geosystems Pegasus: Two mobile sensor platform, Garmin® LIDAR-Lite v3 measurement sensor, Quanergy M8 LiDAR sensors, Quanergy S3 solid state LiDAR sensor, LeddarTech® LeddarVU compact solid state fixed-beam LIDAR sensors, other industry-equivalent LIDAR sensors and/or systems, and may perform illuminated target and/or obstacle detection in an environment around the vehicle 100 using any known or future-developed standard and/or architecture.

The RADAR sensors 324 may include one or more radio components that are configured to detect objects/targets in an environment of the vehicle 100. In some embodiments, the RADAR sensors 324 may determine a distance, position, and/or movement vector (e.g., angle, speed, etc.) associated with a target over time. The RADAR sensors 324 may include a transmitter configured to generate and emit electromagnetic waves (e.g., radio, microwaves, etc.) and a receiver configured to detect returned electromagnetic waves. In some embodiments, the RADAR sensors 324 may include at least one processor configured to interpret the returned electromagnetic waves and determine locational properties of targets. Examples of the RADAR sensors 324 as described herein may include, but are not limited to, at least one of Infineon RASIC™ RTN7735PL transmitter and RRN7745PL/46PL receiver sensors, Autoliv ASP Vehicle RADAR sensors, Delphi L2C0051TR 77 GHz ESR Electronically Scanning Radar sensors, Fujitsu Ten Ltd. Automotive Compact 77 GHz 3D Electronic Scan Millimeter Wave Radar sensors, other industry-equivalent RADAR sensors and/or systems, and may perform radio target and/or obstacle detection in an environment around the vehicle 100 using any known or future-developed standard and/or architecture.

The ultrasonic sensors 328 may include one or more components that are configured to detect objects/targets in an environment of the vehicle 100. In some embodiments, the ultrasonic sensors 328 may determine a distance, position, and/or movement vector (e.g., angle, speed, etc.) associated with a target over time. The ultrasonic sensors 328 may include an ultrasonic transmitter and receiver, or transceiver, configured to generate and emit ultrasound waves and interpret returned echoes of those waves. In some embodiments, the ultrasonic sensors 328 may include at least one processor configured to interpret the returned ultrasonic waves and determine locational properties of targets. Examples of the ultrasonic sensors 328 as described herein may include, but are not limited to, at least one of Texas Instruments TIDA-00151 automotive ultrasonic sensor interface IC sensors, MaxBotix® MB8450 ultrasonic proximity sensor, MaxBotix® ParkSonar™-EZ ultrasonic proximity sensors, Murata Electronics MA40H1S-R open-structure ultrasonic sensors, Murata Electronics MA40S4R/S open-structure ultrasonic sensors, Murata Electronics MA58MF14-7N waterproof ultrasonic sensors, other industry-equivalent ultrasonic sensors and/or systems, and may perform ultrasonic target and/or obstacle detection in an environment around the vehicle 100 using any known or future-developed standard and/or architecture.

The camera sensors 332 may include one or more components configured to detect image information associated with an environment of the vehicle 100. In some embodiments, the camera sensors 332 may include a lens, filter, image sensor, and/or a digital image processor. It is an aspect of the present disclosure that multiple camera sensors 332 may be used together to generate stereo images providing depth measurements. Examples of the camera sensors 332 as described herein may include, but are not limited to, at least one of ON Semiconductor® MT9V024 Global Shutter VGA GS CMOS image sensors, Teledyne DALSA Falcon2 camera sensors, CMOSIS CMV50000 high-speed CMOS image sensors, other industry-equivalent camera sensors and/or systems, and may perform visual target and/or obstacle detection in an environment around the vehicle 100 using any known or future-developed standard and/or architecture.

The infrared (IR) sensors 336 may include one or more components configured to detect image information associated with an environment of the vehicle 100. The IR sensors 336 may be configured to detect targets in low-light, dark, or poorly-lit environments. The IR sensors 336 may include an IR light emitting element (e.g., IR light emitting diode (LED), etc.) and an IR photodiode. In some embodiments, the IR photodiode may be configured to detect returned IR light at or about the same wavelength to that emitted by the IR light emitting element. In some embodiments, the IR sensors 336 may include at least one processor configured to interpret the returned IR light and determine locational properties of targets. The IR sensors 336 may be configured to detect and/or measure a temperature associated with a target (e.g., an object, pedestrian, other vehicle, etc.). Examples of IR sensors 336 as described herein may include, but are not limited to, at least one of Opto Diode lead-salt IR array sensors, Opto Diode OD-850 Near-IR LED sensors, Opto Diode SA/SHA727 steady state IR emitters and IR detectors, FLIR® LS microbolometer sensors, FLIR® TacFLIR 380-HD InSb MWIR FPA and HD MWIR thermal sensors, FLIR® VOx 640×480 pixel detector sensors, Delphi IR sensors, other industry-equivalent IR sensors and/or systems, and may perform IR visual target and/or obstacle detection in an environment around the vehicle 100 using any known or future-developed standard and/or architecture.

The vehicle 100 can also include one or more interior sensors 337. Interior sensors 337 can measure characteristics of the inside environment of the vehicle 100. The interior sensors 337 may be as described in conjunction with FIG. 3B.

A navigation system 302 can include any hardware and/or software used to navigate the vehicle either manually or autonomously. The navigation system 302 may be as described in conjunction with FIG. 3C.

In some embodiments, the driving vehicle sensors and systems 304 may include other sensors 338 and/or combinations of the sensors 306-337 described above. Additionally or alternatively, one or more of the sensors 306-337 described above may include one or more processors configured to process and/or interpret signals detected by the one or more sensors 306-337. In some embodiments, the processing of at least some sensor information provided by the vehicle sensors and systems 304 may be processed by at least one sensor processor 340. Raw and/or processed sensor data may be stored in a sensor data memory 344 storage medium. In some embodiments, the sensor data memory 344 may store instructions used by the sensor processor 340 for processing sensor information provided by the sensors and systems 304. In any event, the sensor data memory 344 may be a disk drive, optical storage device, solid-state storage device such as a random access memory ("RAM") and/or a read-only memory ("ROM"), which can be programmable, flash-updateable, and/or the like.

The vehicle control system 348 may receive processed sensor information from the sensor processor 340 and determine to control an aspect of the vehicle 100. Controlling an aspect of the vehicle 100 may include presenting information via one or more display devices 372 associated with the vehicle, sending commands to one or more computing devices 368 associated with the vehicle, and/or controlling a driving operation of the vehicle. In some embodiments, the vehicle control system 348 may correspond to one or more computing systems that control driving operations of the vehicle 100 in accordance with the Levels of driving autonomy described above. In one embodiment, the vehicle control system 348 may operate a speed of the vehicle 100 by controlling an output signal to the accelerator and/or braking system of the vehicle. In this example, the vehicle control system 348 may receive sensor data describing an environment surrounding the vehicle 100 and, based on the sensor data received, determine to adjust the acceleration, power output, and/or braking of the vehicle 100. The vehicle control system 348 may additionally control steering and/or other driving functions of the vehicle 100.

The vehicle control system 348 may communicate, in real-time, with the driving sensors and systems 304 forming a feedback loop. In particular, upon receiving sensor information describing a condition of targets in the environment surrounding the vehicle 100, the vehicle control system 348 may autonomously make changes to a driving operation of the vehicle 100. The vehicle control system 348 may then receive subsequent sensor information describing any change to the condition of the targets detected in the environment as a result of the changes made to the driving operation. This continual cycle of observation (e.g., via the sensors, etc.) and action (e.g., selected control or non-control of vehicle operations, etc.) allows the vehicle 100 to operate autonomously in the environment.

In some embodiments, the one or more components of the vehicle 100 (e.g., the driving vehicle sensors 304, vehicle control system 348, display devices 372, etc.) may communicate across the communication network 352 to one or more entities 356A-N via a communications subsystem 350 of the vehicle 100. Embodiments of the communications subsystem 350 are described in greater detail in conjunction with FIG. 5. For instance, the navigation sensors 308 may receive global positioning, location, and/or navigational information from a navigation source 356A. In some embodiments, the navigation source 356A may be a global navigation satellite system (GNSS) similar, if not identical, to NAVSTAR GPS, GLONASS, EU Galileo, and/or the BeiDou Navigation Satellite System (BDS) to name a few.

In some embodiments, the vehicle control system 348 may receive control information from one or more control sources 356B. The control source 356 may provide vehicle control information including autonomous driving control commands, vehicle operation override control commands, and the like. The control source 356 may correspond to an autonomous vehicle control system, a traffic control system, an administrative control entity, and/or some other controlling server. It is an aspect of the present disclosure that the vehicle control system 348 and/or other components of the vehicle 100 may exchange communications with the control source 356 across the communication network 352 and via the communications subsystem 350.

Information associated with controlling driving operations of the vehicle 100 may be stored in a control data memory 364 storage medium. The control data memory 364 may store instructions used by the vehicle control system 348 for controlling driving operations of the vehicle 100, historical control information, autonomous driving control rules, and the like. In some embodiments, the control data memory 364 may be a disk drive, optical storage device, solid-state storage device such as a random access memory ("RAM") and/or a read-only memory ("ROM"), which can be programmable, flash-updateable, and/or the like.

In addition to the mechanical components described herein, the vehicle 100 may include a number of user interface devices. The user interface devices receive and translate human input into a mechanical movement or electrical signal or stimulus. The human input may be one or more of motion (e.g., body movement, body part movement, in two-dimensional or three-dimensional space, etc.), voice, touch, and/or physical interaction with the components of the vehicle 100. In some embodiments, the human input may be configured to control one or more functions of the vehicle 100 and/or systems of the vehicle 100 described herein. User interfaces may include, but are in no way limited to, at least one graphical user interface of a display device, steering wheel or mechanism, transmission lever or button (e.g., including park, neutral, reverse, and/or drive positions, etc.), throttle control pedal or mechanism, brake control pedal or mechanism, power control switch, communications equipment, etc.

Figure 3B:
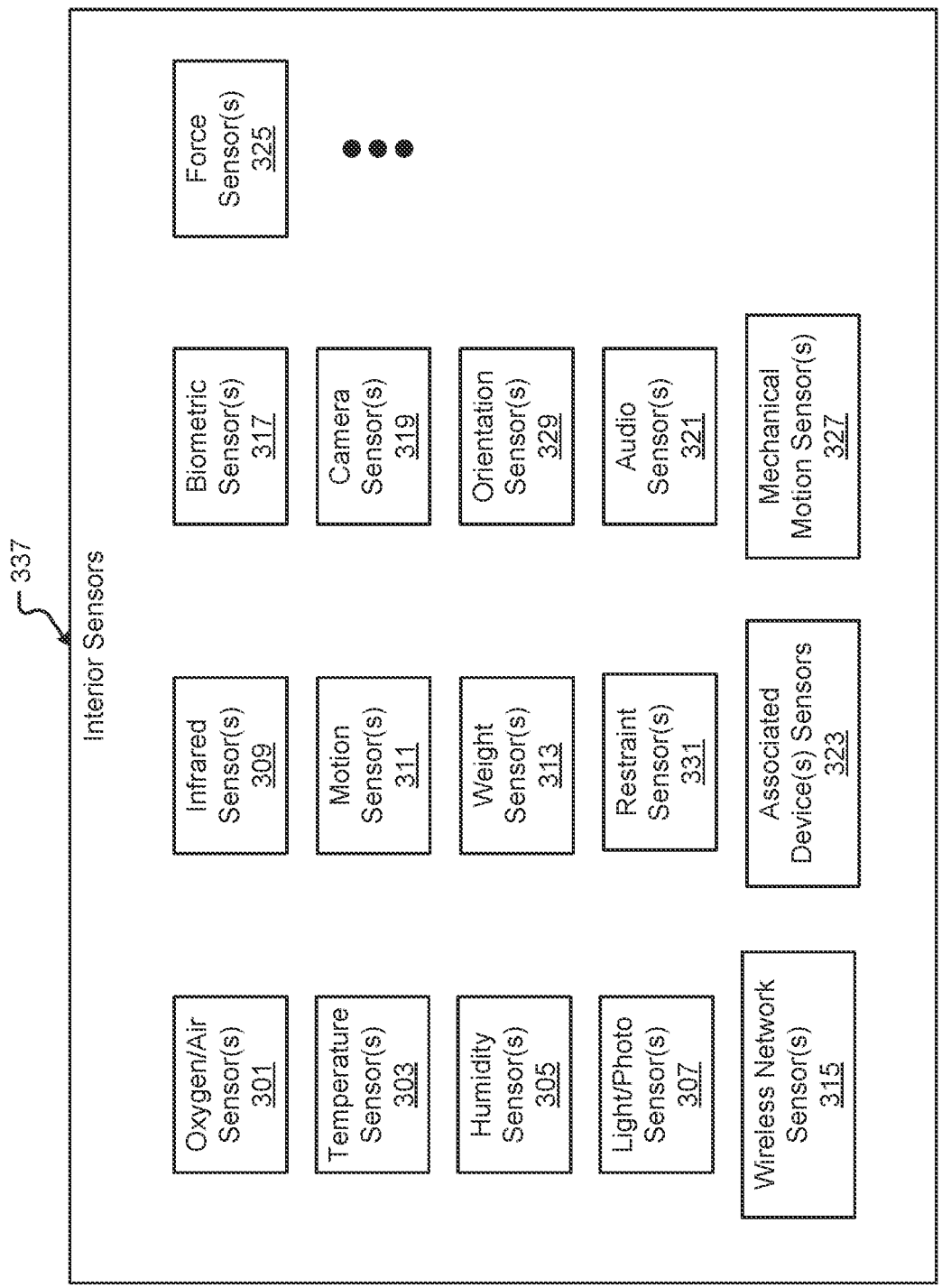
FIG. 3B is a block diagram of an embodiment of interior sensors within the vehicle in accordance with embodiments of the present disclosure.

FIG. 3B shows a block diagram of an embodiment of interior sensors 337 for a vehicle 100. The interior sensors 337 may be arranged into one or more groups, based at least partially on the function of the interior sensors 337. For example, the interior space of a vehicle 100 may include environmental sensors, a user interface sensors, and/or safety sensors. Additionally or alternatively, there may be sensors associated with various devices inside the vehicle (e.g., smart phones, tablets, mobile computers, wearables, etc.)

Environmental sensors may comprise sensors configured to collect data relating to the internal environment of a vehicle 100. Examples of environmental sensors may include one or more of, but are not limited to: oxygen/air sensors 301, temperature sensors 303, humidity sensors 305, light/photo sensors 307, and more. The oxygen/air sensors 301 may be configured to detect a quality or characteristic of the air in the interior space 108 of the vehicle 100 (e.g., ratios and/or types of gasses comprising the air inside the vehicle 100, dangerous gas levels, safe gas levels, etc.). Temperature sensors 303 may be configured to detect temperature readings of one or more objects, users 216, and/or areas of a vehicle 100. Humidity sensors 305 may detect an amount of water vapor present in the air inside the vehicle 100. The light/photo sensors 307 can detect an amount of light present in the vehicle 100. Further, the light/photo sensors 307 may be configured to detect various levels of light intensity associated with light in the vehicle 100.

User interface sensors may comprise sensors configured to collect data relating to one or more users (e.g., a driver and/or passenger(s)) in a vehicle 100. As can be appreciated, the user interface sensors may include sensors that are configured to collect data from users 216 in one or more areas of the vehicle 100. Examples of user interface sensors may include one or more of, but are not limited to: infrared sensors 309, motion sensors 311, weight sensors 313, wireless network sensors 315, biometric sensors 317, camera (or image) sensors 319, audio sensors 321, and more.

Infrared sensors 309 may be used to measure IR light irradiating from at least one surface, user, or another object in the vehicle 100. Among other things, the Infrared sensors 309 may be used to measure temperatures, form images (especially in low light conditions), identify users 216, and even detect motion in the vehicle 100.

The motion sensors 311 may detect motion and/or movement of objects inside the vehicle 104. Optionally, the motion sensors 311 may be used alone or in combination to detect movement. For example, a user may be operating a vehicle 100 (e.g., while driving, etc.) when a passenger in the rear of the vehicle 100 unbuckles a safety belt and proceeds to move about the vehicle 10. In this example, the movement of the passenger could be detected by the motion sensors 311. In response to detecting the movement and/or the direction associated with the movement, the passenger may be prevented from interfacing with and/or accessing at least some of the vehicle control features. As can be appreciated, the user may be alerted of the movement/motion such that the user can act to prevent the passenger from interfering with the vehicle controls. Optionally, the number of motion sensors in a vehicle may be increased to increase an accuracy associated with motion detected in the vehicle 100.

Weight sensors 313 may be employed to collect data relating to objects and/or users in various areas of the vehicle 100. In some cases, the weight sensors 313 may be included in the seats and/or floor of a vehicle 100. Optionally, the vehicle 100 may include a wireless network sensor 315. This sensor 315 may be configured to detect one or more wireless network(s) inside the vehicle 100. Examples of wireless networks may include, but are not limited to, wireless communications utilizing Bluetooth®, Wi-Fi™, ZigBee, IEEE 802.11, and other wireless technology standards. For example, a mobile hotspot may be detected inside the vehicle 100 via the wireless network sensor 315. In this case, the vehicle 100 may determine to utilize and/or share the mobile hotspot detected via/with one or more other devices associated with the vehicle 100.

Biometric sensors 317 may be employed to identify and/or record characteristics associated with a user. It is anticipated that biometric sensors 317 can include at least one of image sensors, IR sensors, fingerprint readers, weight sensors, load cells, force transducers, heart rate monitors, blood pressure monitors, and the like as provided herein.

The camera sensors 319 may record still images, video, and/or combinations thereof. Camera sensors 319 may be used alone or in combination to identify objects, users, and/or other features, inside the vehicle 100. Two or more camera sensors 319 may be used in combination to form, among other things, stereo and/or three-dimensional (3D) images. The stereo images can be recorded and/or used to determine depth associated with objects and/or users in a vehicle 100. Further, the camera sensors 319 used in combination may determine the complex geometry associated with identifying characteristics of a user. For example, the camera sensors 319 may be used to determine dimensions between various features of a user's face (e.g., the depth/distance from a user's nose to a user's cheeks, a linear distance between the center of a user's eyes, and more). These dimensions may be used to verify, record, and even modify characteristics that serve to identify a user. The camera sensors 319 may also be used to determine movement associated with objects and/or users within the vehicle 100. It should be appreciated that the number of image sensors used in a vehicle 100 may be increased to provide greater dimensional accuracy and/or views of a detected image in the vehicle 100.

The audio sensors 321 may be configured to receive audio input from a user of the vehicle 100. The audio input from a user may correspond to voice commands, conversations detected in the vehicle 100, phone calls made in the vehicle 100, and/or other audible expressions made in the vehicle 100. Audio sensors 321 may include, but are not limited to, microphones and other types of acoustic-to-electric transducers or sensors. Optionally, the interior audio sensors 321 may be configured to receive and convert sound waves into an equivalent analog or digital signal. The interior audio sensors 321 may serve to determine one or more locations associated with various sounds in the vehicle 100. The location of the sounds may be determined based on a comparison of volume levels, intensity, and the like, between sounds detected by two or more interior audio sensors 321. For instance, a first audio sensor 321 may be located in a first area of the vehicle 100 and a second audio sensor 321 may be located in a second area of the vehicle 100. If a sound is detected at a first volume level by the first audio sensors 321 A and a second, higher, volume level by the second audio sensors 321 in the second area of the vehicle 100, the sound may be determined to be closer to the second area of the vehicle 100. As can be appreciated, the number of sound receivers used in a vehicle 100 may be increased (e.g., more than two, etc.) to increase measurement accuracy surrounding sound detection and location, or source, of the sound (e.g., via triangulation, etc.).

The safety sensors may comprise sensors configured to collect data relating to the safety of a user and/or one or more components of a vehicle 100. Examples of safety sensors may include one or more of, but are not limited to: force sensors 325, mechanical motion sensors 327, orientation sensors 329, restraint sensors 331, and more.

The force sensors 325 may include one or more sensors inside the vehicle 100 configured to detect a force observed in the vehicle 100. One example of a force sensor 325 may include a force transducer that converts measured forces (e.g., force, weight, pressure, etc.) into output signals. Mechanical motion sensors 327 may correspond to encoders, accelerometers, damped masses, and the like. Optionally, the mechanical motion sensors 327 may be adapted to measure the force of gravity (i.e., G-force) as observed inside the vehicle 100. Measuring the G-force observed inside a vehicle 100 can provide valuable information related to a vehicle's acceleration, deceleration, collisions, and/or forces that may have been suffered by one or more users in the vehicle 100. Orientation sensors 329 can include accelerometers, gyroscopes, magnetic sensors, and the like that are configured to detect an orientation associated with the vehicle 100.

The restraint sensors 331 may correspond to sensors associated with one or more restraint devices and/or systems in a vehicle 100. Seatbelts and airbags are examples of restraint devices and/or systems. As can be appreciated, the restraint devices and/or systems may be associated with one or more sensors that are configured to detect a state of the device/system. The state may include extension, engagement, retraction, disengagement, deployment, and/or other electrical or mechanical conditions associated with the device/system.

The associated device sensors 323 can include any sensors that are associated with a device in the vehicle 100. As previously stated, typical devices may include smart phones, tablets, laptops, mobile computers, and the like. It is anticipated that the various sensors associated with these devices can be employed by the vehicle control system 348. For example, a typical smart phone can include, an image sensor, an IR sensor, audio sensor, gyroscope, accelerometer, wireless network sensor, fingerprint reader, and more. It is an aspect of the present disclosure that one or more of these associated device sensors 323 may be used by one or more subsystems of the vehicle 100.

FIG. 3C illustrates a GPS/Navigation subsystem(s) 302. The navigation subsystem(s) 302 can be any present or future-built navigation system that may use location data, for example, from the Global Positioning System (GPS), to provide navigation information or control the vehicle 100. The navigation subsystem(s) 302 can include several components, such as, one or more of, but not limited to: a GPS Antenna/receiver 331, a location module 333, a maps database 335, etc. Generally, the several components or modules 331-335 may be hardware, software, firmware, computer readable media, or combinations thereof.

A GPS Antenna/receiver 331 can be any antenna, GPS puck, and/or receiver capable of receiving signals from a GPS satellite or other navigation system. The signals may be demodulated, converted, interpreted, etc. by the GPS Antenna/receiver 331 and provided to the location module 333. Thus, the GPS Antenna/receiver 331 may convert the time signals from the GPS system and provide a location (e.g., coordinates on a map) to the location module 333. Alternatively, the location module 333 can interpret the time signals into coordinates or other location information.

The location module 333 can be the controller of the satellite navigation system designed for use in the vehicle 100. The location module 333 can acquire position data, as from the GPS Antenna/receiver 331, to locate the user or vehicle 100 on a road in the unit's map database 335. Using the road database 335, the location module 333 can give directions to other locations along roads also in the database 335. When a GPS signal is not available, the location module 333 may apply dead reckoning to estimate distance data from sensors 304 including one or more of, but not limited to, a speed sensor attached to the drive train of the vehicle 100, a gyroscope, an accelerometer, etc. Additionally or alternatively, the location module 333 may use known locations of Wi-Fi hotspots, cell tower data, etc. to determine the position of the vehicle 100, such as by using time difference of arrival (TDOA) and/or frequency difference of arrival (FDOA) techniques.

The maps database 335 can include any hardware and/or software to store information about maps, geographical information system (GIS) information, location information, etc. The maps database 335 can include any data definition or other structure to store the information. Generally, the maps database 335 can include a road database that may include one or more vector maps of areas of interest. Street names, street numbers, house numbers, and other information can be encoded as geographic coordinates so that the user can find some desired destination by street address. Points of interest (waypoints) can also be stored with their geographic coordinates. For example, a point of interest may include speed cameras, fuel stations, public parking, and "parked here" (or "you parked here") information. The maps database 335 may also include road or street characteristics, for example, speed limits, location of stop lights/stop signs, lane divisions, school locations, etc. The map database contents can be produced or updated by a server connected through a wireless system in communication with the Internet, even as the vehicle 100 is driven along existing streets, yielding an up-to-date map.

Figure 4:
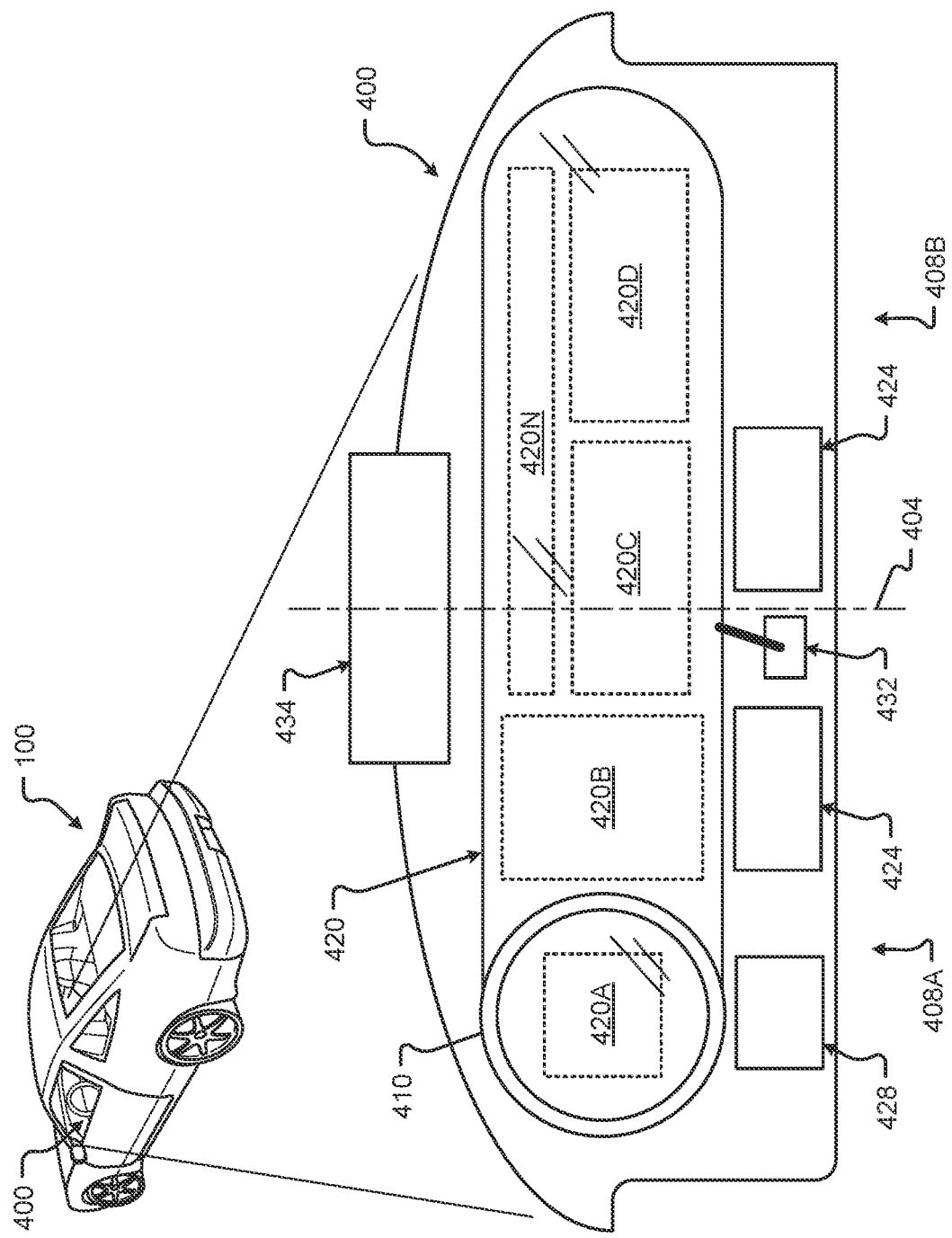
FIG. 4 shows an embodiment of the instrument panel of the vehicle according to one embodiment of the present disclosure.

FIG. 4 shows one embodiment of the instrument panel 400 of the vehicle 100. The instrument panel 400 of vehicle 100 comprises a steering wheel 410, a vehicle operational display 420 (e.g., configured to present and/or display driving data such as speed, measured air resistance, vehicle information, entertainment information, etc.), one or more auxiliary displays 424 (e.g., configured to present and/or display information segregated from the operational display 420, entertainment applications, movies, music, etc.), a heads-up display 434 (e.g., configured to display any information previously described including, but in no way limited to, guidance information such as route to destination, or obstacle warning information to warn of a potential collision, or some or all primary vehicle operational data such as speed, resistance, etc.), a power management display 428 (e.g., configured to display data corresponding to electric power levels of vehicle 100, reserve power, charging status, etc.), and an input device 432 (e.g., a controller, touchscreen, or other interface device configured to interface with one or more displays in the instrument panel or components of the vehicle 100. The input device 432 may be configured as a joystick, mouse, touchpad, tablet, 3D gesture capture device, etc.). In some embodiments, the input device 432 may be used to manually maneuver a portion of the vehicle 100 into a charging position (e.g., moving a charging plate to a desired separation distance, etc.).

While one or more of displays of instrument panel 400 may be touch-screen displays, it should be appreciated that the vehicle operational display may be a display incapable of receiving touch input. For instance, the operational display 420 that spans across an interior space centerline 404 and across both a first zone 408A and a second zone 408B may be isolated from receiving input from touch, especially from a passenger. In some cases, a display that provides vehicle operation or critical systems information and interface may be restricted from receiving touch input and/or be configured as a non-touch display. This type of configuration can prevent dangerous mistakes in providing touch input where such input may cause an accident or unwanted control.

In some embodiments, one or more displays of the instrument panel 400 may be mobile devices and/or applications residing on a mobile device such as a smart phone. Additionally or alternatively, any of the information described herein may be presented to one or more portions 420A-N of the operational display 420 or other display 424, 428, 434. In one embodiment, one or more displays of the instrument panel 400 may be physically separated or detached from the instrument panel 400. In some cases, a detachable display may remain tethered to the instrument panel.

The portions 420A-N of the operational display 420 may be dynamically reconfigured and/or resized to suit any display of information as described. Additionally or alternatively, the number of portions 420A-N used to visually present information via the operational display 420 may be dynamically increased or decreased as required, and are not limited to the configurations shown.

Figure 5:
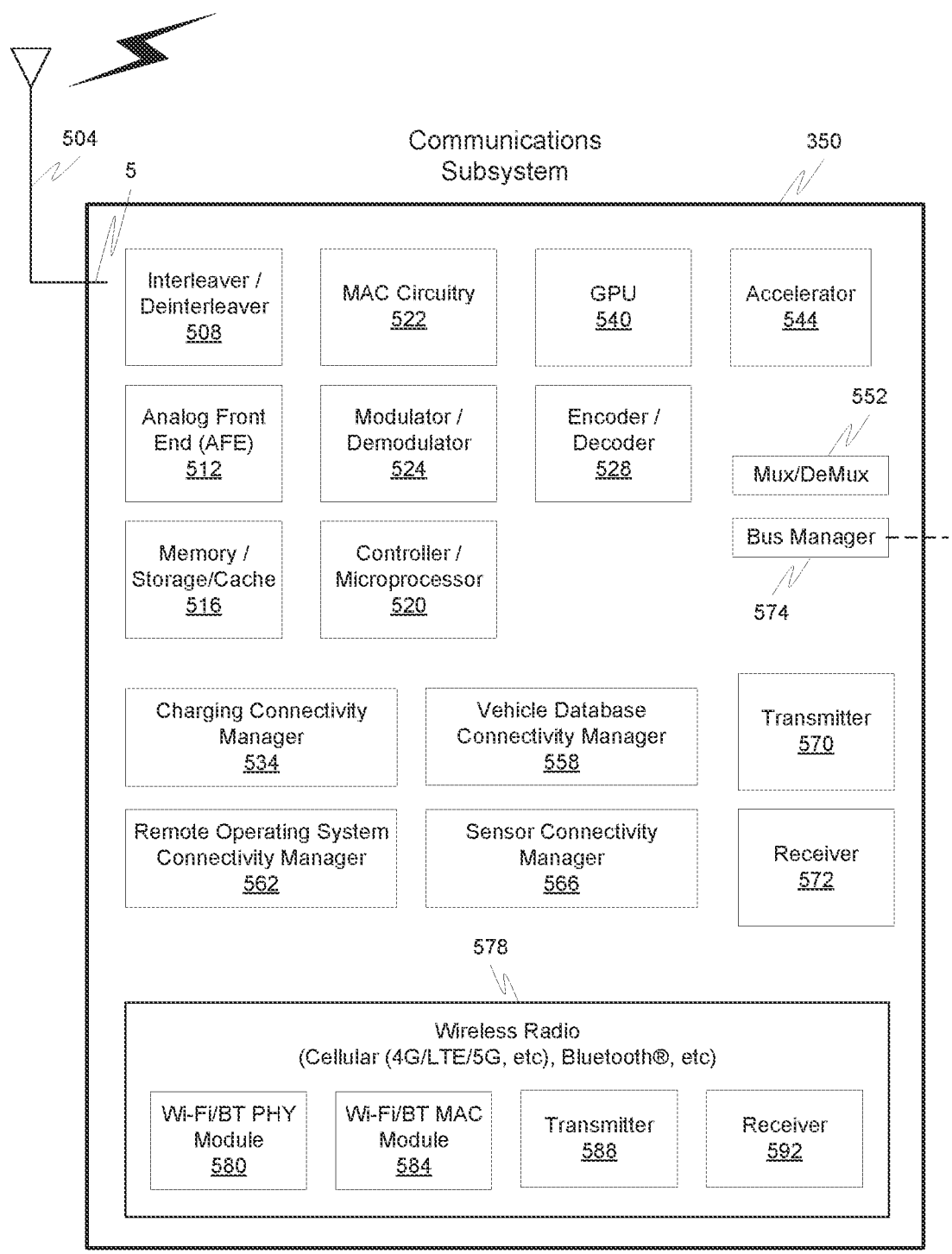
FIG. 5 is a block diagram of an embodiment of a communications subsystem of the vehicle.

FIG. 5 illustrates a hardware diagram of communications componentry that can be optionally associated with the vehicle 100 in accordance with embodiments of the present disclosure.

The communications componentry can include one or more wired or wireless devices such as a transceiver(s) and/or modem that allows communications not only between the various systems disclosed herein but also with other devices, such as devices on a network, and/or on a distributed network such as the Internet and/or in the cloud and/or with another vehicle(s).

The communications subsystem 350 can also include inter- and intra-vehicle communications capabilities such as hotspot and/or access point connectivity for any one or more of the vehicle occupants and/or vehicle-to-vehicle communications.

Additionally, and while not specifically illustrated, the communications subsystem 350 can include one or more communications links (that can be wired or wireless) and/or communications busses (managed by the bus manager 574), including one or more of CANbus, OBD-II, ARCINC 429, Byteflight, CAN (Controller Area Network), D2B (Domestic Digital Bus), FlexRay, DC-BUS, IDB-1394, IEBus, I2C, ISO 9141-1/-2, J1708, J1587, J1850, J1939, ISO 11783, Keyword Protocol 2000, LIN (Local Interconnect Network), MOST (Media Oriented Systems Transport), Multifunction Vehicle Bus, SMARTwireX, SPI, VAN (Vehicle Area Network), and the like or in general any communications protocol and/or standard(s).

The various protocols and communications can be communicated one or more of wirelessly and/or over transmission media such as single wire, twisted pair, fiber optic, IEEE 1394, MIL-STD-1553, MIL-STD-1773, power-line communication, or the like. (All of the above standards and protocols are incorporated herein by reference in their entirety).

As discussed, the communications subsystem 350 enables communications between any if the inter-vehicle systems and subsystems as well as communications with non-collocated resources, such as those reachable over a network such as the Internet.

The communications subsystem 350, in addition to well-known componentry (which has been omitted for clarity), includes interconnected elements including one or more of: one or more antennas 504, an interleaver/deinterleaver 508, an analog front end (AFE) 512, memory/storage/cache 516, controller/microprocessor 520, MAC circuitry 522, modulator/demodulator 524, encoder/decoder 528, a plurality of connectivity managers 534, 558, 562, 566, GPU 540, accelerator 544, a multiplexer/demultiplexer 552, transmitter 570, receiver 572 and wireless radio 578 components such as a Wi-Fi PHY/Bluetooth® module 580, a Wi-Fi/BT MAC module 584, transmitter 588 and receiver 592. The various elements in the device 350 are connected by one or more links/busses 5 (not shown, again for sake of clarity).

The device 350 can have one more antennas 504, for use in wireless communications such as multi-input multi-output (MIMO) communications, multi-user multi-input multi-output (MU-MIMO) communications Bluetooth®, LTE, 4G, 5G, Near-Field Communication (NFC), etc., and in general for any type of wireless communications. The antenna(s) 504 can include, but are not limited to one or more of directional antennas, omnidirectional antennas, monopoles, patch antennas, loop antennas, microstrip antennas, dipoles, and any other antenna(s) suitable for communication transmission/reception. In an exemplary embodiment, transmission/reception using MIMO may require particular antenna spacing. In another exemplary embodiment, MIMO transmission/reception can enable spatial diversity allowing for different channel characteristics at each of the antennas. In yet another embodiment, MIMO transmission/reception can be used to distribute resources to multiple users for example within the vehicle 100 and/or in another vehicle.

Antenna(s) 504 generally interact with the Analog Front End (AFE) 512, which is needed to enable the correct processing of the received modulated signal and signal conditioning for a transmitted signal. The AFE 512 can be functionally located between the antenna and a digital baseband system to convert the analog signal into a digital signal for processing and vice-versa.

The subsystem 350 can also include a controller/microprocessor 520 and a memory/storage/cache 516. The subsystem 350 can interact with the memory/storage/cache 516 which may store information and operations necessary for configuring and transmitting or receiving the information described herein. The memory/storage/cache 516 may also be used in connection with the execution of application programming or instructions by the controller/microprocessor 520, and for temporary or long term storage of program instructions and/or data. As examples, the memory/storage/cache 520 may comprise a computer-readable device, RAM, ROM, DRAM, SDRAM, and/or other storage device(s) and media.

The controller/microprocessor 520 may comprise a general purpose programmable processor or controller for executing application programming or instructions related to the subsystem 350. Furthermore, the controller/microprocessor 520 can perform operations for configuring and transmitting/receiving information as described herein. The controller/microprocessor 520 may include multiple processor cores, and/or implement multiple virtual processors. Optionally, the controller/microprocessor 520 may include multiple physical processors. By way of example, the controller/microprocessor 520 may comprise a specially configured Application Specific Integrated Circuit (ASIC) or other integrated circuit, a digital signal processor(s), a controller, a hardwired electronic or logic circuit, a programmable logic device or gate array, a special purpose computer, or the like.

The subsystem 350 can further include a transmitter 570 and receiver 572 which can transmit and receive signals, respectively, to and from other devices, subsystems and/or other destinations using the one or more antennas 504 and/or links/busses. Included in the subsystem 350 circuitry is the medium access control or MAC Circuitry 522. MAC circuitry 522 provides for controlling access to the wireless medium. In an exemplary embodiment, the MAC circuitry 522 may be arranged to contend for the wireless medium and configure frames or packets for communicating over the wired/wireless medium.

The subsystem 350 can also optionally contain a security module (not shown). This security module can contain information regarding but not limited to, security parameters required to connect the device to one or more other devices or other available network(s), and can include WEP or WPA/WPA-2 (optionally+AES and/or TKIP) security access keys, network keys, etc. The WEP security access key is a security password used by Wi-Fi networks. Knowledge of this code can enable a wireless device to exchange information with an access point and/or another device. The information exchange can occur through encoded messages with the WEP access code often being chosen by the network administrator. WPA is an added security standard that is also used in conjunction with network connectivity with stronger encryption than WEP.

In some embodiments, the communications subsystem 350 also includes a GPU 540, an accelerator 544, a Wi-Fi/BT/BLE PHY module 580 and a Wi-Fi/BT/BLE MAC module 584 and wireless transmitter 588 and receiver 592. In some embodiments, the GPU 540 may be a graphics processing unit, or visual processing unit, comprising at least one circuit and/or chip that manipulates and changes memory to accelerate the creation of images in a frame buffer for output to at least one display device. The GPU 540 may include one or more of a display device connection port, printed circuit board (PCB), a GPU chip, a metal-oxide-semiconductor field-effect transistor (MOSFET), memory (e.g., single data rate random-access memory (SDRAM), double data rate random-access memory (DDR) RAM, etc., and/or combinations thereof), a secondary processing chip (e.g., handling video out capabilities, processing, and/or other functions in addition to the GPU chip, etc.), a capacitor, heatsink, temperature control or cooling fan, motherboard connection, shielding, and the like.

The various connectivity managers 534, 558, 562, 566 manage and/or coordinate communications between the subsystem 350 and one or more of the systems disclosed herein and one or more other devices/systems. The connectivity managers 534, 558, 562, 566 include a charging connectivity manager 534, a vehicle database connectivity manager 558, a remote operating system connectivity manager 562, and a sensor connectivity manager 566.

The charging connectivity manager 534 can coordinate not only the physical connectivity between the vehicle 100 and a charging device/vehicle, but can also communicate with one or more of a power management controller, one or more third parties and optionally a billing system(s). As an example, the vehicle 100 can establish communications with the charging device/vehicle to one or more of coordinate interconnectivity between the two (e.g., by spatially aligning the charging receptacle on the vehicle with the charger on the charging vehicle) and optionally share navigation information. Once charging is complete, the amount of charge provided can be tracked and optionally forwarded to, for example, a third party for billing. In addition to being able to manage connectivity for the exchange of power, the charging connectivity manager 534 can also communicate information, such as billing information to the charging vehicle and/or a third party. This billing information could be, for example, the owner of the vehicle, the driver/occupant(s) of the vehicle, company information, or in general any information usable to charge the appropriate entity for the power received.

The vehicle database connectivity manager 558 allows the subsystem to receive and/or share information stored in the vehicle database. This information can be shared with other vehicle components/subsystems and/or other entities, such as third parties and/or charging systems. The information can also be shared with one or more vehicle occupant devices, such as an app (application) on a mobile device the driver uses to track information about the vehicle 100 and/or a dealer or service/maintenance provider. In general any information stored in the vehicle database can optionally be shared with any one or more other devices optionally subject to any privacy or confidentially restrictions.

The remote operating system connectivity manager 562 facilitates communications between the vehicle 100 and any one or more autonomous vehicle systems. These communications can include one or more of navigation information, vehicle information, other vehicle information, weather information, occupant information, or in general any information related to the remote operation of the vehicle 100.

The sensor connectivity manager 566 facilitates communications between any one or more of the vehicle sensors (e.g., the driving vehicle sensors and systems 304, etc.) and any one or more of the other vehicle systems. The sensor connectivity manager 566 can also facilitate communications between any one or more of the sensors and/or vehicle systems and any other destination, such as a service company, app, or in general to any destination where sensor data is needed.

In accordance with one exemplary embodiment, any of the communications discussed herein can be communicated via the conductor(s) used for charging. One exemplary protocol usable for these communications is Power-line communication (PLC). PLC is a communication protocol that uses electrical wiring to simultaneously carry both data, and Alternating Current (AC) electric power transmission or electric power distribution. It is also known as power-line carrier, power-line digital subscriber line (PDSL), mains communication, power-line telecommunications, or power-line networking (PLN). For DC environments in vehicles PLC can be used in conjunction with CAN-bus, LIN-bus over power line (DC-LIN) and DC-BUS.

The communications subsystem can also optionally manage one or more identifiers, such as an IP (internet protocol) address(es), associated with the vehicle and one or other system or subsystems or components therein. These identifiers can be used in conjunction with any one or more of the connectivity managers as discussed herein.

Figure 6:
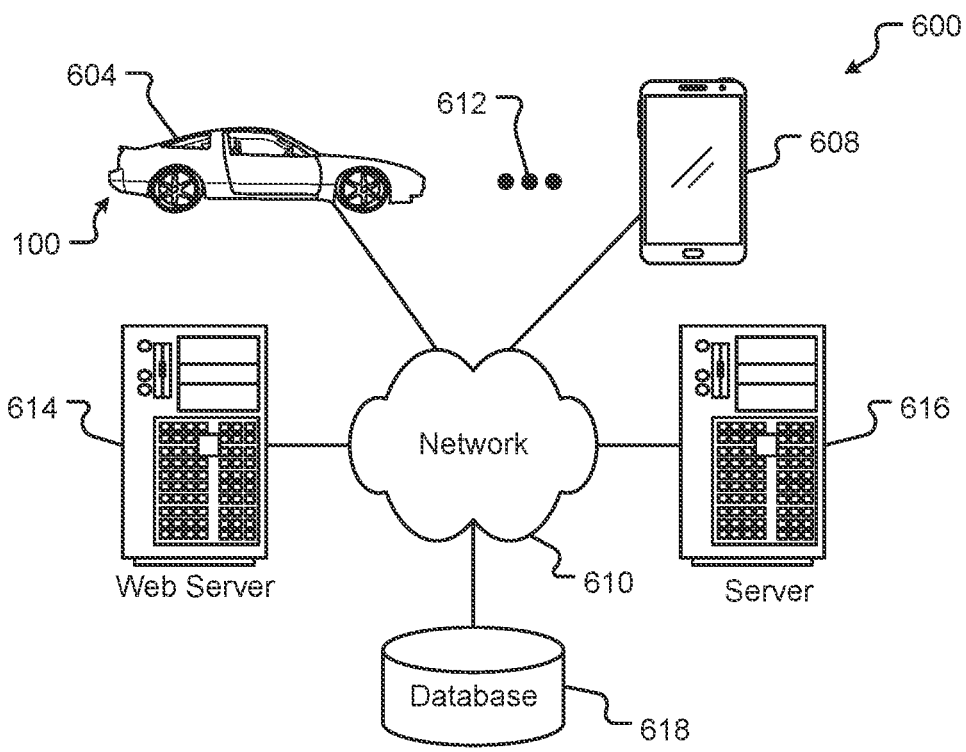
FIG. 6 is a block diagram of a computing environment associated with the embodiments presented herein.

FIG. 6 illustrates a block diagram of a computing environment 600 that may function as the servers, user computers, or other systems provided and described herein. The computing environment 600 includes one or more user computers, or computing devices, such as a vehicle computing device 604, a communication device 608, and/or more 612. The computing devices 604, 608, 612 may include general purpose personal computers (including, merely by way of example, personal computers, and/or laptop computers running various versions of Microsoft Corp.'s Windows® and/or Apple Corp.'s Macintosh® operating systems) and/or workstation computers running any of a variety of commercially-available UNIX® or UNIX-like operating systems. These computing devices 604, 608, 612 may also have any of a variety of applications, including for example, database client and/or server applications, and web browser applications. Alternatively, the computing devices 604, 608, 612 may be any other electronic device, such as a thin-client computer, Internet-enabled mobile telephone, and/or personal digital assistant, capable of communicating via a network 352 and/or displaying and navigating web pages or other types of electronic documents. Although the exemplary computing environment 600 is shown with two computing devices, any number of user computers or computing devices may be supported.

The computing environment 600 may also include one or more servers 614, 616. In this example, server 614 is shown as a web server and server 616 is shown as an application server. The web server 614, which may be used to process requests for web pages or other electronic documents from computing devices 604, 608, 612. The web server 614 can be running an operating system including any of those discussed above, as well as any commercially-available server operating systems. The web server 614 can also run a variety of server applications, including SIP (Session Initiation Protocol) servers, HTTP(s) servers, FTP servers, CGI servers, database servers, Java servers, and the like. In some instances, the web server 614 may publish operations available operations as one or more web services.

The computing environment 600 may also include one or more file and or/application servers 616, which can, in addition to an operating system, include one or more applications accessible by a client running on one or more of the computing devices 604, 608, 612. The server(s) 616 and/or 614 may be one or more general purpose computers capable of executing programs or scripts in response to the computing devices 604, 608, 612. As one example, the server 616, 614 may execute one or more web applications. The web application may be implemented as one or more scripts or programs written in any programming language, such as Java™, C, C#®, or C++, and/or any scripting language, such as Perl, Python, or TCL, as well as combinations of any programming/scripting languages. The application server(s) 616 may also include database servers, including without limitation those commercially available from Oracle®, Microsoft®, Sybase®, IBM® and the like, which can process requests from database clients running on a computing device 604, 608, 612.

The web pages created by the server 614 and/or 616 may be forwarded to a computing device 604, 608, 612 via a web (file) server 614, 616. Similarly, the web server 614 may be able to receive web page requests, web services invocations, and/or input data from a computing device 604, 608, 612 (e.g., a user computer, etc.) and can forward the web page requests and/or input data to the web (application) server 616. In further embodiments, the server 616 may function as a file server. Although for ease of description, FIG. 6 illustrates a separate web server 614 and file/application server 616, those skilled in the art will recognize that the functions described with respect to servers 614, 616 may be performed by a single server and/or a plurality of specialized servers, depending on implementation-specific needs and parameters. The computer systems 604, 608, 612, web (file) server 614 and/or web (application) server 616 may function as the system, devices, or components described in FIGS. 1-6.

The computing environment 600 may also include a database 618. The database 618 may reside in a variety of locations. By way of example, database 618 may reside on a storage medium local to (and/or resident in) one or more of the computers 604, 608, 612, 614, 616. Alternatively, it may be remote from any or all of the computers 604, 608, 612, 614, 616, and in communication (e.g., via the network 610) with one or more of these. The database 618 may reside in a storage-area network ("SAN") familiar to those skilled in the art. Similarly, any necessary files for performing the functions attributed to the computers 604, 608, 612, 614, 616 may be stored locally on the respective computer and/or remotely, as appropriate. The database 618 may be a relational database, such as Oracle 20i®, that is adapted to store, update, and retrieve data in response to SQL-formatted commands.

Figure 7:
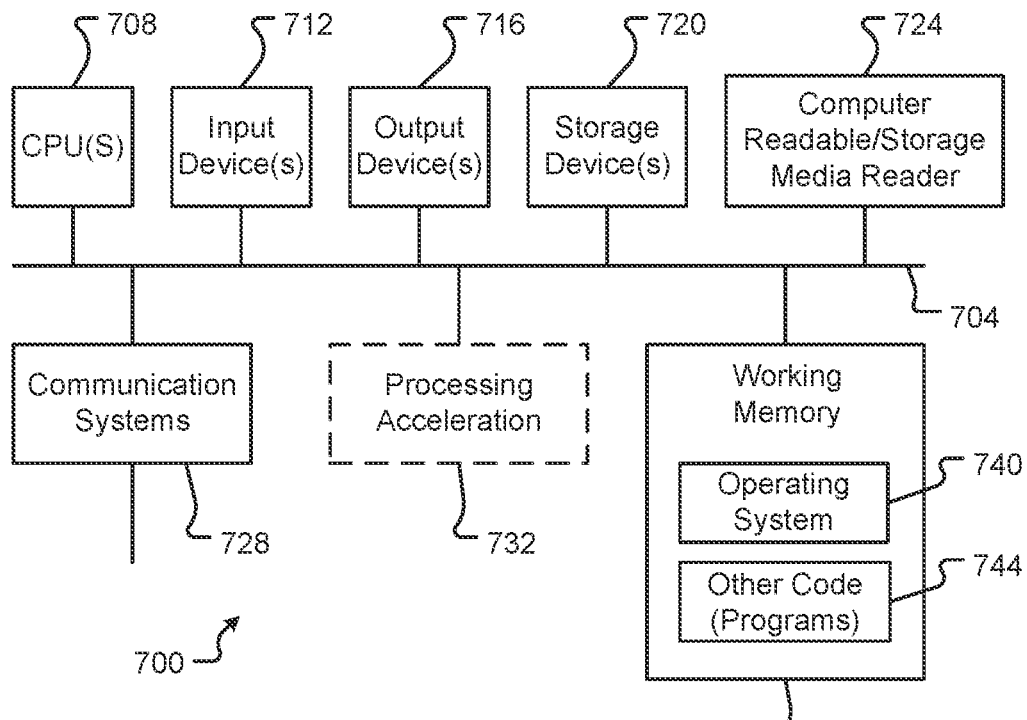
FIG. 7 is a block diagram of a computing device associated with one or more components described herein.

FIG. 7 illustrates one embodiment of a computer system 700 upon which the servers, user computers, computing devices, or other systems or components described above may be deployed or executed. The computer system 700 is shown comprising hardware elements that may be electrically coupled via a bus 704. The hardware elements may include one or more central processing units (CPUs) 708; one or more input devices 712 (e.g., a mouse, a keyboard, etc.); and one or more output devices 716 (e.g., a display device, a printer, etc.). The computer system 700 may also include one or more storage devices 720. By way of example, storage device(s) 720 may be disk drives, optical storage devices, solid-state storage devices such as a random access memory ("RAM") and/or a read-only memory ("ROM"), which can be programmable, flash-updateable and/or the like.

The computer system 700 may additionally include a computer-readable storage media reader 724; a communications system 728 (e.g., a modem, a network card (wireless or wired), an infra-red communication device, etc.); and working memory 736, which may include RAM and ROM devices as described above. The computer system 700 may also include a processing acceleration unit 732, which can include a DSP, a special-purpose processor, and/or the like.

The computer-readable storage media reader 724 can further be connected to a computer-readable storage medium, together (and, optionally, in combination with storage device(s) 720) comprehensively representing remote, local, fixed, and/or removable storage devices plus storage media for temporarily and/or more permanently containing computer-readable information. The communications system 728 may permit data to be exchanged with a network and/or any other computer described above with respect to the computer environments described herein. Moreover, as disclosed herein, the term "storage medium" may represent one or more devices for storing data, including read only memory (ROM), random access memory (RAM), magnetic RAM, core memory, magnetic disk storage mediums, optical storage mediums, flash memory devices and/or other machine readable mediums for storing information.

The computer system 700 may also comprise software elements, shown as being currently located within a working memory 736, including an operating system 740 and/or other code 744. It should be appreciated that alternate embodiments of a computer system 700 may have numerous variations from that described above. For example, customized hardware might also be used and/or particular elements might be implemented in hardware, software (including portable software, such as applets), or both. Further, connection to other computing devices such as network input/output devices may be employed.

Examples of the processors 340, 708 as described herein may include, but are not limited to, at least one of Qualcomm® Snapdragon® 800 and 801, Qualcomm® Snapdragon® 620 and 615 with 4G LTE Integration and 64-bit computing, Apple® A7 processor with 64-bit architecture, Apple® M7 motion coprocessors, Samsung® Exynos® series, the Intel® Core™ family of processors, the Intel® Xeon® family of processors, the Intel® Atom™ family of processors, the Intel Itanium® family of processors, Intel® Core® i5-4670K and i7-4770K 22 nm Haswell, Intel® Core® i5-3570K 22 nm Ivy Bridge, the AMD® FX™ family of processors, AMD® FX-4300, FX-6300, and FX-8350 32 nm Vishera, AMD® Kaveri processors, Texas Instruments® Jacinto C6000™ automotive infotainment processors, Texas Instruments® OMAP™ automotive-grade mobile processors, ARM® Cortex™-M processors, ARM® Cortex-A and ARM926EJ-S™ processors, other industry-equivalent processors, and may perform computational functions using any known or future-developed standard, instruction set, libraries, and/or architecture.

Figure 8:
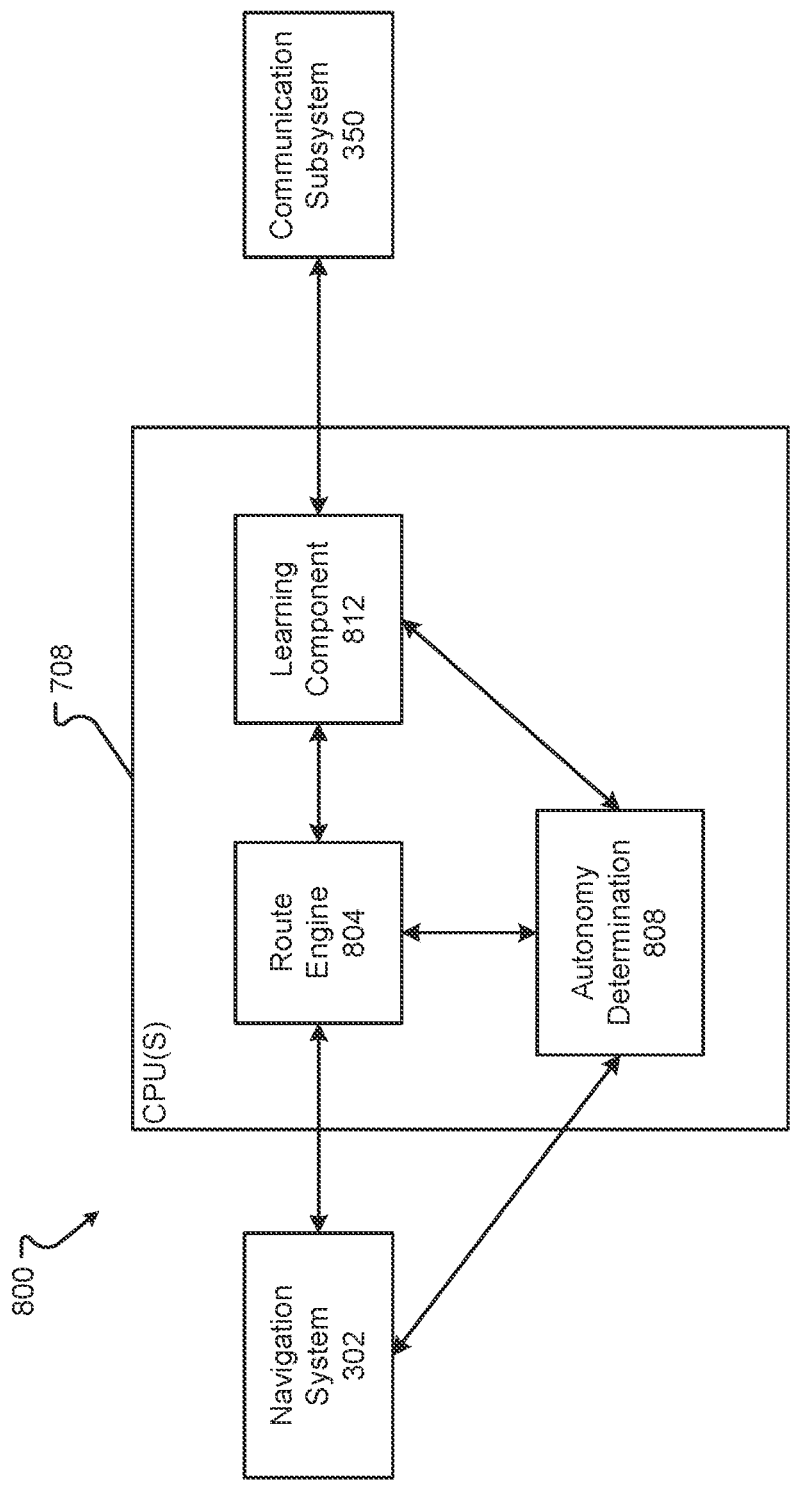
FIG. 8 is a block diagram of a computing system associated with one or more components described herein.

An embodiment of a system 800 for conducting the processes/methods described herein may be as shown in FIG. 8. The system 800 has various components which may, as shown in FIG. 8, be executed by a processor 708. However, in other configurations, the components can be hardware elements, which are formed from gates or circuits in a System-on-Chip (SOC), Application Specific Integrated Circuit (ASIC), and/or a Field Programmable Gate Array (FPGA). The components in system 800 can include one or more of, but are not limited to: a route engine 804, an autonomy determination component 808, and/or a learning component 812.

The route engine 804 can receive information from the navigation system 302, the autonomy determination component 808, and/or the learning component 812. The route engine 804 may determine a best route, which may have the most or least amount of autonomous driving availability. The route engine 804 can instruct the navigation system 302 about which of the available different routes to a destination from the current location is preferred. The navigation system 302 can then use that route to instruct the vehicle control system 348 controlling the autonomous driving functions of the vehicle 100.

The autonomy determination component 808 is operable to receive information from the learning component 812 and/or the navigation system 302 to provide a determination of the amount of autonomy for the one or more routes provided by the route engine 804 and/or navigation system 302. The autonomy determination component 812 can use the information, as described in conjunction with FIGS. 9A through 9C, store that information, retrieve that information, and/or weight that information for determining which route to use. The best route information may also be provided by the learning component 812, as the learning component 812 can receive information from a communication subsystem 350 from an external provider or may learn that information through various iterations of driving different routes. The information described above may be as described in conjunction with FIGS. 9A through 9C and may be weighted based on user preferences. User preferences may be received by the autonomy determination component 808 and/or previously stored by the autonomy determination component 808.

The learning component 812 can receive, as explained previously, information from the communication subsystem 350 from an external provider. For example, a mapping system 356A, a central server, or some other provider may provide different information about routes. Some of this information may be stored as static information, as explained in conjunction with FIG. 9A. In other situations, the learning component can receive real-time traffic or other types of dynamic info, which may be stored as data structure 928 described in conjunction with FIG. 9B. Regardless, learning component 812 can continually monitor the context of the driving situation and provide that information to the autonomy determination component 808 for determining the best route associated with the current driving context.

Figure 9C:
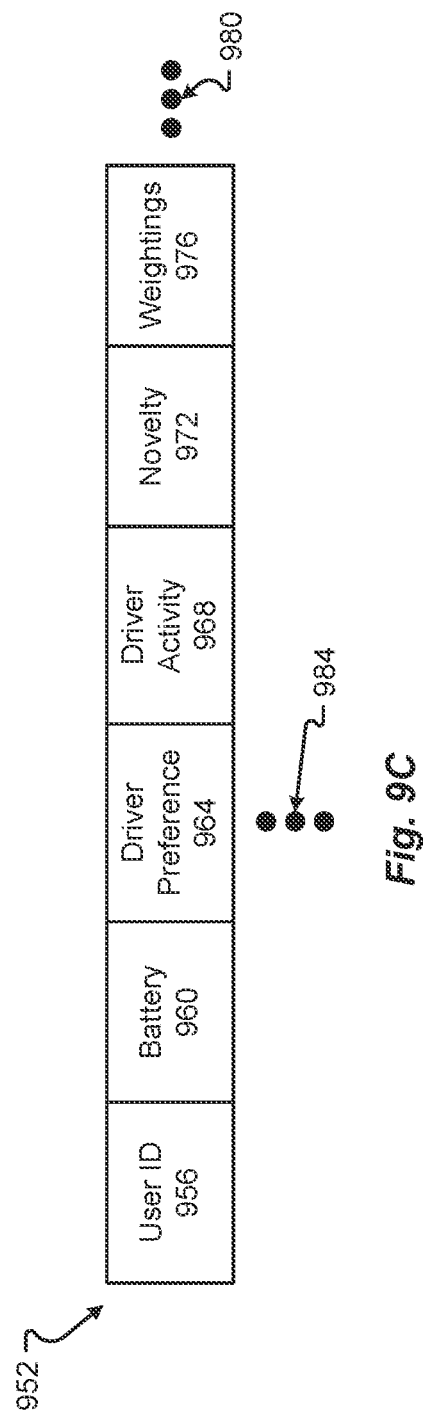
FIG. 9C is a data diagram of user/vehicle characteristics according to embodiments of the present disclosure.

Embodiments of data structures 900, 928, 952 are shown in FIGS. 9A, 9B, and 9C, which provide information about different routes that may be taken by the vehicle 100. Data structure 900, shown in FIG. 9A, can include one or more of, but is not limited to: a route identifier 904, static route characteristic 1 908, static route characteristic 2 912, and/or static route characteristic 3 916. There may be more or fewer route characteristics than that shown in FIG. 9A, as represented by ellipses 920. Each route may have a different data structure, and, as such, there may be more data structures 900 than that shown in FIG. 9A, as represented by ellipses 924. The route characteristics 908-916 can be different information about the route, including such things as the number of stoplights or stop signs on the route, whether there are school zones on the route, the speed limit of the route, and other static information. This information 908-916 is static as the information doesn't change (or changes infrequently) based on time of day or driving conditions. The static information 908-916 may be associated with a road, a highway, a portion of a road or highway, or some other portion of the driving environment.

These static route characteristics 908-916 may be associated with a route identifier (ID) 904. The route identifier 904 can be an alphanumeric identifier, a numeric identifier, a globally unique identifier (GUID), a street name, block addresses, or other types of identifiers that can identify the route or street. This route information 904 must be unique among all other routes, allowing the navigation system 302 to understand the route chosen and to provide this information to the route engine 804.

A set of dynamic route information may be provided in data structure 928, as shown in FIG. 9B. Similar to the static route information 900, the dynamic route information 928 includes a route ID 904, which may be the same or similar to the route ID 904 described in conjunction with FIG. 9A. Further, the dynamic route information data structure 928 can include one or more of, but is not limited to: dynamic route characteristic 1 932, dynamic route characteristic 2 936, and/or dynamic route characteristic 3 940. There may be more or fewer dynamic route characteristics 932-940 than those shown in FIG. 9B, as represented by ellipses 944. Each route identified by a route ID 904 can have a different data structure 928, and, as such, there may be more data structures 928 than that shown in FIG. 9B, as represented by ellipses 948.

The dynamic route characteristics 932-940 represent characteristics of the routes that change over time or change based on traffic or driving conditions. The dynamic route characteristics 932-940 can be such things as the amount of traffic currently on the route, the speed currently observed in the route, whether an emergency vehicle is using the route, or other types of information. Dynamic route information 932-940 can also include information about weather or other driving conditions. This information 932-940 changes consistently, periodically, and/or frequently and may be obtained by the learning component 812 from an outside provider or may be provided by another vehicle or by the vehicle 100 itself based on observation(s) by one or more sensors 304.

A data structure 952 that stores or manages car and driver information may be as shown in FIG. 9C. The data structure 952 can include one or more of, but is not limited to: a user identifier 956, battery information 960, driver preferences 964, driver activity 968, novelty information 972, weighting information 976, etc. There may be more or fewer driver/vehicle information fields than that shown in FIG. 9C, as represented by ellipses 980. Each user may have their own set of information or data structure 952, and, as such, there may be more data structures 952 than those shown in FIG. 9C, as represented by ellipses 934.

A user ID 956 can be any type of identifier (similar to the route ID 904) and can include an alphanumeric, a numeric, a GUID, a name, a username, or other types of user identifiers. The user ID 956 can also include biometric information that can be used to identify the user automatically with the sensors 304. The other information 960-976, in data structure 952, allows for customizing route selection based on the user driving the vehicle 100 and/or one or more users that reside within the vehicle 100 as a passenger(s).

Battery information 960 can include any type of information for the battery, which may change the selection of the route based on the needs for charging or range ability for a route. As such, the battery information 960 can include a charge level, a rate of discharge, the need for a charging station, a duration before a charge is needed, etc. This information 960 may be used to select a route where recharging the battery is possible.

The driver preferences 964 can include any type of learned or input information about how the driver desires the vehicle to proceed on any route. For example, some drivers may desire to use surface streets more than highways, may desire to travel streets with trees rather than more industrial areas, may desire to avoid certain areas of a town based on crime or other conditions, or may include other information. These driver preferences can help determine whether a route is desired by a user.

Driver activity 968 may be a dynamic attribute that determines the current activity of a user within the vehicle. Driver activity 968 can include such information as whether the user is texting, using a cellphone, using a computer or other device, whether the user seems to be sleepy or intoxicated, or other types of information. Thus, driver activity 968 may be information gleaned from biometric sensors 304 or other information. This driver activity information 968 may also indicate a time period or duration for an activity, for example, a duration for a meeting that is shown in the user's calendar for a user that the user is currently engaging in on a cellphone. Such duration information may provide a time limit or time minimum for a route. Other information may be included for determining an activity of a user.

Novelty information 972 can be information about the user and different routes and whether certain routes have been taken and how often, such that, the user does not get bored with the same commute. As such, novelty 972 may help to choose a route not previously, or seldom, selected, based on the user's desire to not travel the same route often. Novelty 972 may also be a security measure to ensure that the user does not travel the same route consistently and become a target for nefarious actors.

Weightings 976 can be user-determined or predetermined weightings for the different types of characteristics of a route. For example, a user may weight more heavily the speed at which a route is taken rather than another route characteristic. For example, a user may desire to get to a location quicker rather than enjoy a novel route set by the novel characteristic 972. These weightings may be input by a user or may be predetermined based on driver characteristics or some other information.

Figure 10:
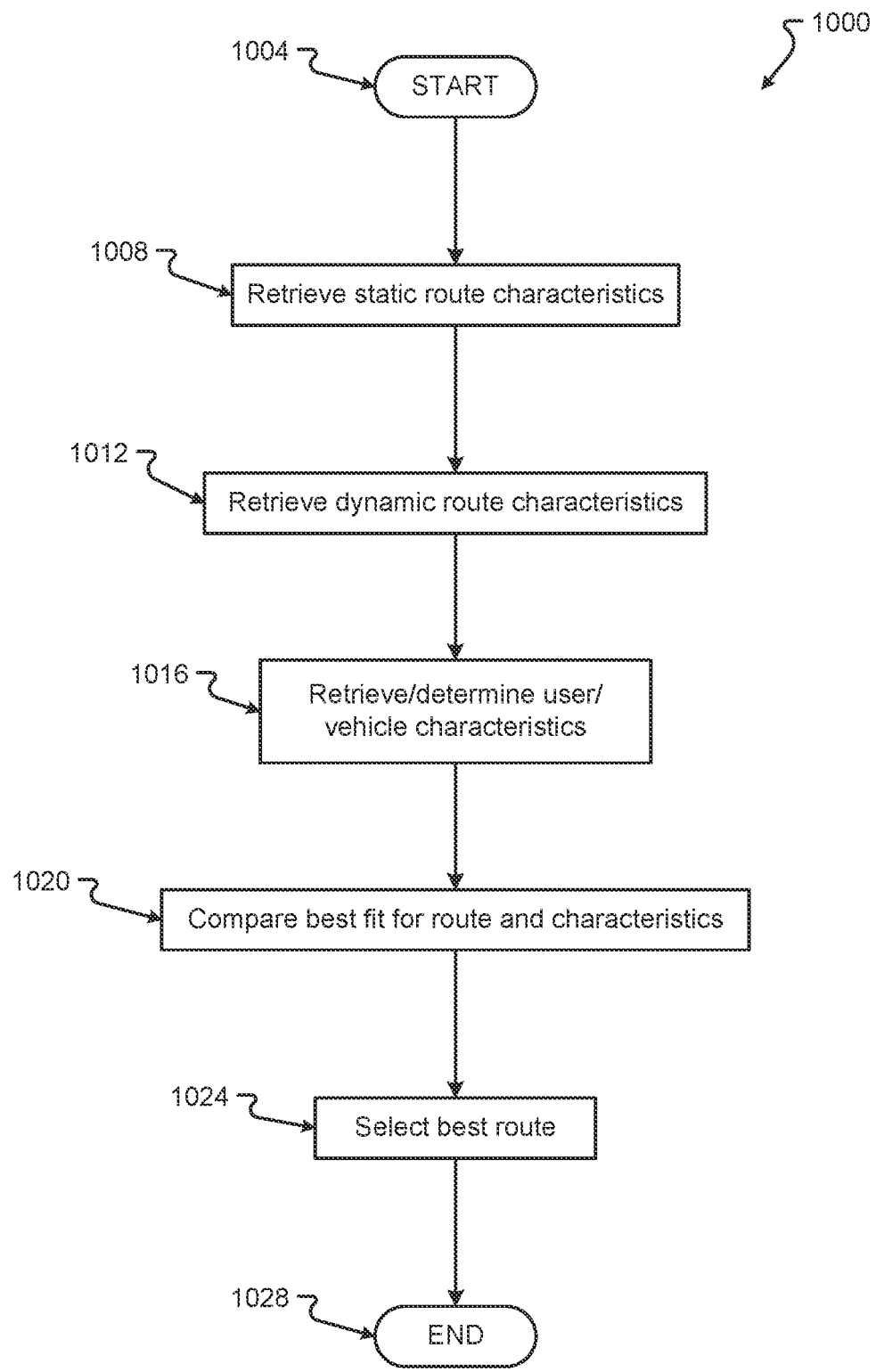
FIG. 10 is a flow diagram of an embodiment of a method for determining a best route for autonomous driving according to embodiments of the present disclosure.

An embodiment of method 1000 for dynamically selecting a route based on a driving context may be as shown in FIG. 10. Generally, the method 1000 starts with a start operation 1004 and ends with operation 1028. The method 1000 can include more or fewer steps or can arrange the order of the steps differently than those shown in FIG. 10. The method 1000 can be executed as a set of computer-executable instructions executed by a computer system or processor and encoded or stored on a computer readable medium. In other configurations, the method 1000 may be executed by a series of components, circuits, gates, etc. created in a hardware device, such as a System-on-Chip (SOC), Application Specific Integrated Circuit (ASIC), and/or a Field Programmable Gate Array (FPGA). Hereinafter, the method 1000 shall be explained with reference to the systems, components, circuits, modules, software, data structures, signalling processes, models, environments, vehicles, etc. described in conjunction with FIGS. 1-9.

The learning component 812 can receive static route characteristics 900, in step 1008. The learning component 812 may receive information 900 about different routes from a navigation map supplier 356A through the communication system 350. This static route information 900 may also be gleaned from other cars or based on graphical information system details. This information may be stored as static route information 900, as described in conjunction with FIG. 9A. Static information 900 may be retrieved by the autonomy determination component 808 from memory 516.

Similarly, the learning component 812 can receive dynamic characteristics 928 for routes, in step 1012. The learning component 812 may receive information 928 from sensors 304, from other vehicles, or from a third-party supplier 356A of real-time traffic or other dynamic information through the communication system 350. This dynamic information may be stored in dynamic information data structure 928, as described in conjunction with FIG. 9B. The learning component 812 can define this dynamic information 928, retrieve the information 928 from memory 516, and provide that information 928 to the autonomy determination component 808.

User/vehicle information 952 may be retrieved or determined, in step 1016. User characteristics and or vehicle characteristics, in data structure 952 may be obtained from sensor information or from information from the vehicle control system 348 or other vehicle systems. Thus, the battery characteristics 960 and other information about the vehicle 100 may also be provided in data structure 952. This information 952 may be provided to the autonomy determination component 808 by retrieving the data structure 952 from memory 516.

In step 1020, the autonomy determination component 808 determines the best fit for a route based on the different characteristics provided by the learning component 812 and/or other sources. Using weightings 976, the autonomy determination component 808 can weigh the different factors of two or more routes. Based on a score that measures the best to the weighted characteristics, the route autonomy determination component 808 can give a measure of the level of autonomy possible or a measure the desired fit of each route to the current driving context. This best fit information may then be provided to the route engine 804.

The route engine 804, which provided the different routes to the autonomy determination component 808, can then receive the information about the autonomy level or best fit for each route from the autonomy determination component 808. The route engine 804 may then select the best route out of the different options and provide that information to the navigation system 302. The selected route can be the route with the highest score that correlates to the route that is best for the current driving context. The navigation system 302 may then change or select the route presented to the user and then control the vehicle 348 based on the amount of autonomy allowed for or other characteristics associated with the route.

Any of the steps, functions, and operations discussed herein can be performed continuously and automatically.

The exemplary systems and methods of this disclosure have been described in relation to vehicle systems and electric vehicles. However, to avoid unnecessarily obscuring the present disclosure, the preceding description omits a number of known structures and devices. This omission is not to be construed as a limitation of the scope of the claimed disclosure. Specific details are set forth to provide an understanding of the present disclosure. It should, however, be appreciated that the present disclosure may be practiced in a variety of ways beyond the specific detail set forth herein.

Furthermore, while the exemplary embodiments illustrated herein show the various components of the system collocated, certain components of the system can be located remotely, at distant portions of a distributed network, such as a LAN and/or the Internet, or within a dedicated system. Thus, it should be appreciated, that the components of the system can be combined into one or more devices, such as a server, communication device, or collocated on a particular node of a distributed network, such as an analog and/or digital telecommunications network, a packet-switched network, or a circuit-switched network. It will be appreciated from the preceding description, and for reasons of computational efficiency, that the components of the system can be arranged at any location within a distributed network of components without affecting the operation of the system.

Furthermore, it should be appreciated that the various links connecting the elements can be wired or wireless links, or any combination thereof, or any other known or later developed element(s) that is capable of supplying and/or communicating data to and from the connected elements. These wired or wireless links can also be secure links and may be capable of communicating encrypted information. Transmission media used as links, for example, can be any suitable carrier for electrical signals, including coaxial cables, copper wire, and fiber optics, and may take the form of acoustic or light waves, such as those generated during radio-wave and infra-red data communications.

While the flowcharts have been discussed and illustrated in relation to a particular sequence of events, it should be appreciated that changes, additions, and omissions to this sequence can occur without materially affecting the operation of the disclosed embodiments, configuration, and aspects.

A number of variations and modifications of the disclosure can be used. It would be possible to provide for some features of the disclosure without providing others.

In yet another embodiment, the systems and methods of this disclosure can be implemented in conjunction with a special purpose computer, a programmed microprocessor or microcontroller and peripheral integrated circuit element(s), an ASIC or other integrated circuit, a digital signal processor, a hard-wired electronic or logic circuit such as discrete element circuit, a programmable logic device or gate array such as PLD, PLA, FPGA, PAL, special purpose computer, any comparable means, or the like. In general, any device(s) or means capable of implementing the methodology illustrated herein can be used to implement the various aspects of this disclosure. Exemplary hardware that can be used for the present disclosure includes computers, handheld devices, telephones (e.g., cellular, Internet enabled, digital, analog, hybrids, and others), and other hardware known in the art. Some of these devices include processors (e.g., a single or multiple microprocessors), memory, nonvolatile storage, input devices, and output devices. Furthermore, alternative software implementations including, but not limited to, distributed processing or component/object distributed processing, parallel processing, or virtual machine processing can also be constructed to implement the methods described herein.

In yet another embodiment, the disclosed methods may be readily implemented in conjunction with software using object or object-oriented software development environments that provide portable source code that can be used on a variety of computer or workstation platforms. Alternatively, the disclosed system may be implemented partially or fully in hardware using standard logic circuits or VLSI design. Whether software or hardware is used to implement the systems in accordance with this disclosure is dependent on the speed and/or efficiency requirements of the system, the particular function, and the particular software or hardware systems or microprocessor or microcomputer systems being utilized.

In yet another embodiment, the disclosed methods may be partially implemented in software that can be stored on a storage medium, executed on programmed general-purpose computer with the cooperation of a controller and memory, a special purpose computer, a microprocessor, or the like. In these instances, the systems and methods of this disclosure can be implemented as a program embedded on a personal computer such as an applet, JAVA® or CGI script, as a resource residing on a server or computer workstation, as a routine embedded in a dedicated measurement system, system component, or the like. The system can also be implemented by physically incorporating the system and/or method into a software and/or hardware system.

Although the present disclosure describes components and functions implemented in the embodiments with reference to particular standards and protocols, the disclosure is not limited to such standards and protocols. Other similar standards and protocols not mentioned herein are in existence and are considered to be included in the present disclosure. Moreover, the standards and protocols mentioned herein and other similar standards and protocols not mentioned herein are periodically superseded by faster or more effective equivalents having essentially the same functions. Such replacement standards and protocols having the same functions are considered equivalents included in the present disclosure.

The present disclosure, in various embodiments, configurations, and aspects, includes components, methods, processes, systems and/or apparatus substantially as depicted and described herein, including various embodiments, subcombinations, and subsets thereof. Those of skill in the art will understand how to make and use the systems and methods disclosed herein after understanding the present disclosure. The present disclosure, in various embodiments, configurations, and aspects, includes providing devices and processes in the absence of items not depicted and/or described herein or in various embodiments, configurations, or aspects hereof, including in the absence of such items as may have been used in previous devices or processes, e.g., for improving performance, achieving ease, and/or reducing cost of implementation.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments, configurations, or aspects for the purpose of streamlining the disclosure. The features of the embodiments, configurations, or aspects of the disclosure may be combined in alternate embodiments, configurations, or aspects other than those discussed above. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment, configuration, or aspect. Thus, the following claims are hereby incorporated into this Detailed Description, with each claim standing on its own as a separate preferred embodiment of the disclosure.

Moreover, though the description of the disclosure has included description of one or more embodiments, configurations, or aspects and certain variations and modifications, other variations, combinations, and modifications are within the scope of the disclosure, e.g., as may be within the skill and knowledge of those in the art, after understanding the present disclosure. It is intended to obtain rights, which include alternative embodiments, configurations, or aspects to the extent permitted, including alternate, interchangeable and/or equivalent structures, functions, ranges, or steps to those claimed, whether or not such alternate, interchangeable and/or equivalent structures, functions, ranges, or steps are disclosed herein, and without intending to publicly dedicate any patentable subject matter.

Embodiments include a vehicle, comprising: a sensor to sense an environment surrounding the vehicle; a vehicle control system to autonomously control driving functions of the vehicle; a navigation system, in communication with the sensor and the vehicle control system, to provide a selected route to the vehicle control system for autonomously controlling the vehicle along the selected route; and a processor, in communication with the sensor, the navigation system, and the vehicle control system, to: receive characteristics associated with two or more routes between a start point and an end point, wherein the characteristics define a driving context for each of the two or more routes; based on the characteristics, determine the selected route of the two or more routes that best fits the driving context; and provide the selected route to the navigation system.

Any of the one or more above aspects, wherein the characteristics include one or more of a static characteristic, a dynamic characteristic, a user characteristic, and/or a vehicle characteristic.

Any of the one or more above aspects, wherein the static characteristic includes one or more of an average number of lanes in each route segment along every viable route, an average number of traffic lights, a number of school zones, a number of stop signs, a number of yield signs, a number of lane merges, an average speed limit, and/or historical traffic or road occupant density for motorcycles, cars, trucks, cyclists, and/or pedestrians.

Any of the one or more above aspects, wherein the dynamic characteristic includes one or more of an amount of traffic currently on the route, a speed currently observed in the route, whether an emergency vehicle is using the route, weather and/or a driving condition.

Any of the one or more above aspects, wherein the user characteristic includes one or more of a driver preference, a driver activity, novelty information, and/or weighting information.

Any of the one or more above aspects, wherein the vehicle characteristic includes battery information.

Any of the one or more above aspects, wherein the battery information includes one or more of a charge level, a rate of discharge, a need for a charging station, and/or a duration before a charge is needed.

Any of the one or more above aspects, wherein a longer route is chosen based on an event in a user's calendar being conducted in the vehicle.

Any of the one or more above aspects, wherein the processor determines the best fit for the two or more routes by weighting the characteristics.

Any of the one or more above aspects, wherein the processor determines a best score based on the weighted characteristics.

Any of the one or more above aspects, wherein the route with the best score is the selected route.

Embodiments include a method, comprising: a processor receiving characteristics associated with two or more routes, for a vehicle, between a start point and an end point, wherein the characteristics define a driving context for each of the two or more routes; based on the characteristics, the processor determining a selected route of the two or more routes that best fits the driving context; the processor providing the selected route to a navigation system; the navigation system providing route directions for the selected route to a vehicle control system for autonomously controlling the vehicle along the selected route; and the vehicle control system autonomously controlling driving functions of the vehicle to maneuver the vehicle along the selected route.

Any of the one or more above aspects, wherein the characteristics include one or more of a static characteristic, a dynamic characteristic, a user characteristic, and/or a vehicle characteristic.

Any of the one or more above aspects, wherein the static characteristic includes one or more of an average number of lanes in each route segment along every viable route, an average number of traffic lights, a number of school zones, a number of stop signs, a number of yield signs, a number of lane merges, an average speed limit, and/or historical traffic or road occupant density for motorcycles, cars, trucks, cyclists, and/or pedestrians.

Any of the one or more above aspects, wherein the dynamic characteristic includes one or more of an amount of traffic currently on the route, a speed currently observed in the route, whether an emergency vehicle is using the route, weather and/or a driving condition.

Any of the one or more above aspects, wherein the processor determines the best fit for the two or more routes by weighting the characteristics, wherein the processor determines a best score based on the weighted characteristics, and wherein the route with the best score is the selected route.

Embodiments include a non-transitory information storage media having stored thereon one or more instructions, that when executed by one or more processors, cause a vehicle to perform a method, the method comprising: receiving characteristics associated with two or more routes, for a vehicle, between a start point and an end point, wherein the characteristics define a driving context for each of the two or more routes; based on the characteristics, determining a selected route of the two or more routes that best fits the driving context; providing the selected route to a navigation system; providing route directions for the selected route to a vehicle control system for autonomously controlling the vehicle along the selected route; and autonomously controlling driving functions of the vehicle to maneuver the vehicle along the selected route.

Any of the one or more above aspects, wherein the characteristics include one or more of a static characteristic, a dynamic characteristic, a user characteristic, and/or a vehicle characteristic, wherein the static characteristic includes one or more of an average number of lanes in each route segment along every viable route, an average number of traffic lights, a number of school zones, a number of stop signs, a number of yield signs, a number of lane merges, an average speed limit, and/or historical traffic or road occupant density for motorcycles, cars, trucks, cyclists, and/or pedestrians, and wherein the dynamic characteristic includes one or more of an amount of traffic currently on the route, a speed currently observed in the route, whether an emergency vehicle is using the route, weather and/or a driving condition.

Any of the one or more above aspects, wherein the processor determines the best fit for the two or more routes by weighting the characteristics, wherein the processor determines a best score based on the weighted characteristics, and wherein the route with the best score is the selected route.

Any of the one or more above aspects, wherein a longer route is chosen based on an event in a user's calendar being conducted in the vehicle, wherein the event is part of a driver activity characteristic.

Any one or more of the aspects/embodiments as substantially disclosed herein.

Any one or more of the aspects/embodiments as substantially disclosed herein optionally in combination with any one or more other aspects/embodiments as substantially disclosed herein.

One or means adapted to perform any one or more of the above aspects/embodiments as substantially disclosed herein.

The phrases "at least one," "one or more," "or," and "and/or" are open-ended expressions that are both conjunctive and disjunctive in operation. For example, each of the expressions "at least one of A, B and C," "at least one of A, B, or C," "one or more of A, B, and C," "one or more of A, B, or C," "A, B, and/or C," and "A, B, or C" means A alone, B alone, C alone, A and B together, A and C together, B and C together, or A, B and C together.

The term "a" or "an" entity refers to one or more of that entity. As such, the terms "a" (or "an"), "one or more," and "at least one" can be used interchangeably herein. It is also to be noted that the terms "comprising," "including," and "having" can be used interchangeably.

The term "automatic" and variations thereof, as used herein, refers to any process or operation, which is typically continuous or semi-continuous, done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material."

Aspects of the present disclosure may take the form of an embodiment that is entirely hardware, an embodiment that is entirely software (including firmware, resident software, micro-code, etc.) or an embodiment combining software and hardware aspects that may all generally be referred to herein as a "circuit," "module," or "system." Any combination of one or more computer-readable medium(s) may be utilized. The computer-readable medium may be a computer-readable signal medium or a computer-readable storage medium.

A computer-readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer-readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer-readable storage medium may be any tangible medium that can contain or store a program for use by or in connection with an instruction execution system, apparatus, or device.

A computer-readable signal medium may include a propagated data signal with computer-readable program code embodied therein, for example, in baseband or as part of a carrier wave. Such a propagated signal may take any of a variety of forms, including, but not limited to, electro-magnetic, optical, or any suitable combination thereof. A computer-readable signal medium may be any computer-readable medium that is not a computer-readable storage medium and that can communicate, propagate, or transport a program for use by or in connection with an instruction execution system, apparatus, or device. Program code embodied on a computer-readable medium may be transmitted using any appropriate medium, including, but not limited to, wireless, wireline, optical fiber cable, RF, etc., or any suitable combination of the foregoing.

The terms "determine," "calculate," "compute," and variations thereof, as used herein, are used interchangeably and include any type of methodology, process, mathematical operation or technique.

The term "electric vehicle" (EV), also referred to herein as an electric drive vehicle, may use one or more electric motors or traction motors for propulsion. An electric vehicle may be powered through a collector system by electricity from off-vehicle sources, or may be self-contained with a battery or generator to convert fuel to electricity. An electric vehicle generally includes a rechargeable electricity storage system (RESS) (also called Full Electric Vehicles (FEV)). Power storage methods may include: chemical energy stored on the vehicle in on-board batteries (e.g., battery electric vehicle or BEV), on board kinetic energy storage (e.g., flywheels), and/or static energy (e.g., by on-board double-layer capacitors). Batteries, electric double-layer capacitors, and flywheel energy storage may be forms of rechargeable on-board electrical storage.

The term "hybrid electric vehicle" refers to a vehicle that may combine a conventional (usually fossil fuel-powered) powertrain with some form of electric propulsion. Most hybrid electric vehicles combine a conventional internal combustion engine (ICE) propulsion system with an electric propulsion system (hybrid vehicle drivetrain). In parallel hybrids, the ICE and the electric motor are both connected to the mechanical transmission and can simultaneously transmit power to drive the wheels, usually through a conventional transmission. In series hybrids, only the electric motor drives the drivetrain, and a smaller ICE works as a generator to power the electric motor or to recharge the batteries. Power-split hybrids combine series and parallel characteristics. A full hybrid, sometimes also called a strong hybrid, is a vehicle that can run on just the engine, just the batteries, or a combination of both. A mid hybrid is a vehicle that cannot be driven solely on its electric motor, because the electric motor does not have enough power to propel the vehicle on its own.

The term "rechargeable electric vehicle" or "REV" refers to a vehicle with on board rechargeable energy storage, including electric vehicles and hybrid electric vehicles.

What is claimed is:

1. A vehicle, comprising:
   a first set of sensors to sense an environment surrounding the vehicle;
   a second set of sensors to sense an activity of an occupant in the vehicle;
   a third set of sensors to sense a state of the vehicle;
   a vehicle control system for autonomously controlling driving functions of the vehicle;
   a navigation system in communication with the first, second, and third sets of sensors and the vehicle control system, to provide a selected route to the vehicle control system for autonomously controlling the vehicle along the selected route; and
   a processor in communication with the first, second, and third sets of sensors, the navigation system, and the vehicle control system, the processor:
     receiving static route characteristics that are not anticipated to change for each of the two or more routes;
     receiving dynamic route characteristics that change for each of the two or more routes;
     selecting a level of autonomy, from among a plurality of levels of autonomy, based on the sensed activity of the occupant;
     selecting, based on the static route characteristics, the dynamic route characteristics, and occupant route preferences for each of the two or more routes, a route of the two or more routes that best fits the selected level of autonomy, the sensed environment surrounding the vehicle, and the sensed state of the vehicle; and
     providing the selected route to the navigation system.

2. The vehicle of claim 1, wherein, for each of the two or more routes, the static route characteristics are received in a first data structure that includes the static route characteristics and a route ID that identifies a respective route, wherein, for each of the two or more routes, the dynamic route characteristics are received in a second data structure that includes the dynamic route characteristics and the route ID that identifies the respective route, and wherein, for each of the two or more routes, the occupant route preferences are received in a third data structure that includes the occupant route preferences and a user ID that identifies the occupant.

3. The vehicle of claim 1, wherein the static route characteristics comprise one or more of an average number of lanes in each route segment along every viable route, an average number of traffic lights, a number of school zones, a number of stop signs, a number of yield signs, a number of lane merges, an average speed limit, or historical traffic or road occupant density for motorcycles, cars, trucks, cyclists, and pedestrians.

4. The vehicle of claim 1, wherein the dynamic route characteristics comprise one or more of an amount of traffic currently on each of the two or more routes, a speed currently observed in each of the two or more routes, whether an emergency vehicle is using each of the two or more routes, weather or a driving condition.

5. The vehicle of claim 1, wherein the occupant route preferences comprise novelty information that indicates the occupant of the vehicle desires to vary the selected route as a security measure to ensure the vehicle does not travel a same route consistently.

6. The vehicle of claim 5, wherein the occupant route preferences comprise weighting information and one or more of a driver preference, and a driver activity, wherein the weighting information includes occupant preferences on route speed, route average speed limit, route traffic density, or route driving conditions.

7. The vehicle of claim 6, wherein the sensed state of the vehicle includes battery information, and wherein the battery information includes one or more of a charge level, a rate of discharge, a need for a charging station, or a duration before a charge is needed.

8. The vehicle of claim 1, wherein the processor accesses a calendar of a driver or of a passenger of the vehicle, wherein the processor chooses the selected level of autonomy and the selected route based on an event in the calendar of the driver or of the passenger, wherein the processor chooses a longer route as the selected route to match a length of the event in the calendar.

9. The vehicle of claim 1, wherein the processor determines the selected route as a best fit for the two or more routes by weighting one or more of the static route characteristics, the dynamic route characteristics, or the occupant route preferences, wherein the selected level of autonomy is selected from one of level 0, level 1, level 2, level 3, level 4, or level 5, wherein the level 0 corresponds to a "No Automation" level where the vehicle is not responsible for any of the driving functions of the vehicle, wherein the level 1 corresponds to a "Driver Assistance" level where the vehicle controls throttle and/or braking operations of the driving functions of the vehicle, wherein the level 2 corresponds to a "Partial Automation" level where the vehicle collects information and uses the collected information to control the driving functions of the vehicle, wherein the level 3 corresponds to a "Conditional Automation" where a driver is separated from controlling all the driving functions of the vehicle except when the vehicle requests the driver to act or intervene in controlling the driving functions, wherein the level 4 corresponds to a "High Automation" level where the driver is separated from controlling all the driving functions of the vehicle and the vehicle controls the driving functions of the vehicle even when the driver fails to respond to a request to intervene, wherein the level 5 corresponds to a "Full Automation" level where the vehicle continually monitors all roadway and environmental conditions and no human driver interaction is required.

10. The vehicle of claim 9, wherein the processor determines a best score based on the weighted information.

11. The vehicle of claim 10, wherein a route with a best score is the selected route.

12. A method, comprising:
  receiving, for each of two or more routes between a common start point and a common end point, static route characteristics that are not anticipated to change for each of the two or more routes;
  receiving dynamic route characteristics that change for each of the two or more routes;
  receiving sensor data about a sensed environment surrounding the vehicle, a sensed activity of the occupant of the vehicle, and a sensed state of the vehicle;
  selecting a level of autonomy, from among a plurality of levels of autonomy, based on the sensed activity of the occupant;
  selecting based on the static route characteristics, the dynamic route characteristics, and occupant route preferences for each of the two or more routes, a route of the two or more routes that best fits the selected level of autonomy, the sensed environment, and the sensed state of the vehicle; and
  providing route directions for the selected route to a vehicle control system for controlling the vehicle along the selected route.

13. The method of claim 12, wherein, for each of the two or more routes, the static route characteristics are received in a first data structure that includes the static route characteristics and a route ID that identifies a respective route, wherein, for each of the two or more routes, the dynamic route characteristics are received in a second data structure that includes the dynamic route characteristics and the route ID that identifies the respective route, and wherein, for each of the two or more routes, the occupant route preferences are received in a third data structure that includes the occupant route preferences and a user ID that identifies the occupant.

14. The method of claim 12, wherein the static route characteristics include one or more of an average number of lanes in each route segment along every viable route, an average number of traffic lights, a number of school zones, a number of stop signs, a number of yield signs, a number of lane merges, an average speed limit, or historical traffic or road occupant density for motorcycles, cars, trucks, cyclists, and pedestrians.

15. The method of claim 12, wherein the dynamic route characteristics include one or more of an amount of traffic currently on each of the two or more routes, a speed currently observed in each of the two or more routes, whether an emergency vehicle is using each of the two or more routes, weather, or a driving condition.

16. The method of claim 12, wherein the selected route is determined as a best fit for the two or more routes by weighting one or more of the static route characteristics, the dynamic route characteristics, or the occupant route preferences, wherein a best score is determined based on the weighted one or more of the static route characteristics, and wherein a route with a best score is the selected route.

17. A non-transitory information storage media having stored thereon one or more instructions, that when executed by one or more processors, cause a vehicle to perform a method, the method, comprising:

receiving, for each of two or more routes between a common start point and a common end point, static route characteristics that are not anticipated to change for each of the two or more routes;

receiving dynamic route characteristics that change for each of the two or more routes;

receiving sensor data about a sensed environment surrounding the vehicle, a sensed activity of the occupant of the vehicle, and a sensed state of the vehicle;

selecting a level of autonomy, from among a plurality of levels of autonomy, based on the sensed activity of the occupant;

selecting, based on the static route characteristics and the dynamic route characteristics for each of the two or more routes, a route of the two or more routes that best fits the selected level of autonomy, the sensed environment, and the sensed state of the vehicle; and providing route directions for the selected route to a vehicle control system for controlling the vehicle along the selected route.

18. The non-transitory information storage media of claim 17, wherein, for each of the two or more routes, the static route characteristics are received in a first data structure that includes the static route characteristics and a route ID that identifies a respective route, wherein, for each of the two or more routes, the dynamic route characteristics are received in a second data structure that includes the dynamic route characteristics and the route ID that identifies the respective route, and wherein, for each of the two or more routes, the user route characteristics are received in a third data structure that includes the user route characteristics and a user ID that identifies the occupant.

19. The non-transitory information storage media of claim 17, wherein the selected level of autonomy is selected from one of level 0, level 1, level 2, level 3, level 4, or level 5, wherein the level 0 corresponds to a "No Automation" level where the vehicle is not responsible for any of the driving functions of the vehicle, wherein the level 1 corresponds to a "Driver Assistance" level where the vehicle controls throttle and/or braking operations of the driving functions of the vehicle, wherein the level 2 corresponds to a "Partial Automation" level where the vehicle collects information and uses the collected information to control the driving functions of the vehicle, wherein the level 3 corresponds to a "Conditional Automation" where a driver is separated from controlling all the driving functions of the vehicle except when the vehicle requests the driver to act or intervene in controlling the driving functions of the vehicle, wherein the level 4 corresponds to a "High Automation" level where the driver is separated from controlling all the driving functions of the vehicle and the vehicle controls the driving functions of the vehicle even when the driver fails to respond to a request to intervene, wherein the level 5 corresponds to a "Full Automation" level where the vehicle continually monitors all roadway and environmental conditions and no human driver interaction is required.

20. The non-transitory information storage media of claim 17, wherein a longer route is chosen based on an event in the occupant's calendar being conducted in the vehicle.

\* \* \* \* \*